(12) United States Patent
Dimitrov

(10) Patent No.: US 8,580,927 B2
(45) Date of Patent: Nov. 12, 2013

(54) ENGINEERED ANTIBODY CONSTANT DOMAIN MOLECULES

(75) Inventor: Dimiter S. Dimitrov, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 453 days.

(21) Appl. No.: 12/864,758

(22) PCT Filed: Jan. 30, 2009

(86) PCT No.: PCT/US2009/032692
§ 371 (c)(1),
(2), (4) Date: Jul. 27, 2010

(87) PCT Pub. No.: WO2009/099961
PCT Pub. Date: Aug. 13, 2009

(65) Prior Publication Data
US 2010/0316641 A1    Dec. 16, 2010

Related U.S. Application Data

(60) Provisional application No. 61/063,245, filed on Jan. 31, 2008.

(51) Int. Cl.
*C07K 16/00* (2006.01)
*A61K 39/395* (2006.01)

(52) U.S. Cl.
USPC .................. 530/387.3; 530/387.1; 424/130.1; 424/133.1

(58) Field of Classification Search
None
See application file for complete search history.

(56) References Cited

U.S. PATENT DOCUMENTS

| 5,965,709 | A | 10/1999 | Presta et al. |
| 6,277,375 | B1 | 8/2001 | Ward |
| 2005/0136049 | A1 | 6/2005 | Ledbetter et al. |
| 2007/0148170 | A1 | 6/2007 | Desjarlais et al. |
| 2012/0230981 | A1 * | 9/2012 | Bramhill et al. ........... 424/133.1 |

FOREIGN PATENT DOCUMENTS

| WO | WO 2006/036834 |   | 4/2006 |
| WO | WO 2006/072620 | * | 7/2006 |
| WO | WO 2006/114700 |   | 11/2006 |
| WO | WO 2007/076319 |   | 7/2007 |
| WO | WO 2008/100470 |   | 8/2008 |
| WO | WO 2008/153745 |   | 12/2008 |

OTHER PUBLICATIONS

Vajdos et al., J. Mol. Biol. 2002; 320(2); 415-28.*
UniProtKB/Swiss-Prot human IgG1 heavy chain reference sequence P01857.1, created Jul. 21, 1986 and last updated Mar. 6, 2013.*
Dimitrov DS, mAbs 2009; 1:26-28.*
Gong et al., PLOS One, 2012; 9(8):e42288 doci:10.1371/journal.pone.0042288, pp. 1-13.*
Gong et al., J Biol Chem 2011; 286:27288-293.*
Gong et al., Mol. Pharmaceutics 2013; 10:2642-52.*
Austin, "Will dAbs challenge mAbs?" Nature, vol. 341, Oct. 12, 1989, pp. 484-485.
Baral et al., "Experimental therapy of African trypanosomiasis with a nanobody-conjugated human trypanolytic factor," Nature Medicine, vol. 12, No. 5, May 2006, pp. 580-584.
Cortez-Retamozo et al., "Efficient Cancer Therapy with a Nanobody-Based Conjugate," Cancer Research, vol. 64, Apr. 15, 2004, pp. 2853-2857.
Feige et al., "Folding mechanism of the CH2 Antibody Domain," Journal of Molecular Biology, vol. 344, No. 1, Nov. 12, 2004, pp. 107-118.
Gong et al., "Engineered human antibody constant domains with increased stability," The Journal of Biological Chemistry, vol. 284, No. 21, May 22, 2009, pp. 14203-14210.
Lipovsek et al., "Evolution of an Interloop Disulfide Bond in High-Affinity Antibody Mimics Based on Fibronectin Type III Domain and Selected by yeast Surface Display: Molecular Convergence with Single-Domain Camelid and Shark Antibodies," Journal of Molecular Biology, vol. 368, No. 4, Apr. 17, 2007, pp. 1024-1041.
Skerra, "Engineered Protein Scaffolds for Molecular Recognition," Journal of Molecular Recognition, vol. 13, No. 4, Jul. 1, 2000, pp. 167-187.
Thies et al., "Folding and Oxidation of the Antibody Domain CH3," Journal of Molecular Biology, vol. 319, No. 5, Jun. 21, 2002, pp. 1267-1277.
Thies et al., "The alternatively folded state of the antibody CH3 domain," Journal of Molecular Biology, vol. 309, No. 5, Jun. 22, 2001, pp. 1077-1085.
Ward et al., "Binding activities of a repertoire of single immunoglobulin variable domains secreted from *Escherichia coli*," Nature, vol. 341, Oct. 12, 1989, pp. 544-546.
International Search Report and Written Opinion for PCT/US2009/032692, dated Jul. 17, 2009, 27 pages.

* cited by examiner

*Primary Examiner* — Misook Yu
*Assistant Examiner* — Jessica H Roark
(74) *Attorney, Agent, or Firm* — Klarquist Sparkman, LLP

(57) ABSTRACT

Described herein are engineered antibody constant domain molecules, such as CH2 or CH3 domain molecules, comprising at least one mutation, or comprising at least one complementarity determining region (CDR), or a functional fragment thereof, engrafted in a loop region of the CH2 domain. The CH2 domain molecules described herein are small, stable, soluble, exhibit little to no toxicity and are capable of binding antigen.

25 Claims, 32 Drawing Sheets

FIG. 1B

```
                                                   H1                            H2
                                                  CDR1                          CDR2
              .....    ....     ....     ....     ....     ....     ....     ....     ....     ....     ....     ....     ..
                  5       10       15       20       25       30  ab  35       40       45       50  abc  55       60       65
human         EVQLVESGGGLVQPGGSLRLSCAASGFTFS  S--YAMS  WVRQAPGKGLEWVS  XISXKTDGGTYYADSVKG Ab #1         HVQLGESGGGVVRPGGSLRLSCAASGFTFS  S--YAMS  WVRQAPGKGLEWVS  AISG--SGGSTYYADSVKG
Ab #2         QVQKVESGGGLVQPGGSLRLSCAASGFIFS  S--YAMS  WVRQAPGKGLEWVS  AISG--SGGSTYYADSVKG
Ab #3         QVQLVQSGAEVKKPGASVKVSCKASGYTFT  S--YYMH  WVRQAPGQGLEWMG  IINP--SGGSTSYAQKFQG H3
                                                                 CDR3
              .....    ....     ....     ....     ....     ....     ....     ....     ....     ....     ....     ....
                 70       75       80  abc  85       90       94                   100 b d f h j 100       105       110
human         RFTISRDNS-KNTLYLQMNSLRAEDTAVYYCAR  xxxxxxxxxxxxxxxx------FDY  WGQGTLVTVSS    (SEQ ID NO: 1)

Ab #1         RFTISRRNA-KNSLYLQMNSLRAEDTAVYYCAR  RGGVWA--------------FDI  WGQGTMVTVSS    (SEQ ID NO: 2)
Ab #2         RFTISRDNS-KNTLYLQMNSLRAEDTAVYYCAK  DLGRQQL-------------SDY  WGQGTLVTVSS    (SEQ ID NO: 3)
Ab #3         RVTMTRDTS-TSTVYMELSSLRSEDTAVYYCAT  PYG-----------------MDV  WGQGTTVTVSS    (SEQ ID NO: 4)
```

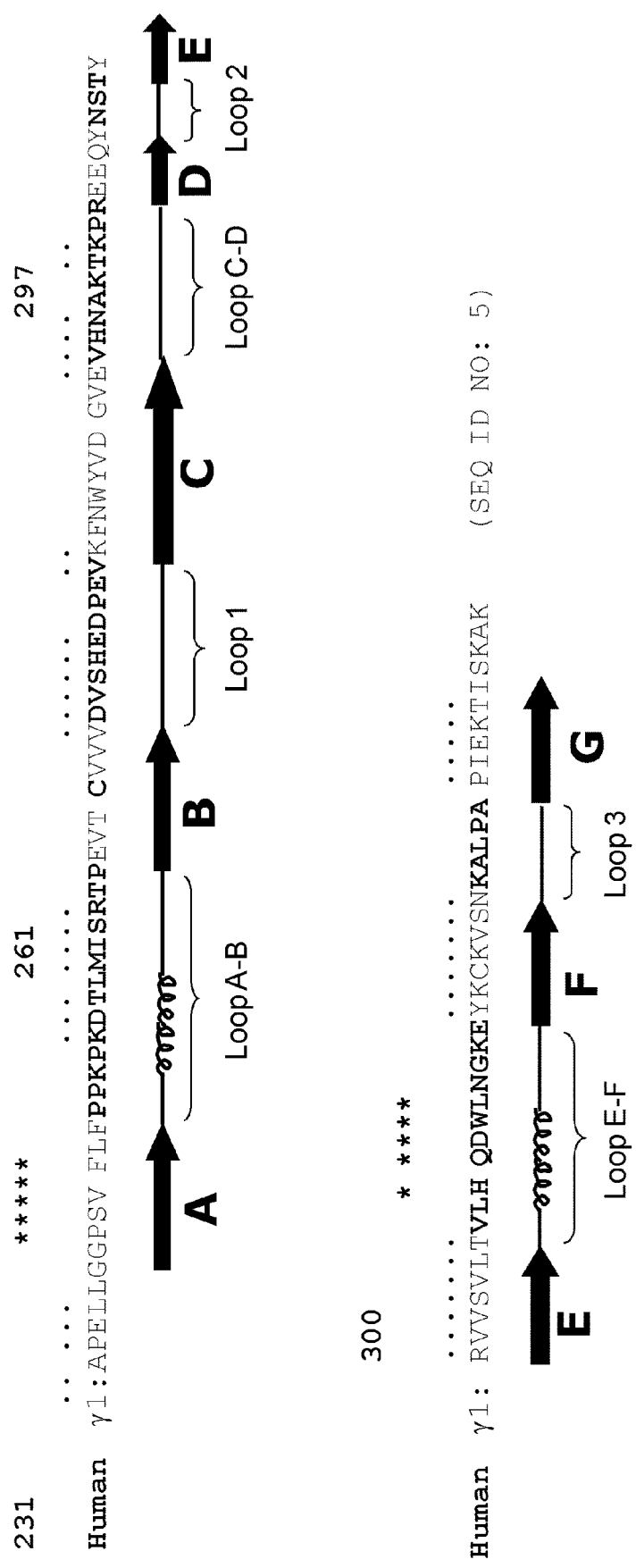

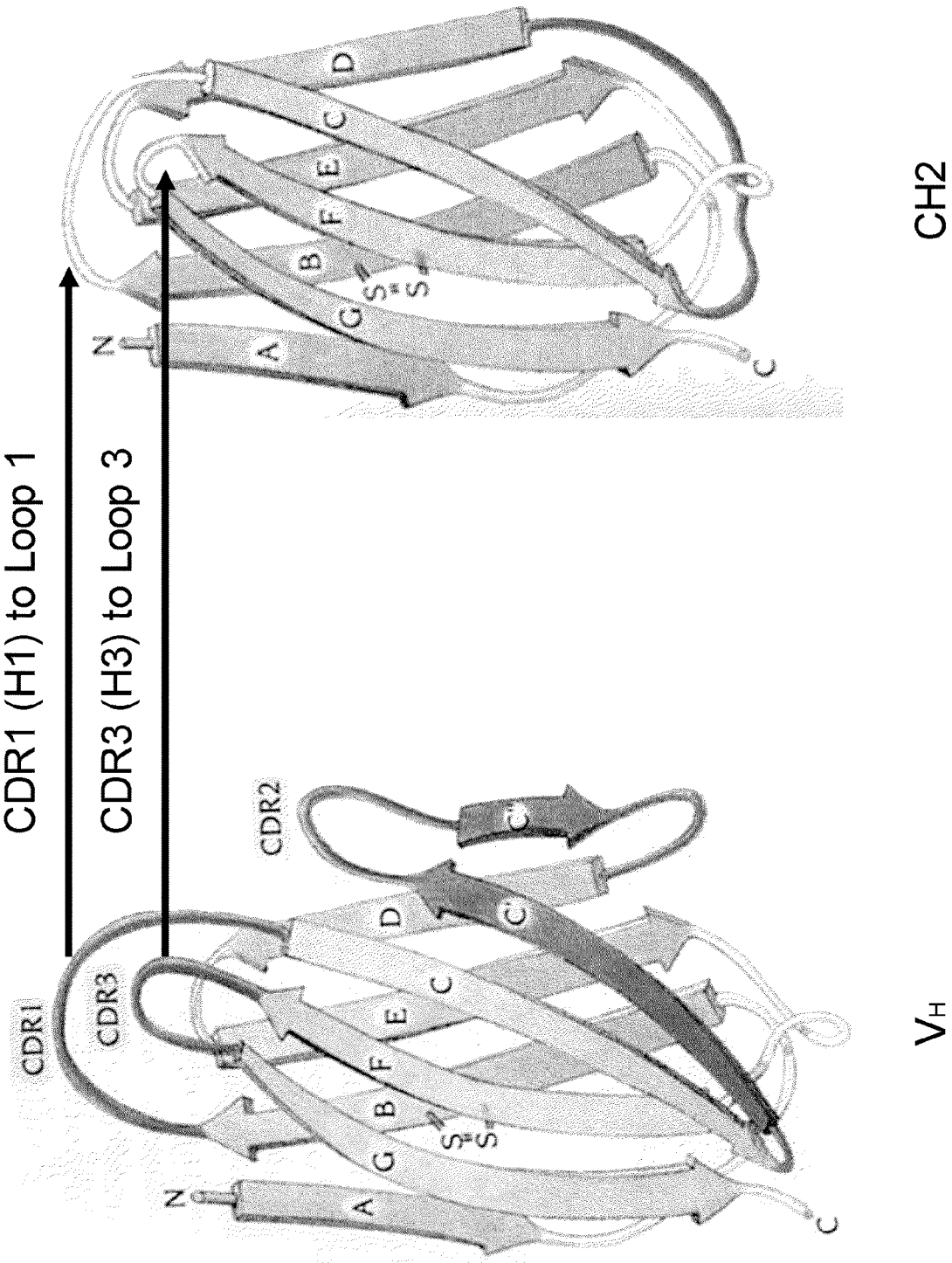

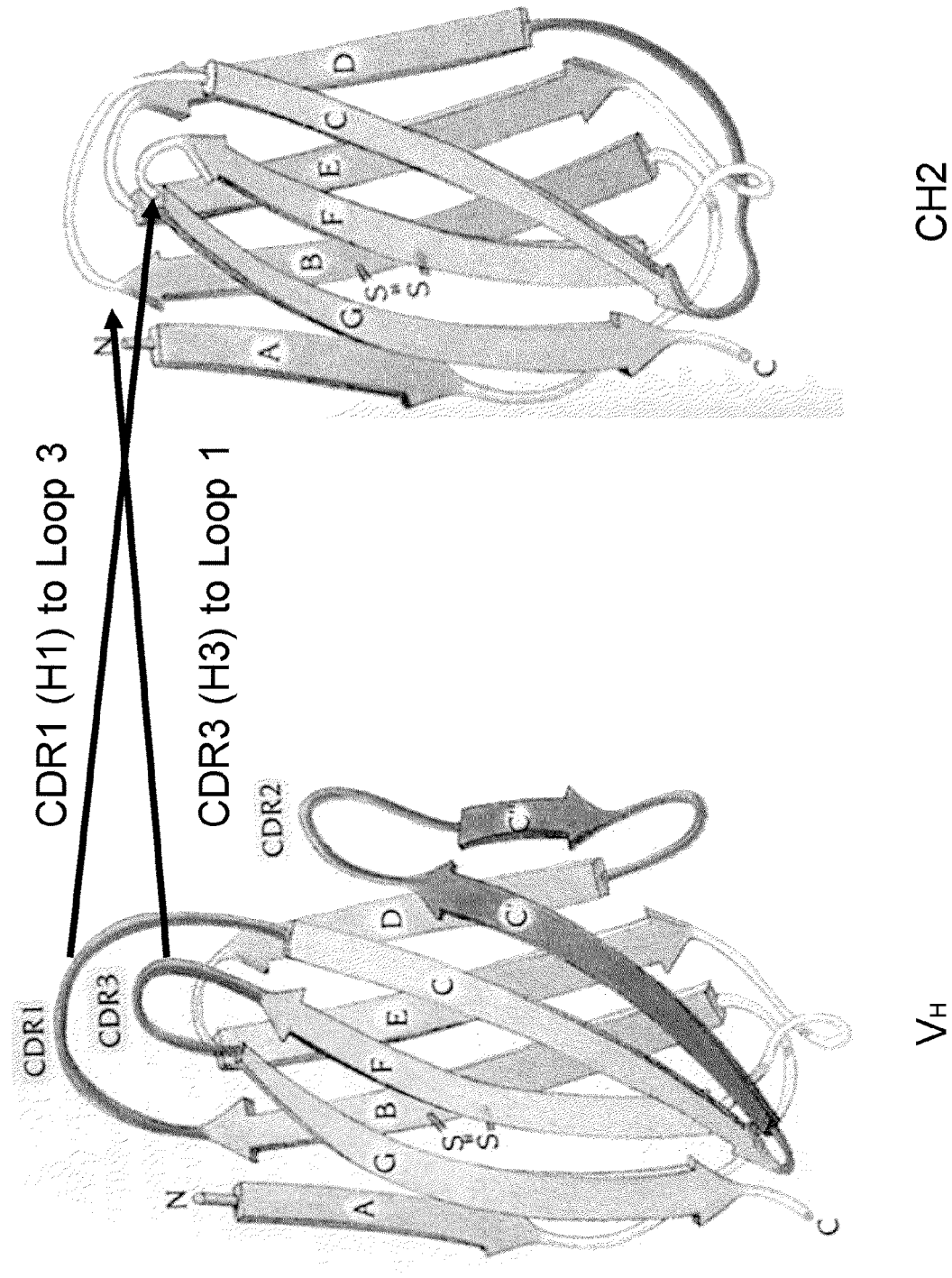

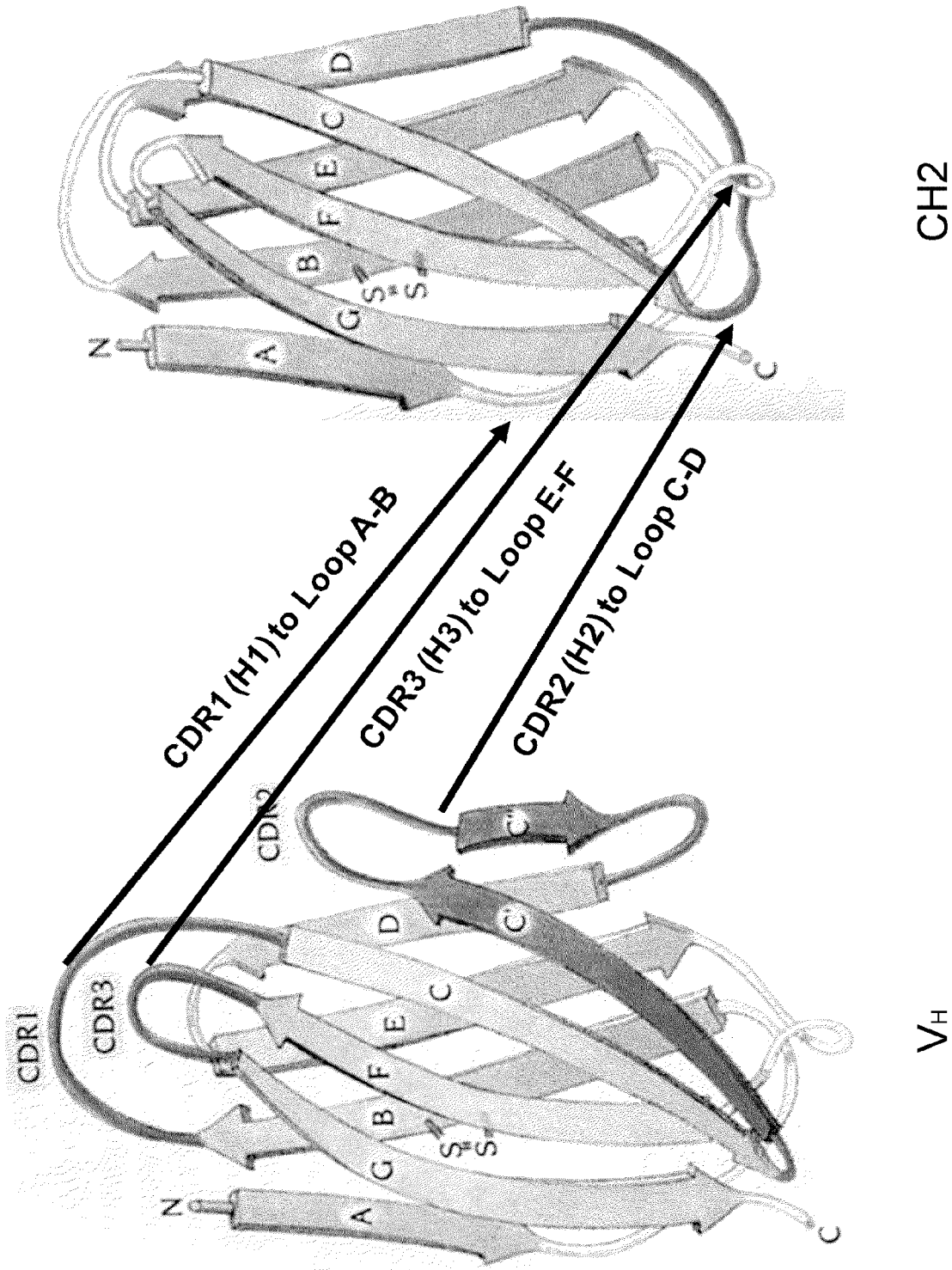

FIG. 5A

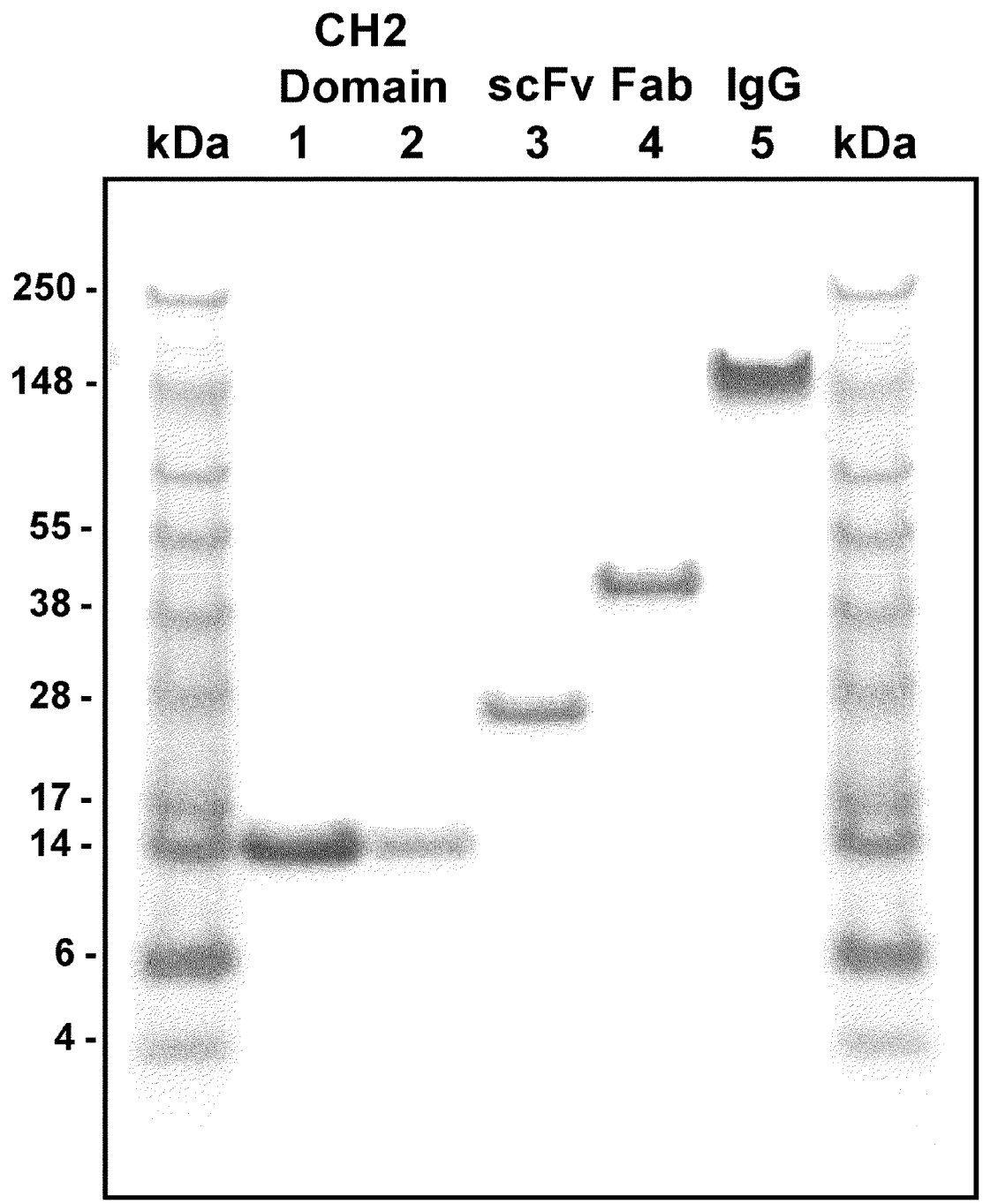

FIG. 13B
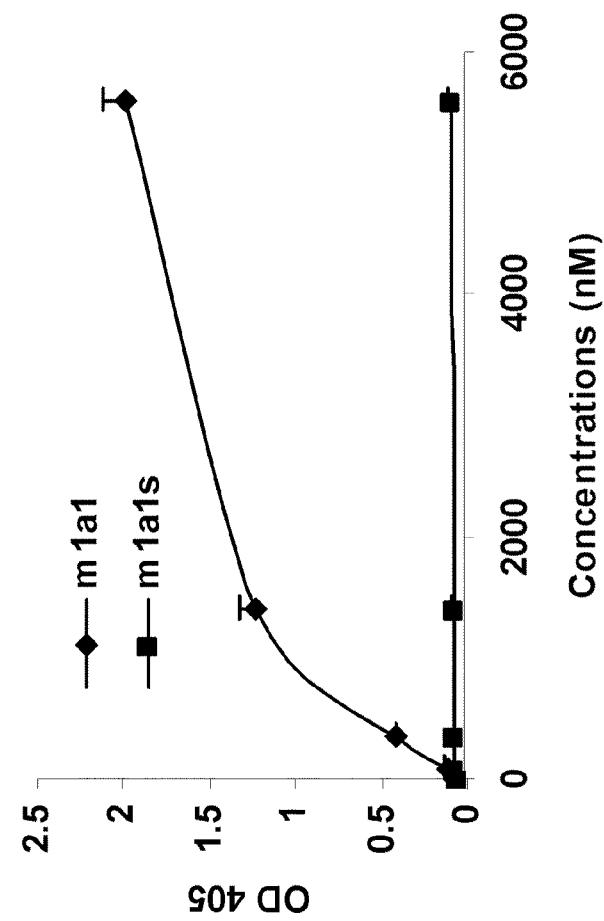
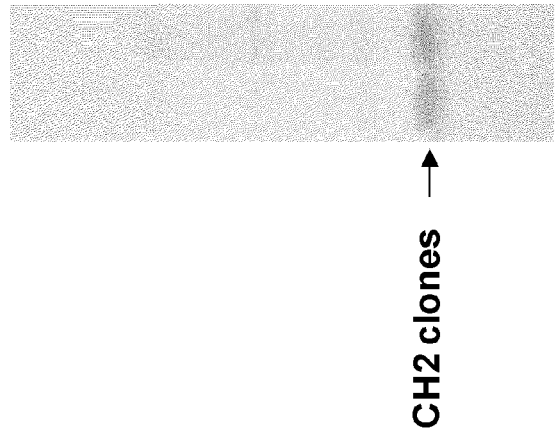

FIG. 15

Loop 2

CH2 sequence:    -- Q  Y  N  S  T  Y  R --  SEQ ID NO. 97

Library sequence: -- Q  Y (X  X  X) Y  R --  SEQ ID NO. 98

Loop 3

CH2 sequence:    -- S  N  K  A  L  P  A  P  I -- SEQ ID NO. 99

Library sequence: -- S  N (X  X  X  P  X) P  I -- SEQ ID NO. 100

X = N / T / I / D / A / V / S / Y / F

L2: CH2 ---NST---
    m1b3 ---ATD---

L3: CH2 ---KALPA---
    m1b3 ---TTAPT---

```
                        SEQUENCE LISTING

<160> NUMBER OF SEQ ID NOS: 113

<210> SEQ ID NO 1
<211> LENGTH: 129
<212> TYPE: PRT
<213> ORGANISM: Homo sapiens
<220> FEATURE:
<221> NAME/KEY: MISC_FEATURE
<222> LOCATION: (50)..(50)
<223> OTHER INFORMATION: X = any amino acid
<220> FEATURE:
<221> NAME/KEY: MISC_FEATURE
<222> LOCATION: (53)..(53)
<223> OTHER INFORMATION: X = any amino acid
<220> FEATURE:
<221> NAME/KEY: MISC_FEATURE
<222> LOCATION: (101)..(115)
<223> OTHER INFORMATION: X = any amino acid

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Xaa Ile Ser Xaa Lys Thr Asp Gly Gly Thr Tyr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Xaa Xaa Xaa Xaa Xaa Xaa Xaa Xaa Xaa Xaa Xaa Xaa
            100                 105                 110

Xaa Xaa Xaa Phe Asp Tyr Trp Gly Gln Gly Thr Leu Val Thr Val Ser
        115                 120                 125

Ser

<210> SEQ ID NO 2
<211> LENGTH: 118
<212> TYPE: PRT
<213> ORGANISM: Homo sapiens
```

<400> SEQUENCE: 2

His Val Gln Leu Gly Glu Ser Gly Gly Gly Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Arg Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Val Trp Ala Phe Asp Ile Trp Gly Gln Gly Thr
            100                 105                 110

Met Val Thr Val Ser Ser
        115

<210> SEQ ID NO 3
<211> LENGTH: 119
<212> TYPE: PRT
<213> ORGANISM: Homo sapiens

<400> SEQUENCE: 3

Gln Val Gln Lys Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Arg Gln Gln Leu Ser Asp Tyr Trp Gly Gln Gly
            100                 105                 110

Thr Leu Val Thr Val Ser Ser
        115

<210> SEQ ID NO 4
<211> LENGTH: 115
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr

```
                65                  70                  75                  80
Met Glu Leu Ser Ser Leu Arg Ser Glu Asp Thr Ala Val Tyr Tyr Cys
                        85                  90                  95

Ala Thr Pro Tyr Gly Met Asp Val Trp Gly Gln Gly Thr Thr Val Thr
                100                 105                 110

Val Ser Ser
        115

<210> SEQ ID NO 5
<211> LENGTH: 110
<212> TYPE: PRT
<213> ORGANISM: Homo sapiens

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 6
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 6
gcactggctg gtttcgctac cgtggcccag gcggccgcac ctgaactcct g            51

<210> SEQ ID NO 7
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 7
cacgtaccag ttgaacttgc cakmakmakm akmakmakma kmakmakmak mcaccaccac    60
gcatgtgac                                                           69

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
aagttcaact ggtacgtg                                                 18

<210> SEQ ID NO 9
```

-continued

```
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 9
gatggttttc tcgatggggc cakmakmakm akmakmakmg ttggagacct tgcacttg        58

<210> SEQ ID NO 10
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 10
ggtgcagaag atggtggtgg ccggcctggc ctttggcttt ggagatggtt ttctcgatg       59

<210> SEQ ID NO 11
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 11

Pro Glu Val Thr Cys Val Val Val Tyr Tyr Asp Ser Ala Ala Ala Tyr
1               5                   10                  15

Ala Tyr Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 12
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 12

Pro Glu Val Thr Cys Val Val Val Tyr Tyr Ser Ala Ser Ala Ala Ala
1               5                   10                  15

Ser Ala Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 13
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 13

Pro Glu Val Thr Cys Val Val Val Tyr Asp Ser Asp Tyr Ala Ser Ser
1               5                   10                  15

Asp Asp Gly Lys Phe Asn Trp Tyr Val Asp Gly Val Glu Val His Asn
            20                  25                  30

Ala Lys Thr Lys Pro Arg Lys Glu Gln Tyr Asn Ser Thr Tyr Arg
        35                  40                  45
```

```
<210> SEQ ID NO 14
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 14

Pro Glu Val Thr Cys Val Val Val Ala Tyr Ser Asp Ala Ala Ala
1               5                   10                  15

Tyr Asp Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 15
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 15

Pro Glu Val Thr Cys Val Val Val Asp Ala Asp Asp Asp Tyr Tyr Tyr
1               5                   10                  15

Tyr Tyr Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 16
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 16

Pro Glu Val Thr Cys Val Val Val Asp Asp Ala Tyr Tyr Asp Ala Asp
1               5                   10                  15

Tyr Tyr Tyr Gly Lys Phe Asn Trp Tyr Val Asp Gly Val Glu Val His
            20                  25                  30

Asn Ala Lys Thr Lys Pro Arg Glu Glu Gln Tyr Asn Ser Thr Tyr Arg
        35                  40                  45

<210> SEQ ID NO 17
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 17

Pro Glu Val Thr Cys Val Val Val Asp Ala Ala Tyr Asp Tyr Ser Tyr
1               5                   10                  15

Gly Lys Phe Asn Trp Tyr Val Asp Gly Val Glu Val His Asn Ala Lys
            20                  25                  30

Thr Lys Pro Arg Glu Glu Gln Tyr Asn Ser Thr Tyr Arg
        35                  40                  45

<210> SEQ ID NO 18
<211> LENGTH: 47
<212> TYPE: PRT
<213> ORGANISM: Artificial Sequence
```

```
<220> FEATURE:
<223> OTHER INFORMATION: Synthetic polypeptide

<400> SEQUENCE: 18

Pro Glu Val Thr Cys Val Val Val Asp Tyr Asp Ser Asp Ala Tyr
1               5                   10                  15

Ala Asp Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 19
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 19

Pro Glu Val Thr Cys Val Val Val Ser Tyr Tyr Asp Ser Asp Ser Tyr
1               5                   10                  15

Ser Ala Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 20
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 20

Pro Glu Val Thr Cys Val Val Val Asp Asp Ala Tyr Ala Asp Ala
1               5                   10                  15

Ser Ala Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 21
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 21

Pro Glu Val Thr Cys Val Val Val Ser Tyr Tyr Ser Asp Ser Asp Tyr
1               5                   10                  15

Asp Asp Gly Lys Phe Asn Trp Tyr Val Asp Gly Val Glu Val His Asn
            20                  25                  30

Ala Lys Thr Lys Pro Arg Glu Glu Gln Tyr Asn Ser Thr Tyr Arg
        35                  40                  45

<210> SEQ ID NO 22
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 22
```

```
Pro Glu Val Thr Cys Val Val Asp Asp Ser Tyr Tyr Ser Tyr
1               5                   10                  15

Asp Asp Gly Lys Phe Asn Trp Tyr Val Asp Gly Val Glu Val His Asn
                20                  25                  30

Ala Lys Thr Lys Pro Arg Glu Glu Gln Tyr Asn Ser Thr Tyr Arg
        35                  40                  45
```

<210> SEQ ID NO 23
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 23

```
Pro Glu Val Thr Cys Val Val Val Tyr Asp Ala Ser Asp Tyr Ala Asp
1               5                   10                  15

Ala Tyr Gly Lys Phe Asn Trp Tyr Val Asp Gly Val Glu Val His Asn
                20                  25                  30

Ala Lys Thr Lys Pro Arg Glu Glu Gln Tyr Asn Ser Thr Tyr Arg
        35                  40                  45
```

<210> SEQ ID NO 24
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 24

```
Pro Glu Val Thr Cys Val Val Val Ala Asp Ala Ala Ala Tyr Ala Tyr
1               5                   10                  15

Ala Asp Gly Lys Phe Asn Trp Tyr Val Asp Gly Val Glu Val His Asn
                20                  25                  30

Ala Lys Thr Lys Pro Arg Glu Glu Gln Tyr Asn Ser Thr Tyr Arg
        35                  40                  45
```

<210> SEQ ID NO 25
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 25

```
Pro Glu Val Thr Cys Val Val Val Ala Ser Asp Ser Ser Asp Asp Tyr
1               5                   10                  15

Asp Gly Lys Phe Asn Trp Tyr Val Asp Gly Val Glu Val His Asn Ala
                20                  25                  30

Lys Thr Lys Pro Arg Glu Glu Gln Tyr Asn Ser Thr Tyr Arg
        35                  40                  45
```

<210> SEQ ID NO 26
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 26

```
Pro Glu Val Thr Cys Val Val Val Ala Ala Ala Ala Ala Asp Ala Asp
1               5                   10                  15
```

```
Tyr Tyr Ser Lys Phe Asn Trp Tyr Val Asp Gly Val Glu Val His Asn
             20                  25                  30

Ala Lys Thr Lys Pro Arg Glu Glu Gln Tyr Asn Ser Thr Tyr Arg
         35                  40                  45
```

<210> SEQ ID NO 27
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 27

```
Pro Glu Val Thr Cys Val Val Val Tyr Asp Asp Ala Ala Tyr Ala Asp
1               5                   10                  15

Asp Tyr Gly Lys Phe Asn Trp Tyr Val Asp Gly Val Glu Val His Asn
             20                  25                  30

Ala Lys Thr Lys Pro Arg Glu Glu Gln Tyr Asn Ser Thr Tyr Arg
         35                  40                  45
```

<210> SEQ ID NO 28
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 28

```
Pro Glu Val Thr Cys Val Val Val Ser Ala Asp Ala Ser Asp Tyr Asp
1               5                   10                  15

Gly Lys Phe Asn Trp Tyr Val Asp Gly Val Glu Val His Asn Ala Asp
             20                  25                  30

Thr Lys Pro Arg Glu Glu Gln Tyr Asn Ser Thr Tyr Arg
         35                  40                  45
```

<210> SEQ ID NO 29
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 29

```
Pro Glu Val Thr Cys Val Val Val Asp Asp Asp Ala Ala Asp Ala Tyr
1               5                   10                  15

Tyr Tyr Gly Lys Phe Asn Trp Tyr Val Asp Gly Val Glu Val His Asn
             20                  25                  30

Ala Lys Thr Lys Pro Arg Glu Glu Gln Tyr Asn Ser Thr Tyr Arg
         35                  40                  45
```

<210> SEQ ID NO 30
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 30

```
Pro Glu Val Thr Cys Val Val Val Tyr Asp Ser Asp Asp Asp Tyr Asp
1               5                   10                  15

Tyr Ala Gly Lys Phe Cys Trp Tyr Val Asp Gly Val Glu Val His Asn
             20                  25                  30

Ala Lys Thr Lys Pro Arg Glu Glu His Tyr Asn Ser Thr Tyr Arg
```

-continued

```
            35                  40                  45
```

<210> SEQ ID NO 31
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 31

```
Val Val Ser Val Leu Thr Val Leu His Gln Asp Trp Leu Asn Gly Lys
1               5                   10                  15

Glu Tyr Lys Cys Lys Val Ser Asn Ala Ala Ser Ala Tyr Ser Gly Pro
            20                  25                  30

Ile Glu Lys Thr Ile Ser Lys Ala Lys
        35                  40
```

<210> SEQ ID NO 32
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 32

```
Val Val Ser Val Leu Thr Val Leu His Gln Asp Trp Leu Asn Gly Lys
1               5                   10                  15

Glu Tyr Lys Cys Lys Val Ser Asn Ala Asp Asp Ala Asp Ala Gly Pro
            20                  25                  30

Ile Glu Lys Thr Ile Ser Lys Ala Lys
        35                  40
```

<210> SEQ ID NO 33
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 33

```
Val Val Ser Val Leu Thr Val Leu His Gln Asp Trp Leu Asn Gly Lys
1               5                   10                  15

Glu Tyr Lys Cys Lys Val Ser Asn Ala Ala Asp Ala Tyr Ala Gly Pro
            20                  25                  30

Ile Glu Lys Thr Ile Ser Lys Ala Lys
        35                  40
```

<210> SEQ ID NO 34
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 34

```
Val Val Ser Val Leu Thr Val Leu His Gln Asp Trp Leu Asn Gly Lys
1               5                   10                  15

Glu Tyr Lys Cys Lys Val Ser Asn Ala Ala Asp Tyr Ser Asp Gly Pro
            20                  25                  30

Ile Glu Lys Thr Ile Ser Lys Ala Lys
        35                  40
```

<210> SEQ ID NO 35

```
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 35

Val Val Ser Val Leu Thr Val Leu His Gln Asp Trp Leu Asn Gly Lys
1               5                   10                  15

Glu Tyr Lys Cys Lys Val Ser Asn Ala Ala Asp Ala Ala Asp Gly Pro
            20                  25                  30

Ile Glu Lys Thr Ile Ser Lys Ala Lys
        35                  40

<210> SEQ ID NO 36
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 36

Val Val Ser Val Leu Thr Val Leu His Gln Asp Trp Leu Asn Gly Lys
1               5                   10                  15

Glu Tyr Lys Cys Lys Val Ser Asn Asp Ala Ser Ala Ser Ser Gly Pro
            20                  25                  30

Ile Glu Lys Thr Ile Ser Lys Ala Lys
        35                  40

<210> SEQ ID NO 37
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 37

Val Val Ser Val Leu Thr Val Leu His Gln Asp Trp Leu Asn Gly Lys
1               5                   10                  15

Glu Tyr Lys Cys Lys Val Ser Asn Asp Asp Tyr Ala Ala Ser Gly Pro
            20                  25                  30

Ile Glu Lys Thr Ile Ser Lys Ala Lys
        35                  40

<210> SEQ ID NO 38
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 38

Val Val Ser Val Leu Thr Val Leu His Gln Asp Trp Leu Asn Gly Lys
1               5                   10                  15

Glu Tyr Lys Cys Lys Val Ser Asn Asp Ala Tyr Ala Ser Asp Gly Pro
            20                  25                  30

Ile Glu Lys Thr Ile Ser Lys Ala Lys
        35                  40

<210> SEQ ID NO 39
<211> LENGTH: 41
<212> TYPE: PRT
<213> ORGANISM: Artificial Sequence
<220> FEATURE:
```

<223> OTHER INFORMATION: Synthetic polypeptide

<400> SEQUENCE: 39

Val Val Ser Val Leu Thr Val Leu His Gln Asp Trp Leu Asn Gly Lys
1               5                   10                  15

Glu Tyr Lys Cys Lys Val Ser Asn Asp Ala Asp Ala Ser Gly Pro
            20                  25                  30

Ile Glu Lys Thr Ile Ser Lys Ala Lys
        35                  40

<210> SEQ ID NO 40
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 40

Val Val Ser Val Leu Thr Val Leu His Gln Asp Trp Leu Asn Gly Lys
1               5                   10                  15

Glu Tyr Lys Cys Lys Val Ser Asn Ala Ala Asp Asp Ser Gly Pro
            20                  25                  30

Ile Glu Lys Thr Ile Ser Lys Ala Lys
        35                  40

<210> SEQ ID NO 41
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 41

Val Val Ser Val Leu Thr Val Leu His Gln Asp Trp Leu Asn Gly Lys
1               5                   10                  15

Glu Tyr Lys Cys Lys Val Ser Asn Ala Asp Ala Tyr Ala Tyr Gly Pro
            20                  25                  30

Ile Glu Lys Thr Ile Ser Lys Ala Lys
        35                  40

<210> SEQ ID NO 42
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 42

Val Val Ser Val Leu Thr Val Leu His Gln Asp Trp Leu Asn Gly Lys
1               5                   10                  15

Glu Tyr Lys Cys Lys Val Ser Asn Ala Asp Asp Tyr Asp Tyr Gly Pro
            20                  25                  30

Ile Glu Lys Thr Ile Ser Lys Ala Lys
        35                  40

<210> SEQ ID NO 43
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 43

-continued

```
Val Val Ser Val Leu Thr Val Leu His Gln Asp Trp Leu Asn Gly Lys
1               5                   10                  15

Glu Tyr Lys Cys Lys Val Ser Asn Tyr Ser Asp Ser Ala Ala Gly Pro
            20                  25                  30

Ile Glu Lys Thr Ile Ser Lys Ala Lys
        35                  40

<210> SEQ ID NO 44
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 44

Val Val Ser Val Leu Thr Val Leu His Gln Asp Trp Leu Asn Gly Lys
1               5                   10                  15

Glu Tyr Lys Cys Lys Val Ser Asn Tyr Ala Ala Ser Ala Tyr Gly Pro
            20                  25                  30

Ile Glu Lys Thr Ile Ser Lys Ala Lys
        35                  40

<210> SEQ ID NO 45
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 45

Val Val Ser Val Leu Thr Val Leu His Gln Asp Trp Leu Asn Gly Lys
1               5                   10                  15

Glu Tyr Lys Cys Lys Val Ser Asn Tyr Asp Asp Asp Ala Asp Gly Pro
            20                  25                  30

Ile Glu Lys Thr Ile Ser Lys Ala Lys
        35                  40

<210> SEQ ID NO 46
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 46

Val Val Ser Val Leu Thr Val Leu His Gln Asp Trp Leu Asn Gly Lys
1               5                   10                  15

Glu Tyr Lys Cys Lys Val Ser Asn Tyr Tyr Asp Tyr Asp Tyr Gly Pro
            20                  25                  30

Ile Glu Lys Thr Ile Ser Lys Ala Lys
        35                  40

<210> SEQ ID NO 47
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 47

Val Val Ser Val Leu Thr Val Leu His His Asp Trp Met Asn Gly Lys
1               5                   10                  15

Glu Tyr Lys Cys Glu Val Ser Asn Asp Ala Asp Ser Ala Asp Gly Pro
```

-continued

```
                20                  25                  30

Ile Lys Lys Thr Ile Ser Lys Ala Lys
        35                  40

<210> SEQ ID NO 48
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 48

Val Val Ser Val Leu Thr Val Leu His His Asp Trp Leu Asn Gly Glu
1               5                   10                  15

Glu Tyr Lys Cys Lys Val Ser Asn Asp Ala Ser Asp Asp Ala Gly Pro
                20                  25                  30

Ile Glu Lys Thr Ile Ser Ala Lys
        35                  40

<210> SEQ ID NO 49
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 49

Val Val Ser Val Leu Thr Val Leu His Gln Asp Trp Leu Asn Gly Lys
1               5                   10                  15

Glu Tyr Lys Cys Lys Val Ser Asn Ala Asp Asp Ala Tyr Ala Gly Pro
                20                  25                  30

Ile Glu Lys Thr Ile Ser Lys Ala Lys
        35                  40

<210> SEQ ID NO 50
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 50

Val Val Ser Val Leu Thr Val Leu His His Tyr Trp Met Asn Gly Glu
1               5                   10                  15

Asp Tyr Lys Cys Glu Val Ser Asn Asp Ser Tyr Ser Asp Gly Pro
                20                  25                  30

Ile Lys Lys Thr Ile Ser Lys Ala Lys
        35                  40

<210> SEQ ID NO 51
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 51
tagcgattcg ctaccgtggc ccaggcggcc cctgaactcc tgggggggacc                50

<210> SEQ ID NO 52
<211> LENGTH: 21
<212> TYPE: DNA
<213> ORGANISM: Artificial Sequence
<220> FEATURE:
```

<223> OTHER INFORMATION: Synthetic oligonucleotide

<400> SEQUENCE: 52 tcccccagg agttcaggtg c                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
tgcgtggtgg tggacgtgag c                                             21

<210> SEQ ID NO 54
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 54
taggcatgca tctgcatggt ggccggcctg gcctttggct ttggagatgg ttttctcgat    60
gg                                                                  62

<210> SEQ ID NO 55
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 55
gaactcctgg ggggaccggc yayrtattac tgtgyg                             36

<210> SEQ ID NO 56
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 56
gaactcctgg ggggaccggc yttrtattac tgtgyg                             36

<210> SEQ ID NO 57
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 57
gaactcctgg ggggaccggc ygtrtattac tgtgyg                             36

<210> SEQ ID NO 58
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 58
gctcacgtcc accaccacgc aggtgccctg gcccca                             36

<210> SEQ ID NO 59
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 59
gctcacgtcc accaccacgc aggtgccacg gcccca                          36

<210> SEQ ID NO 60
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 60
gctcacgtcc accaccacgc aggtgccayg gcccca                          36

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 61
gtacgtgctg ttgtactgct c                                          21

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 62
aaggtctcca acaaagccct c                                          21

<210> SEQ ID NO 63
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 63
gagcagtaca acagcacgta cgcagcyayr tattactgtg yg                    42

<210> SEQ ID NO 64
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 64
gagcagtaca acagcacgta cgcagcyttr tattactgtg yg                    42

<210> SEQ ID NO 65
<211> LENGTH: 42
<212> TYPE: DNA
<213> ORGANISM: Artificial Sequence
<220> FEATURE:
<223> OTHER INFORMATION: Synthetic oligonucleotide

```
<400> SEQUENCE: 65
gagcagtaca acagcacgta cgcagcygtr tattactgtg yg                    42

<210> SEQ ID NO 66
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 66
gagggctttg ttggagacct tggttccctg gcccca                          36

<210> SEQ ID NO 67
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 67
gagggctttg ttggagacct tggtgccacg gcccca                          36

<210> SEQ ID NO 68
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 68
gagggctttg ttggagacct tggtgccayg gcccca                          36

<210> SEQ ID NO 69
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 69

Ala Val Tyr Tyr Cys Val Lys Val Pro Val Gly Tyr Trp Gly Arg Gly
1               5                   10                  15
Thr Ala Val Tyr Tyr Cys Ala Asp Val Glu Ala Ser Ser Pro Ala Asp
            20                  25                  30
Phe Gly Tyr Trp Gly Arg Gly Thr
        35                  40

<210> SEQ ID NO 70
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 70

Ala Met Tyr Tyr Cys Ala Arg Asp His Gly Val Asp Thr Ala Met Ala
1               5                   10                  15
Gly Pro Trp Phe Asp Tyr Trp Gly Arg Gly Thr Ala Val Tyr Tyr Cys
            20                  25                  30
Val Arg Gly Thr Gly Trp Glu Leu Leu Val Ile Asp Cys Trp Gly Arg
        35                  40                  45
Gly Thr
    50
```

<210> SEQ ID NO 71
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 71

```
Ala Val Tyr Tyr Cys Ala Arg Gly Ser Ser Gly Trp Gly Trp Phe Asp
1               5                   10                  15

Pro Trp Gly Gln Gly Thr Ala Thr Tyr Tyr Cys Ala Arg Asp Arg Gly
            20                  25                  30

Tyr Trp Gly Arg Gly Thr
        35
```

<210> SEQ ID NO 72
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 72

```
Ala Val Tyr Tyr Cys Ala Arg Arg Met Pro Glu Gly Asp Ser Ser Gly
1               5                   10                  15

Thr Ser Tyr Tyr Phe Asp Tyr Trp Gly Gln Gly Thr Ala Leu Tyr Tyr
            20                  25                  30

Cys Ala Arg Glu Glu Lys Gly Asp Tyr Asp Tyr Trp Gly Gln Gly Thr
        35                  40                  45
```

<210> SEQ ID NO 73
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 73

```
Ala Met Tyr Tyr Cys Ala Ile His Ser Phe Asp Tyr Trp Gly Gln Gly
1               5                   10                  15

Thr Ala Val Tyr Tyr Cys Ala Lys Val Leu Ser Gly Trp Phe Asp His
            20                  25                  30

Tyr Phe Asp Ser Trp Gly Gln Gly Thr
        35                  40
```

<210> SEQ ID NO 74
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 74

```
Ala Val Tyr Tyr Cys Ala Arg Asp Arg Val Pro Asp Gly Val Trp Ser
1               5                   10                  15

Ala Asp Ser Trp Gly Gln Gly Thr Ala Val Tyr Tyr Cys Ala Ser Lys
            20                  25                  30

Pro Pro Val Ser Asn Trp Phe Asp Pro Trp Gly Gln Gly Thr
        35                  40                  45
```

<210> SEQ ID NO 75
<211> LENGTH: 43

```
<212> TYPE: PRT
<213> ORGANISM: Artificial Sequence
<220> FEATURE:
<223> OTHER INFORMATION: Synthetic polypeptide

<400> SEQUENCE: 75

Ala Ile Tyr Tyr Cys Val Lys Ala Gly Tyr Asn Phe Asp Ala Phe Asp
1               5                   10                  15

His Trp Gly Arg Gly Thr Ala Met Tyr Tyr Cys Ala Gly Asp Thr Ala
            20                  25                  30

Met Val Ile Phe Asp Tyr Trp Gly Gln Gly Thr
        35                  40

<210> SEQ ID NO 76
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 76

Ala Thr Tyr Tyr Cys Ala Ser Gly Ser Gly Cys Ser Asp Tyr Trp
1               5                   10                  15

Gly Gln Gly Thr Ala Thr Tyr Tyr Cys Ala Arg Gly Gly Tyr Ser Ser
            20                  25                  30

Gly Trp Tyr His Trp Tyr Phe Asp Leu Trp Gly Arg Gly Thr
        35                  40                  45

<210> SEQ ID NO 77
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 77

Ala Val Tyr Tyr Cys Ala Ala Ser Val Gly Ala Pro Ser Asp Phe Asp
1               5                   10                  15

Tyr Trp Gly Gln Gly Thr Ala Thr Tyr Tyr Cys Ala Thr Thr Pro Asp
            20                  25                  30

Ser Asn Tyr Gly Tyr Trp Gly Gln Gly Thr
        35                  40

<210> SEQ ID NO 78
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 78

Ala Leu Tyr Tyr Cys Ala Lys Gly Gln Tyr Gly Asp His Asp Tyr Trp
1               5                   10                  15

Gly Gln Gly Thr Ala Val Tyr Tyr Cys Ala Lys Glu Glu Glu Gly Ala
            20                  25                  30

Val Leu Gly Trp Gly Arg Gly Thr
        35                  40

<210> SEQ ID NO 79
<211> LENGTH: 47
<212> TYPE: PRT
<213> ORGANISM: Artificial Sequence
<220> FEATURE:
<223> OTHER INFORMATION: Synthetic polypeptide
```

-continued

<400> SEQUENCE: 79

Ala Thr Tyr Tyr Cys Ala Arg Glu Gly Thr Val Val Thr Pro Tyr Phe
1               5                   10                  15

Val Tyr Trp Gly Gln Gly Thr Ala Val Tyr Tyr Cys Ala Met Gly Gly
            20                  25                  30

His Gly Ser Gly Ser Tyr Leu Ser Gly Tyr Trp Gly Gln Gly Thr
        35                  40                  45

<210> SEQ ID NO 80
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 80

Ala Val Tyr Tyr Cys Ala Arg Glu Arg Tyr Gly Ala Leu Asp Tyr Trp
1               5                   10                  15

Gly Arg Gly Thr Ala Val Tyr Tyr Cys Ala Gly Gly Leu Leu His Glu
            20                  25                  30

Gly Ser Gly Tyr Trp Gly Gln Gly Thr
        35                  40

<210> SEQ ID NO 81
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 81

Ala Ile Tyr Tyr Cys Ala Ala Arg Gly Gln Gly Asn Ser Trp Trp Phe
1               5                   10                  15

Asp Pro Trp Gly Gln Gly Thr Ala Ile Tyr Tyr Cys Ala Thr Gln Val
            20                  25                  30

Gly His Gly Asp Trp Gly Gln Gly Thr
        35                  40

<210> SEQ ID NO 82
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 82

Ala Leu Tyr Tyr Cys Ala Arg Ala Tyr Ser Ala Tyr Gln Tyr Ser Phe
1               5                   10                  15

Asp Ser Trp Gly Arg Gly Thr Ala Val Tyr Tyr Cys Ala Arg Arg Glu
            20                  25                  30

Tyr Asn Trp Asn His Asn Trp Phe Asp Pro Trp Gly Gln Gly Thr
        35                  40                  45

<210> SEQ ID NO 83
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 83

Ala Thr Tyr Tyr Cys Ala Arg Arg Gly Asp Asp Tyr Gly Asp Tyr Phe

```
                  1               5              10              15
Phe Asp Tyr Trp Gly Gln Gly Thr Ala Ile Tyr Tyr Cys Ala Arg Ser
                       20                  25                  30

Arg Gly Ser Ser Phe Asp Tyr Trp Gly Gln Gly Thr
            35                  40

<210> SEQ ID NO 84
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 84

Ala Met Tyr Tyr Cys Ala Arg Asp Leu Tyr Ser Asn Tyr Val Asp Tyr
1               5                  10                  15

Trp Gly Gln Gly Thr Ala Val Tyr Tyr Cys Ala Arg Gly Pro Trp Gln
                20                  25                  30

Gln Leu Val Asn Trp Phe Asp Pro Trp Gly Gln Gly Thr
            35                  40                  45

<210> SEQ ID NO 85
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 85

Ala Thr Tyr Tyr Cys Ala Ser Leu Thr Gly Thr Thr Ser Tyr Trp Gly
1               5                  10                  15

Gln Gly Thr Ala Leu Tyr Tyr Cys Ala Arg Ala Thr Gly Tyr Gln
                20                  25                  30

Phe Asp Cys Trp Gly Gln Gly Thr
            35                  40

<210> SEQ ID NO 86
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 86

Ala Ile Tyr Tyr Cys Ala Arg Glu Ser Ser Ser Phe Asp Tyr Trp
1               5                  10                  15

Gly Gln Gly Thr Ala Val Tyr Tyr Cys Ala Arg Met Ser Gly Gly Arg
                20                  25                  30

Trp Ile Phe Asp His Trp Gly Gln Gly Thr
            35                  40

<210> SEQ ID NO 87
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 87

Ala Val Tyr Tyr Cys Ala Arg Gly Trp Glu Leu Asp Tyr Trp Gly Gln
1               5                  10                  15

Gly Thr Ala Val Tyr Tyr Cys Ala Lys Thr Gly Gln Phe Asp Tyr Trp
                20                  25                  30
```

```
Gly Gln Gly Thr
        35

<210> SEQ ID NO 88
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 88

Gly Pro Ser Val Phe Leu Phe Pro Pro Lys Pro Lys Asp Thr Leu
1               5                   10                  15

<210> SEQ ID NO 89
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 89

Glu Lys Thr Ile Ser Lys Ala Lys
1               5

<210> SEQ ID NO 90
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 90

Gly Pro Ser Val Phe Leu Phe Pro Pro Lys Pro Lys Asp Thr Leu
1               5                   10                  15

<210> SEQ ID NO 91
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 91

Glu Lys Thr Ile Ser Lys Ala Lys
1               5

<210> SEQ ID NO 92
<211> LENGTH: 107
<212> TYPE: PRT
<213> ORGANISM: Mus musculus

<400> SEQUENCE: 92

Val Pro Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
            20                  25                  30

Ile Ser Lys Asp Asp Pro Glu Val Gln Phe Ser Trp Phe Val Asp Asp
        35                  40                  45

Val Glu Val His Thr Ala Gln Thr Gln Pro Arg Glu Glu Gln Phe Asn
    50                  55                  60

Ser Thr Phe Arg Ser Val Ser Glu Leu Pro Ile Met His Gln Asp Trp
65                  70                  75                  80

Leu Asn Gly Lys Glu Phe Lys Cys Arg Val Asn Ser Ala Ala Phe Pro
```

```
                85                  90                  95
Ala Pro Ile Glu Lys Thr Ile Ser Lys Thr Lys
            100                 105

<210> SEQ ID NO 93
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 93

Val Val Val Asp Val Ser His Glu Asp Pro Glu Val Lys Phe Asn
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(13)
<223> OTHER INFORMATION: X = Tyr, Ala, Asp or Ser

<400> SEQUENCE: 94

Val Val Val Xaa Xaa Xaa Xaa Xaa Xaa Xaa Xaa Xaa Xaa Gly Lys Phe
1               5                   10                  15

Asn

<210> SEQ ID NO 95
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 95

Val Ser Asn Lys Ala Leu Pro Ala Pro Ile Glu
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(9)
<223> OTHER INFORMATION: X = Tyr, Ala, Asp or Ser

<400> SEQUENCE: 96

Val Ser Asn Xaa Xaa Xaa Xaa Xaa Xaa Gly Pro Ile Glu
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 97

Gln Tyr Asn Ser Thr Tyr Arg
1               5
```

```
<210> SEQ ID NO 98
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(5)
<223> OTHER INFORMATION: X = Asn, Thr, Ile, Asp, Ala, Val, Ser, Tyr or
      Phe

<400> SEQUENCE: 98

Gln Tyr Xaa Xaa Xaa Tyr Arg
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 99

Ser Asn Lys Ala Leu Pro Ala Pro Ile
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(5)
<223> OTHER INFORMATION: X = Asn, Thr, Ile, Asp, Ala, Val, Ser, Tyr or
      Phe
<220> FEATURE:
<221> NAME/KEY: MISC_FEATURE
<222> LOCATION: (7)..(7)
<223> OTHER INFORMATION: X = Asn, Thr, Ile, Asp, Ala, Val, Ser, Tyr or
      Phe

<400> SEQUENCE: 100

Ser Asn Xaa Xaa Xaa Pro Xaa Pro Ile
1               5

<210> SEQ ID NO 101
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 101
acgtggccca ggcggccgca cctgaactcc tg                                    32

<210> SEQ ID NO 102
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 102
acgtggccgg cctggccttt ggctttggag atggttttct cgatg                      45

<210> SEQ ID NO 103
```

```
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 103
gctgaccaca cggtaadhad hadhgtactg ctcctcccg                            39

<210> SEQ ID NO 104
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 104
taccgtgtgg tcagc                                                     15

<210> SEQ ID NO 105
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 105
ggagatggtt ttctcgatgg gadhtggadh adhadhgttg gagaccttgc a              51

<210> SEQ ID NO 106
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 106

Asp Tyr Asp Tyr Asp Ser Tyr Phe Asp Phe Gly
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 107

Asp Tyr Asp Tyr Asp Ser Tyr Phe Asp Phe Gly
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 108

Asp Tyr Asp Tyr Asp Ser Tyr Tyr Asp Gly
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic polypeptide
```

```
<400> SEQUENCE: 109

Asp Tyr Asp Tyr Asp Ser Tyr Tyr Asp Tyr Gly
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 110

Ser Asp Ser Ala Ala Ser Gly
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 111

Asp Asp Tyr Ala Ala Asp Gly
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 112

Tyr Asp Tyr Ala Asp Asp Gly
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 113

Ser Asp Tyr Asp Ser Ser Gly
1               5
```

ENGINEERED ANTIBODY CONSTANT DOMAIN MOLECULES

CROSS REFERENCE TO RELATED APPLICATIONS

This is the U.S. National Stage of International Application No. PCT/US2009/032692 filed Jan. 30, 2009, published in English under PCT Article 21(2), which claims the benefit of U.S. Provisional Application No. 61/063,245, filed Jan. 31, 2008, which is herein incorporated by reference in its entirety.

FIELD

This relates to antibodies, specifically to antibody constant domains mutated at specific positions and/or engrafted with one or more variable chain loops from a heterologous antibody that specifically bind an antigen of interest.

BACKGROUND

Conventional antibodies are large multi-subunit protein complexes comprising at least four polypeptide chains, including two light chains and two heavy chains. The heavy and light chains of antibodies contain variable (V) regions, which bind antigen, and constant (C) regions, which provide structural support and effector functions. The antigen binding region comprises two separate domains, a heavy chain variable domain ($V_H$) and a light chain variable domain ($V_L$). Complementarity determining regions (CDRs), short amino acid sequences in the variable domains of an antibody, provide antigen specificity. The heavy and light chains of an antibody molecule each provide three CDRs (CDR1, CDR2 and CDR3), therefore there are six CDRs for each antibody that can come into contact with the antigen, resulting in the antigen specificity.

A typical antibody, such as an IgG molecule, has a molecular weight of approximately 150 kD. Therapeutic use can be limited due to the relatively large size of an antibody, which can restrict tissue penetration or epitope access.

A number of smaller antigen binding fragments of naturally occurring antibodies have been identified following protease digestion (for example, Fab, Fab', and $F(ab')_2$). These antibody fragments have a molecular weight ranging from approximately 50 to 100 kD. Recombinant methods have been used to generate alternative antigen-binding fragments, termed single chain variable fragments (scFv), which consist of $V_L$ and $V_H$ joined by a synthetic peptide linker. A scFv molecule has a molecular weight of approximately 25-30 kD.

While the antigen binding unit of a naturally-occurring antibody in humans and most other mammals is generally known to be comprised of a pair of variable regions, camelid species express a large proportion of fully functional, highly specific antibodies that are devoid of light chain sequences. The camelid heavy chain antibodies exist as homodimers of a single heavy chain, dimerized via their constant regions (U.S. Pat. Nos. 5,840,526 and 6,838,254; and U.S. Patent Application Publication No. 2003-0088074). The variable domains of these camelid heavy chain antibodies, referred to as $V_H$H domains, retain the ability, when isolated as fragments of the $V_H$ chain, to bind antigen with high specificity (Hamers-Casterman et al. *Nature* 363:446-448, 1993; Gahroudi et al. *FEBS Lett.* 414:521-526, 1997).

Antigen binding single $V_H$ domains, called domain antibodies (dAb), have also been identified from a library of murine $V_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609).

However, a need remains for very small antibodies that can specifically bind antigen. Such small molecules could provide increased epitope access, better tissue penetration and could be used for any diagnostic or therapeutic application that utilizes antibodies or their fragments.

SUMMARY

This disclosure concerns engineered antibody constant domain molecules. In one embodiment, the antibody constant domain is a CH2 domain from IgG, IgA or IgD. In another embodiment, the antibody constant domain is a CH3 domain from IgE or IgM. As described herein, the CH2 or CH3 domain molecules are small, stable, soluble, have minimal to no toxicity and effectively bind antigen. Thus, provided herein are polypeptides comprising an immunoglobulin CH2 or CH3 domain, wherein at least one of the loops of the CH2 or CH3 domains is mutated, or at least a portion of a loop region of the CH2 or CH3 domain is replaced by a complementarity determining region (CDR), or a functional fragment thereof (such as one containing specificity-determining residues (SDR)), from a heterologous immunoglobulin variable domain, or both. The CH2 and CH3 domain molecules described herein have a molecular weight of less than about 15 kD. Also provided herein are compositions, libraries and kits comprising the CH2 or CH3 domain molecules, and methods of use. Further provided are recombinant constant domains exhibiting increased stability that can be used as scaffolds for the construction of antigen binding CH2 or CH3 domains. Methods of identifying recombinant CH2 or CH3 domains that specifically bind antigen and methods of generating libraries comprising recombinant CH2 or CH3 domains are also provided.

The foregoing and other features and advantages will become more apparent from the following detailed description of several embodiments, which proceeds with reference to the accompanying figures.

BRIEF DESCRIPTION OF THE FIGURES

FIG. 1A is a schematic drawing of an immunoglobulin molecule. Conventional antibodies are large multi-subunit protein complexes comprising at least four polypeptide chains, including two light (L) chains and two heavy (H) chains. The heavy and light chains of antibodies contain variable (V) regions, which bind antigen, and constant (C) regions (such as CH1, CH2 and CH3 domains), which provide structural support and effector functions. The antigen binding region comprises two separate domains, a heavy chain variable domain ($V_H$) and a light chain variable domain ($V_L$).

FIG. 1B shows the consensus amino acid sequence of a human heavy chain variable domain (SEQ ID NO: 1). The locations of CDR1, CDR2, CDR3 (denoted H1, H2 and H3) are indicated. Also shown are the amino acid sequences of the heavy chain of three different antigen-specific human antibodies (SEQ ID NOs: 2-4). The numbers shown are based on the Kabat numbering system (Wu and Kabat, *J. Exp. Med.* 132(2):211-250, 1970).

FIG. 2 shows the amino acid sequence of the human γ1 CH2 domain (SEQ ID NO: 5). Residues in regions of β-sheet (. . . ) and α-helices (***) are indicated. The locations of Loop B-C (here denoted as Loop 1), Loop D-E (here denoted as Loop 2), Loop F-G (here denoted as Loop 3), Loop A-B, Loop C-D and Loop E-F are also shown. Residues in each loop are shown in bold.

FIGS. 3A-3C are schematic drawings illustrating potential strategies for grafting CDRs (or hypervariable loops) on CH2 domains.

Figure 5A:
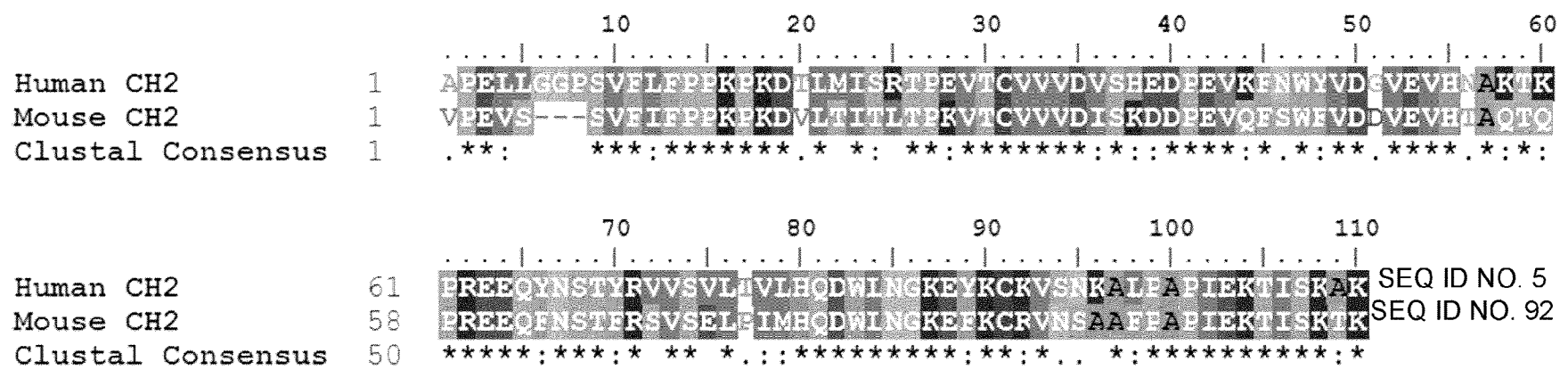
Figure 5B:
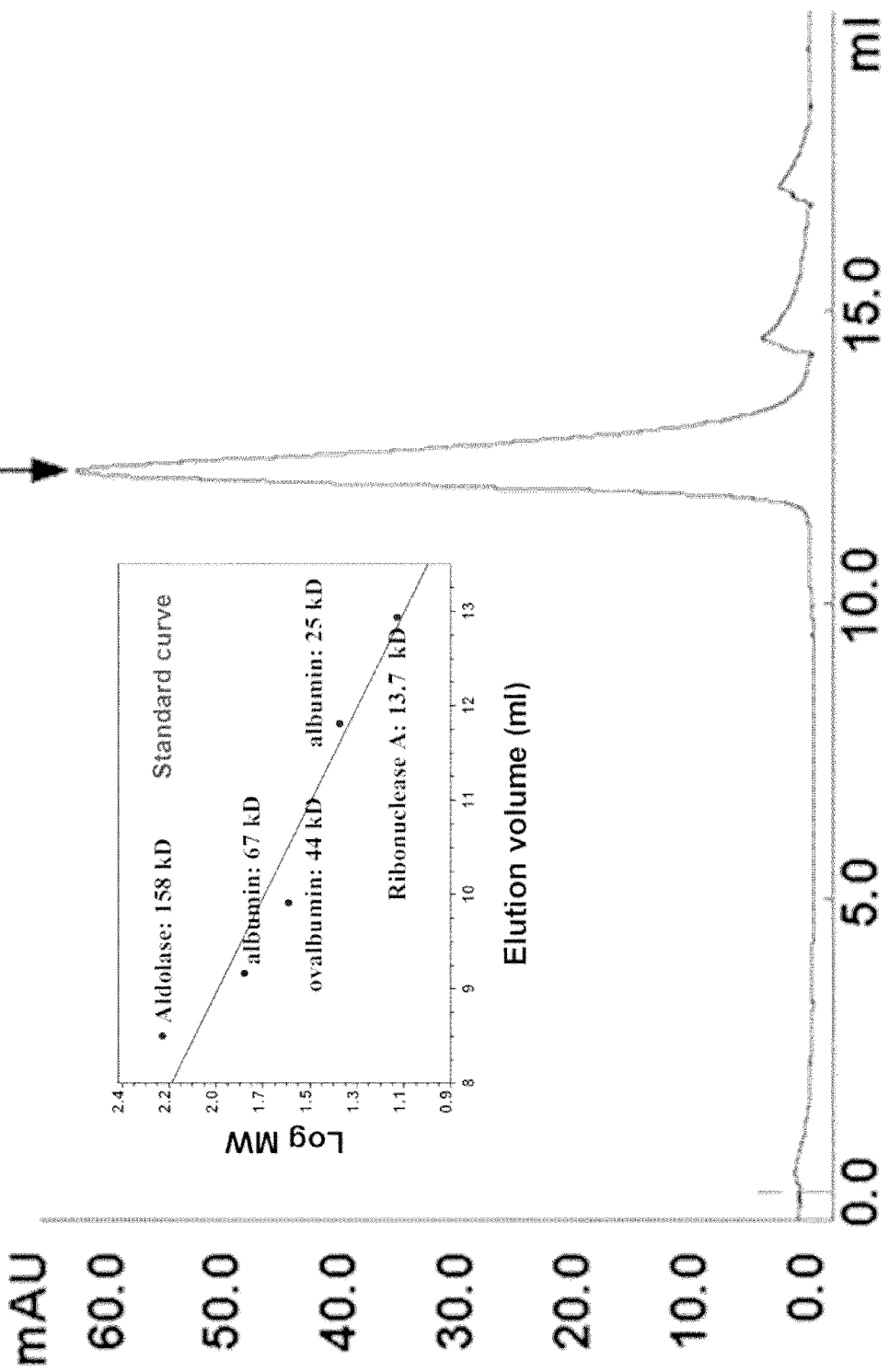

FIG. 5A shows an amino acid sequence alignment of human CH2 (NCBI Accession No. J00228; SEQ ID NO: 5) and mouse CH2 (NCB Accession No. J00453; SEQ ID NO: 92). Identical and similar residues were 67% and 92%, respectively. FIG. 5B is a graph showing size exclusion chromatography of human CH2. The inset figure shows the standard curve. FIG. 5C is an image of an SDS-PAGE gel showing the molecular weight of a CH2 domain molecule (at concentrations of 1-10 μg or 2-5 μg per lane), a single chain variable fragment (scFv), an antibody fragment (Fab) and an intact antibody molecule (IgG).

Figure 6A:
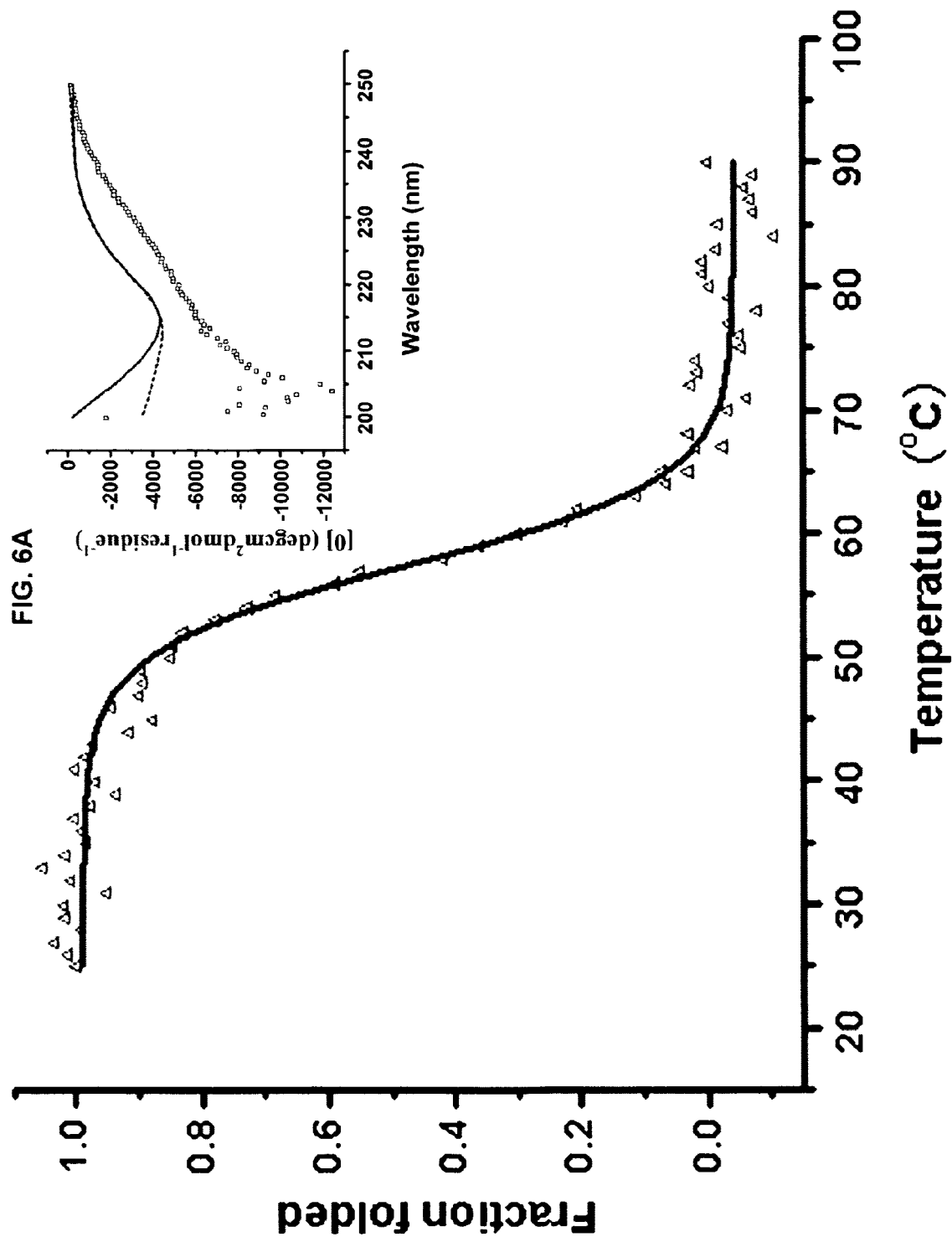
Figure 6B:
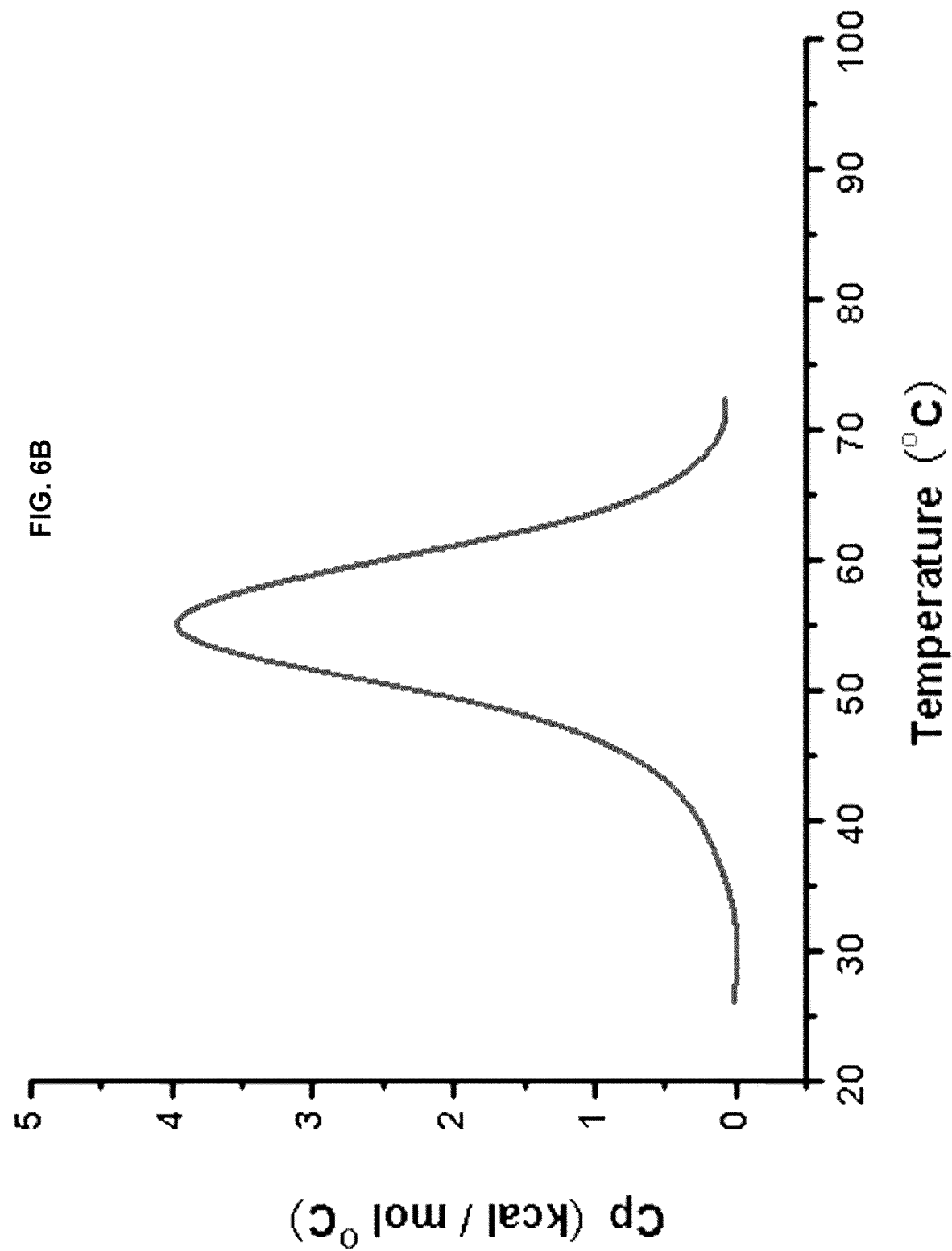

FIGS. 6A-6B are graphs showing stability of human CH2 measured by circular dichroism (CD) and differential scanning calorimetry (DSC). (A) Folding curves at 25° C. (–), unfolding at 90° C. (☐☐☐) and refolding ( - - - ) at 25° C. measured by CD. The fraction folded of the protein (ff) was calculated as ff=([θ]−[θ$_M$])/([θ$_T$]−[θ$_M$]). [θ$_T$] and [θ$_M$] where the mean residue ellipticities at 216 of folded state at 25° C. and unfolded state of 90° C. Exact $T_m$ value (54.1±1.2° C.) from CD was determined from the first derivative [d(Fraction folded)/dT] against temperature (T). (B) Thermo-induced unfolding curve from DSC. $T_m$=55.4° C., which is similar to that from CD.

Figure 7:
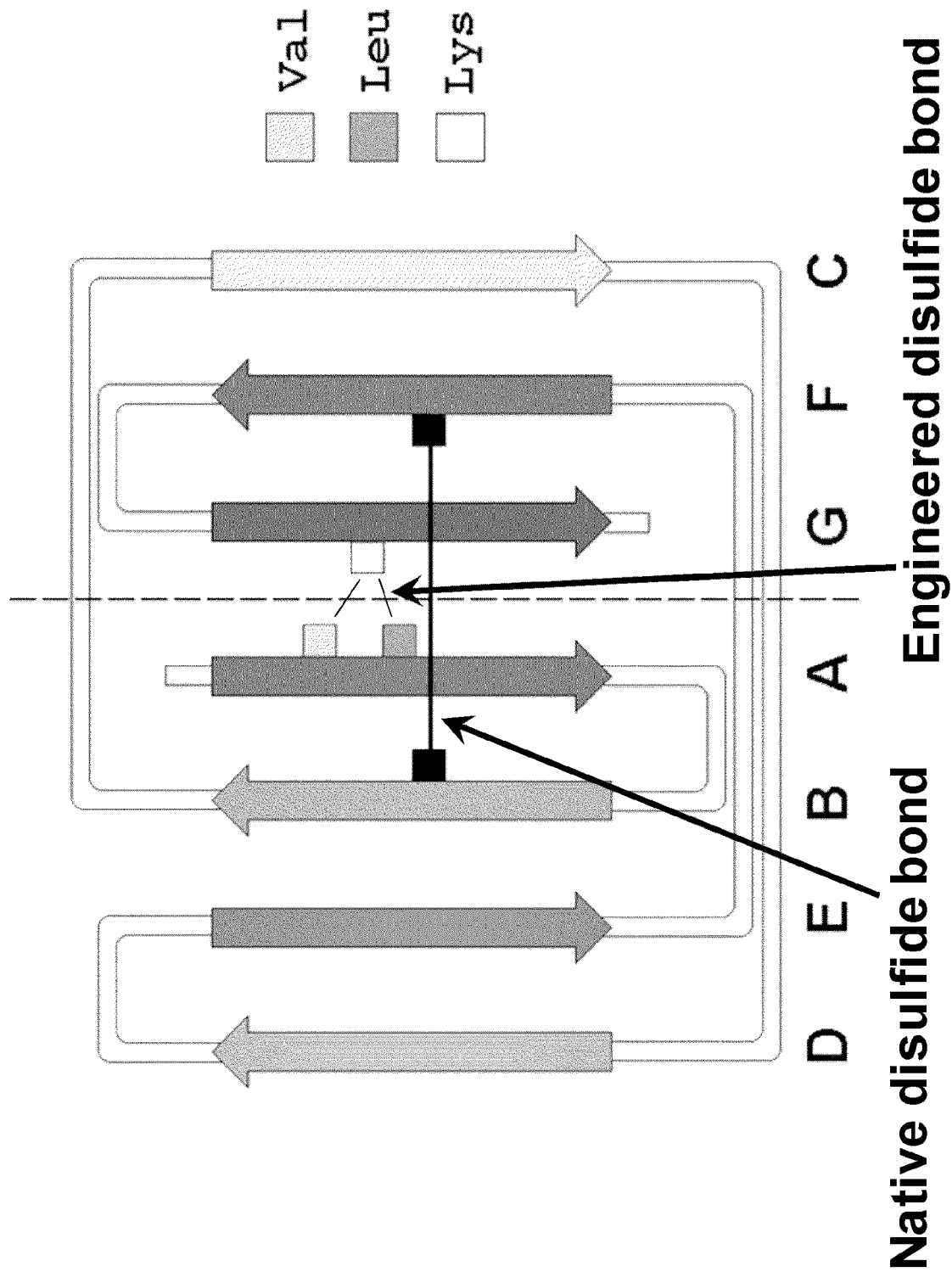

FIG. 7 is a schematic drawing showing design of m01 and m02 based on the CH2 structure. The distance between two $C^α$s in two native Cys is 6.53 Å. These two Cys residues formed a native disulfide bond (indicated by black arrow). Engineered disulfide bond were introduced between V10 and K104 (m01) or L12 and K104 (m02) replaced by cysteines.

Figure 8:
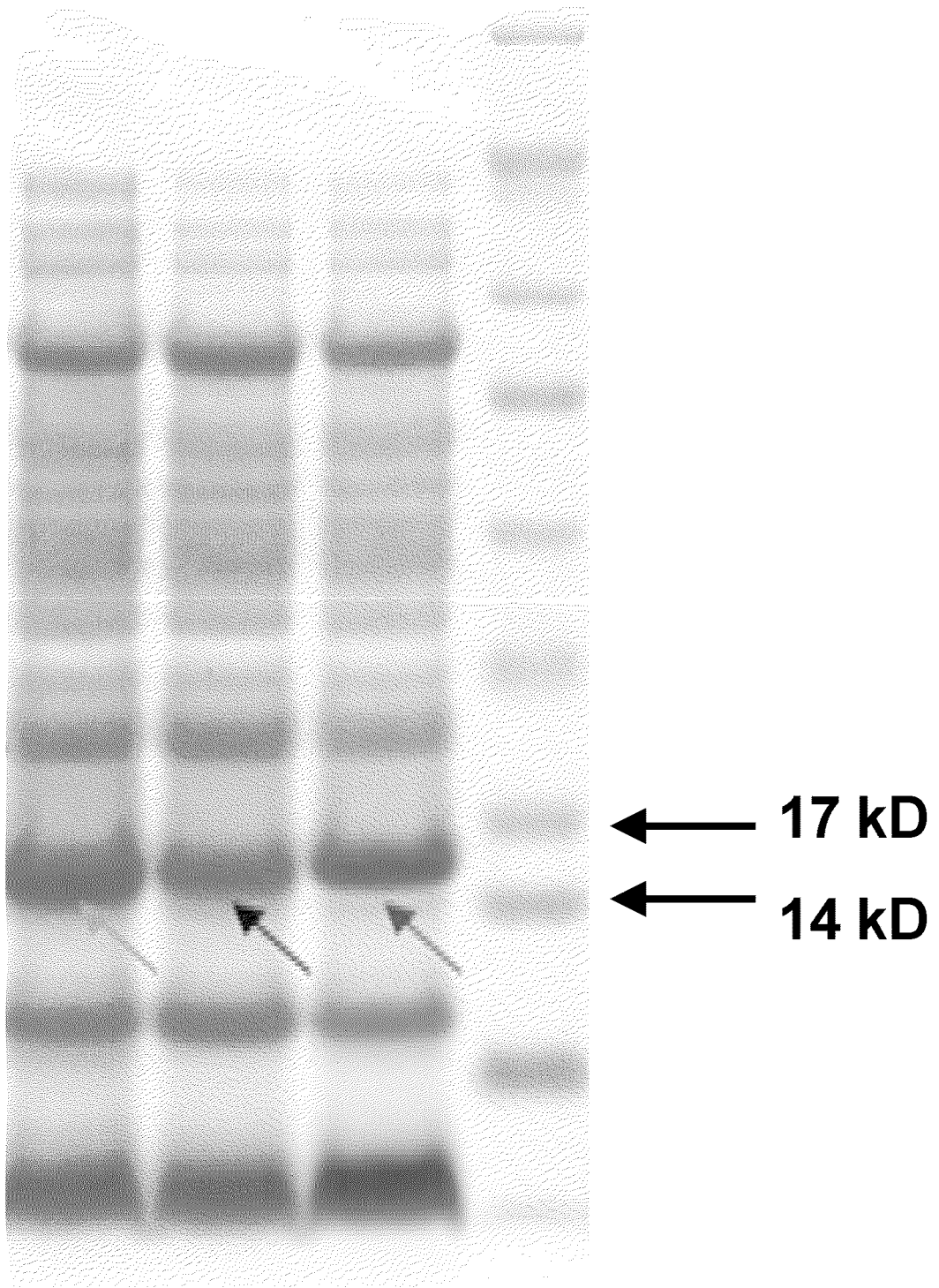

FIG. 8 is an image of an SDS-PAGE gel showing high level of expression of m01 and m02. Soluble expression of m01 and m02 was compared with that of CH2. Expression is indicated by the arrows.

FIGS. 9A-9E are graphs showing increased stability of two mutants measured by CD (A-C), DSC (D) and spectrofluorimetry (E). Folding curves at 25° C. (–), unfolding at 90° C. (☐☐☐) and refolding ( - - - ) at 25° C. of m01 (A) and m02 (B) are shown. (C) The fraction folded of m01 and m02 was calculated by the same method as for CH2. $T_m$ of m01=77.4±1.7° C., $T_m$ of m02=68.6±0.6° C. (D) Thermo-induced unfolding curves of m01 and m02 were also recorded by DSC. $T_m$ of m01 and $T_m$ of m02 increased about 20° C. and 10° C., respectively, compared to CH2. (E) Comparison of urea-induced unfolding among CH2, m01 and m02 by spectrofluorimetry. The midpoints of unfolding of CH2, m01 and m02 are 4.2, 6.8 and 5.8 M, respectively.

Figure 10A:
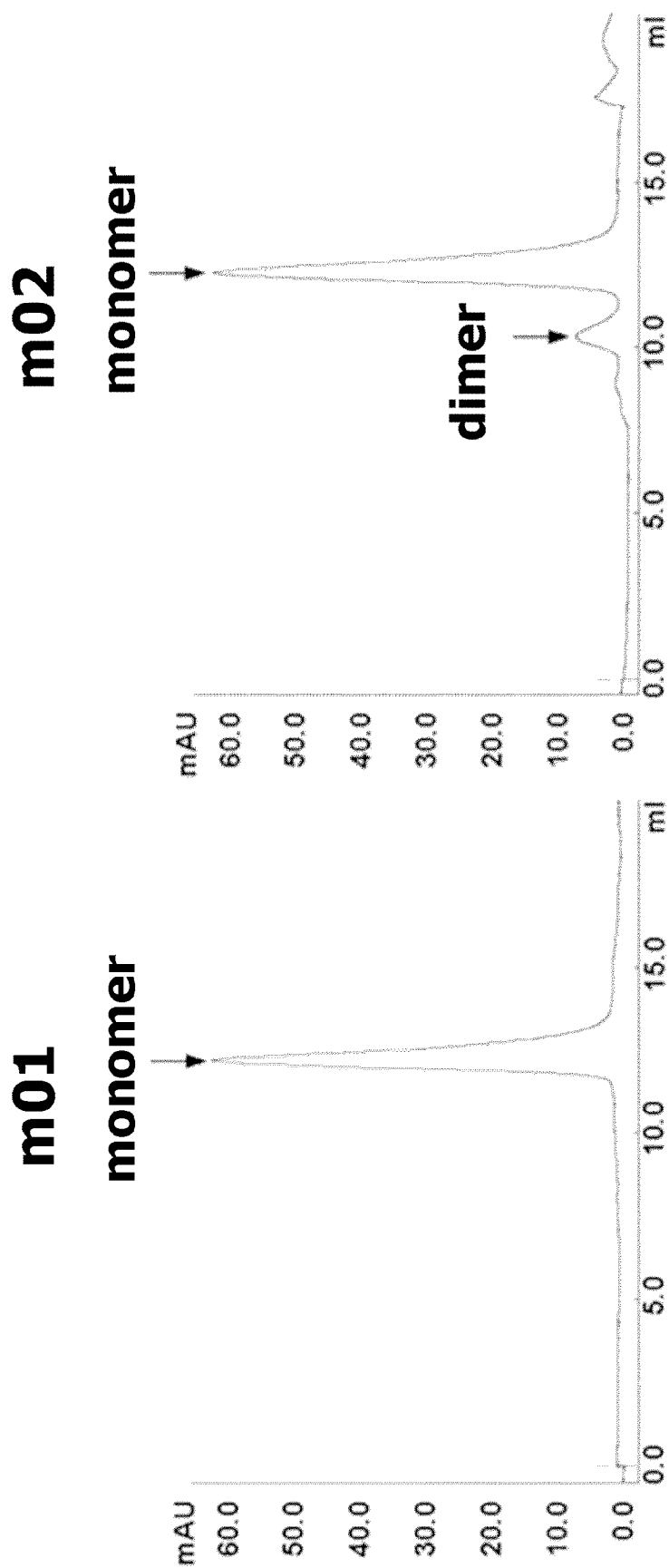
Figure 10B:
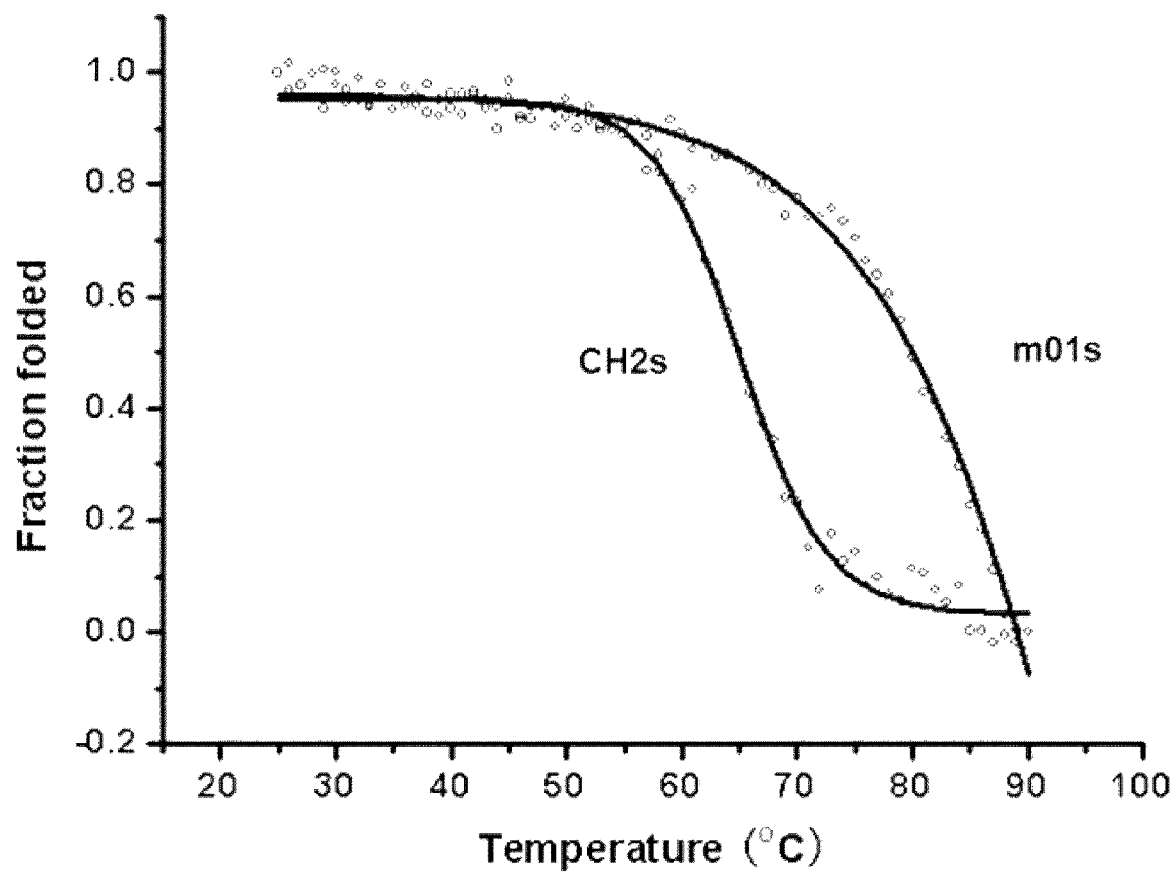

FIG. 10A shows size exclusion chromatography of m01 and m02. As CH2, m01 formed only monomer, while m02 primarily formed monomer and to a lesser degree formed dimer. FIG. 10B is a graph showing high stability of N-terminally truncated CH2 (CH2s) and truncated m01 (m01s). The first seven N-terminal residues were deleted (residues 1-7 of SEQ ID NO: 5). The 50% unfolding temperatures ($T_m$s) measured by CD (62° C. and 79° C., respectively) were significantly higher (8° C. and 5° C., respectively) than those of the corresponding CH2 and m01 (54° C. and 74° C., respectively).

Figure 11:
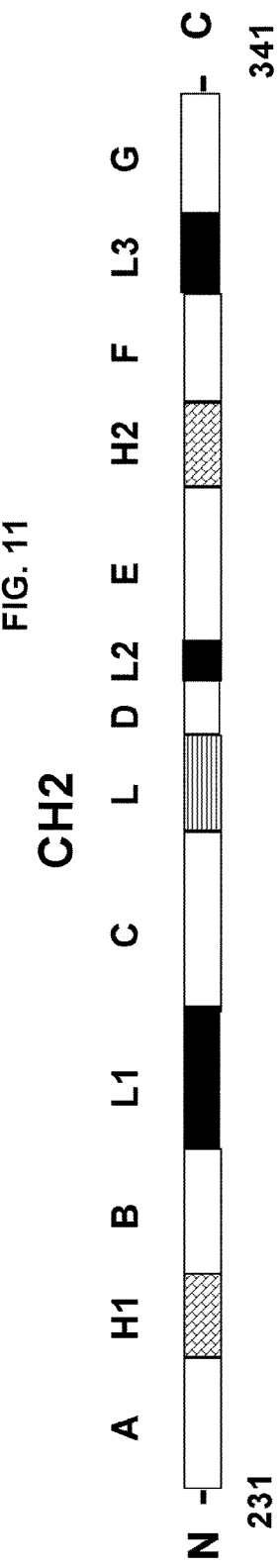

FIG. 11 is a schematic showing the design of the CH2 library. Shown is a schematic representation of the CH2 fragment, with filled rectangles representing the loops (L1-L3). Shaded rectangles represent the Loop (L) and Helixes (H1, H2) facing the opposite direction from loops 1 to 3. Empty rectangles labeled with letters A-G represent the seven β-strands forming the β sandwich structure. Numbers 231 and 341 represent the starting and ending residues of the CH2 fragment in the context of the IgG1. Sequences of CH2 loop 1 (SEQ ID NO: 93) and loop 3 (SEQ ID NO: 95) are shown below and underlined. The mutations introduced are shown in brackets (SEQ ID NOs: 94 and 96).

Figure 12A:
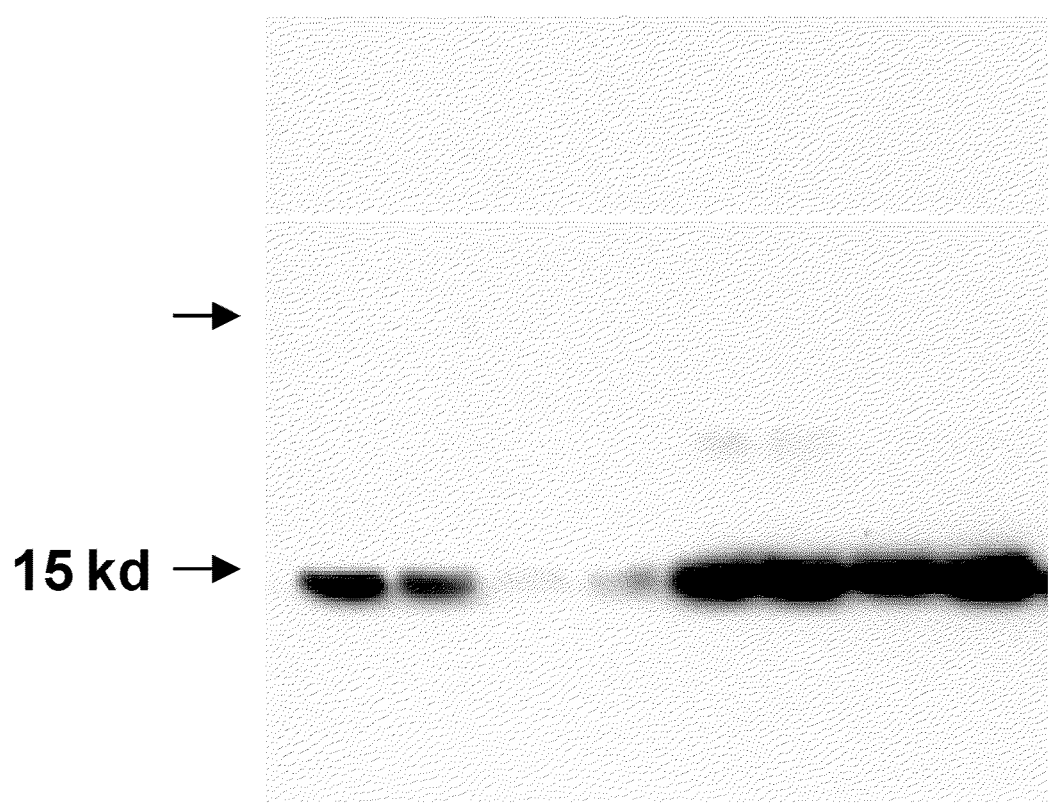
Figure 12B:
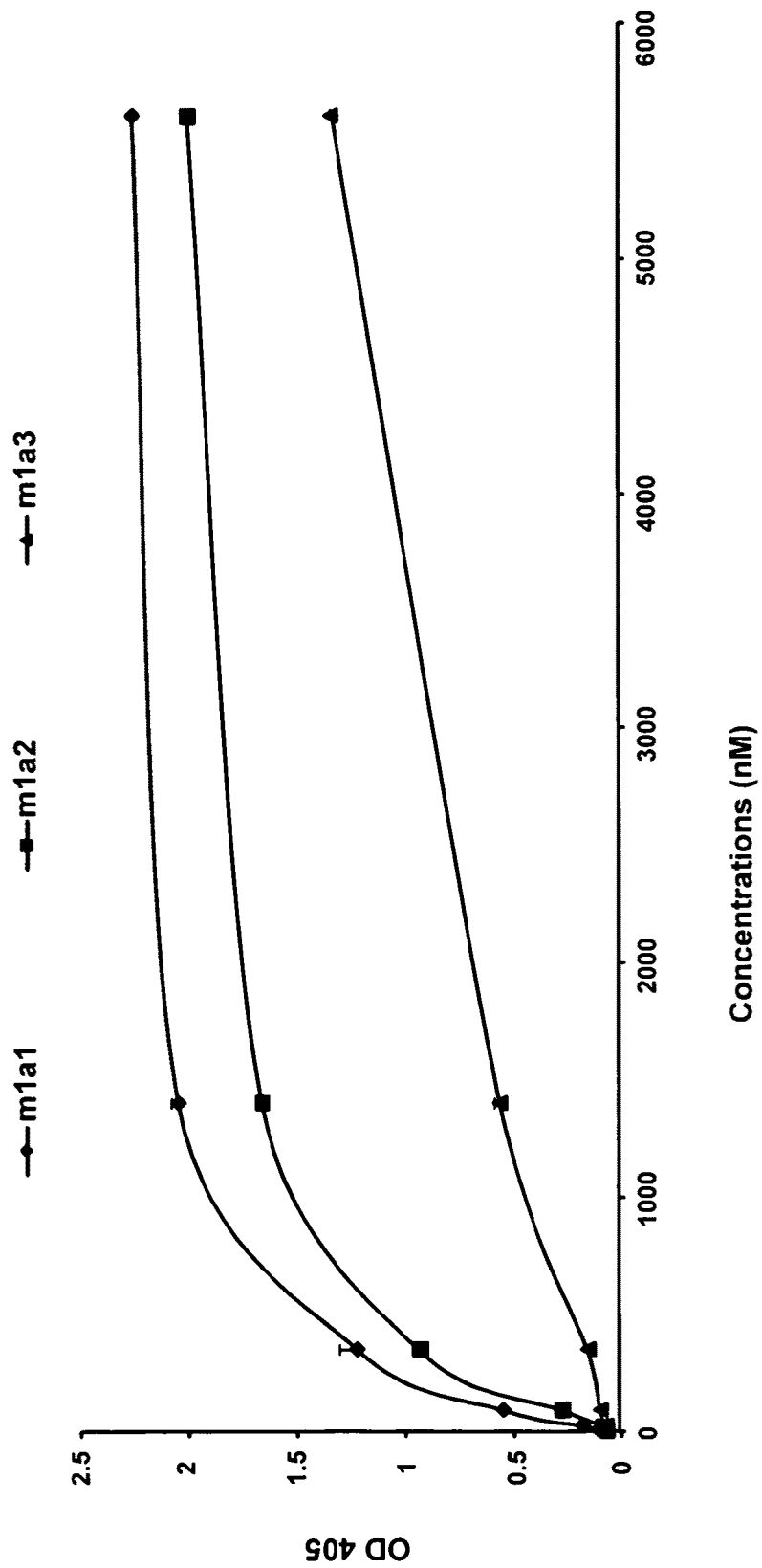

FIGS. 12A-12B show characterization of the CH2 binders. (A) The four Bal gp120-CD4 specific CH2 clones were expressed and purified as described in the Examples below. The purified product was analyzed by western blot. Samples 1-4 represent clones m1a1 to m1a3' from the soluble fraction and 5-8 renatured from the inclusion body. (B) ELISA analysis of binding of the CH2 clones to Bal gp120-CD4.

Figure 13A:
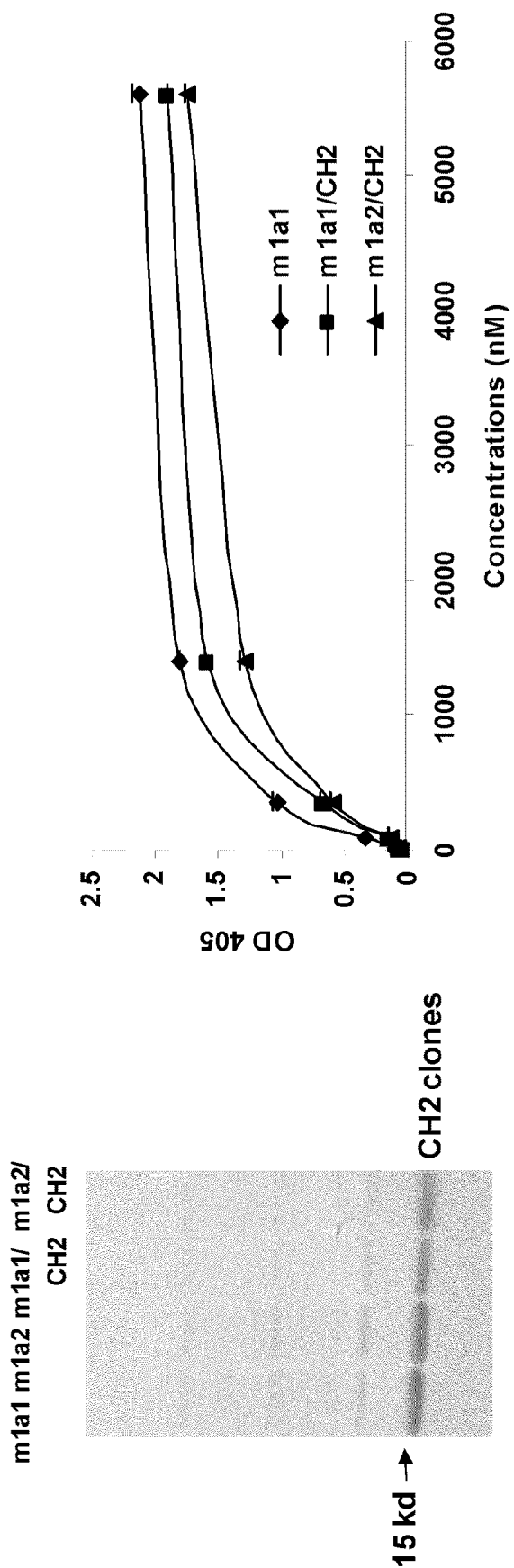

FIGS. 13A-13B are graphs and images of electrophoretic gels showing determinants of CH2 specific binding. (A) Loop 1 determines the binding ability. Two of the dominant clones m1a1 and m1a2, as well as the two hybrids containing loop 1 sequences from m1a1 and m1a3 but original CH2 loop 3 sequence were expressed and purified from the inclusion body and refolded (left panel). These proteins were then used in the ELISA analysis (right panel). (B) CH2 provided critical structural support for loop 1. The dominant clone m1a1 and its mutant carrying an additional disulfide bond were expressed, purified and refolded (left panel). They were then used in the ELSIA assay (right panel).

Figure 14:
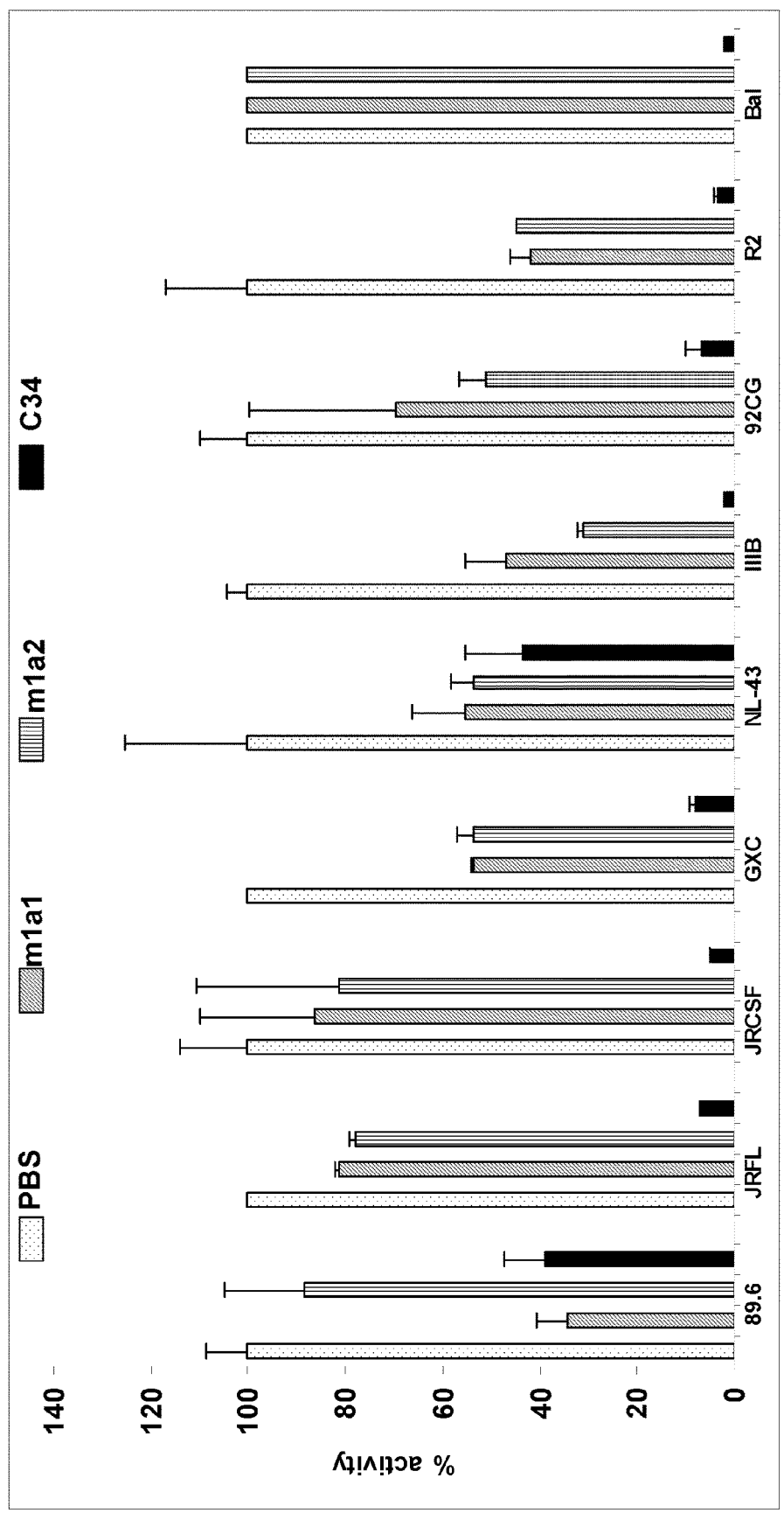
Figure 16B:
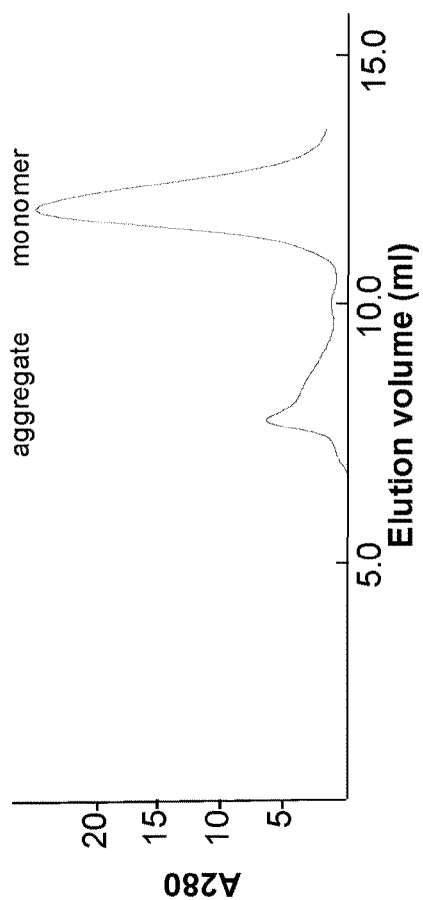
Figure 16A:
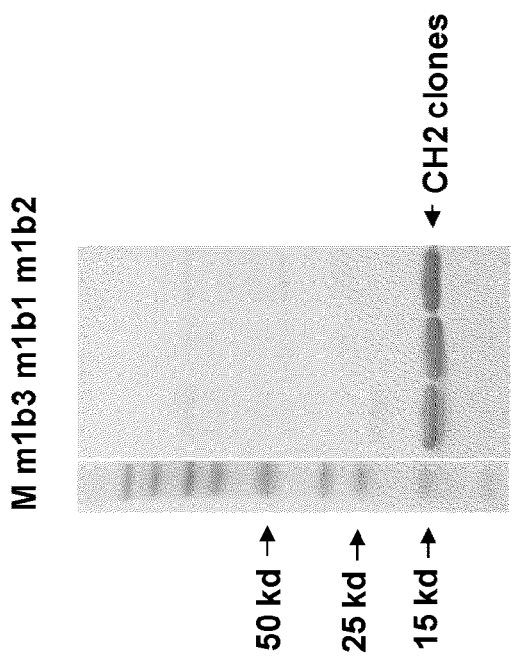
Figures 16C, 16D:
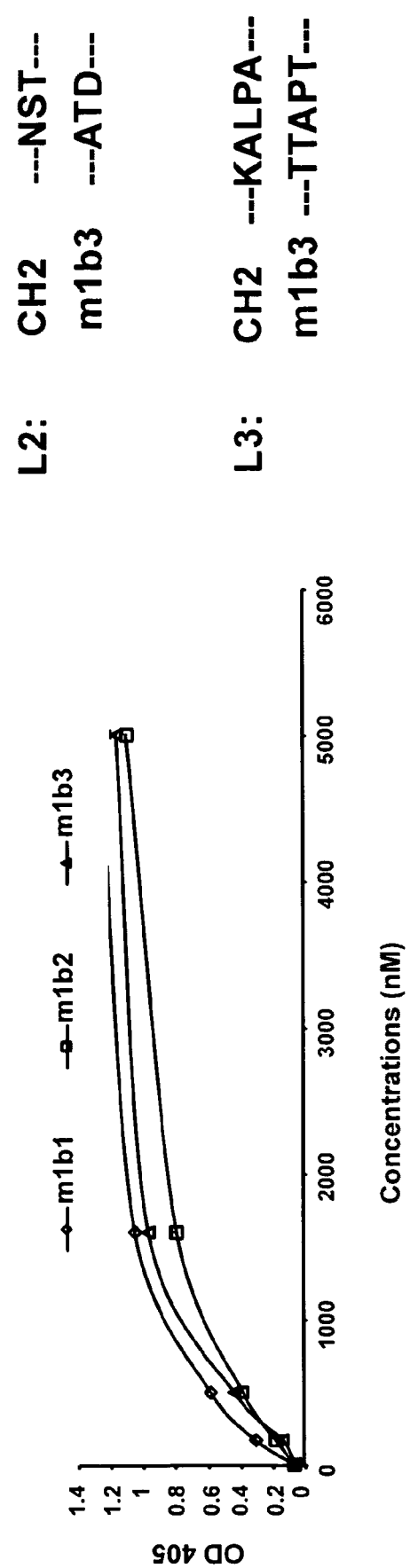

FIG. 14 is a graph showing broad neutralization of HIV Env pseudo-typed virus infection by CH2 binders. The two CH2 clones m1a1 and m1a2, at a fixed concentration of 100 μg/ml, were used to test their neutralizing ability against a panel of nine HIV pseudoviruses. C34 peptide at a concentration of 4 or 6 μg/ml was used as the positive control.

FIG. 15 shows the design of the second CH2 library based on m1a1. Loop 2 (SEQ ID NO: 97) and Loop 3 (SEQ ID NO: 99) sequences (underlined) from the CH2 clone m1a1 were replaced by those shown in parentheses (SEQ ID NOs: 98 and 100).

FIGS. 16A-16D show characterization of CH2 clones selected from the second CH2 library. (A) Expression and purification of CH2 clones selected from the second library. (B) Gel filtration analysis of m1b3. (C) ELSIA analysis of the CH2 clones. (D) The loop 2 and loop 3 sequences of the clone m1b3, which had predominantly monomeric form, in comparison to the original CH2 sequences (SEQ ID NOS: 97-100).

Figure 17:
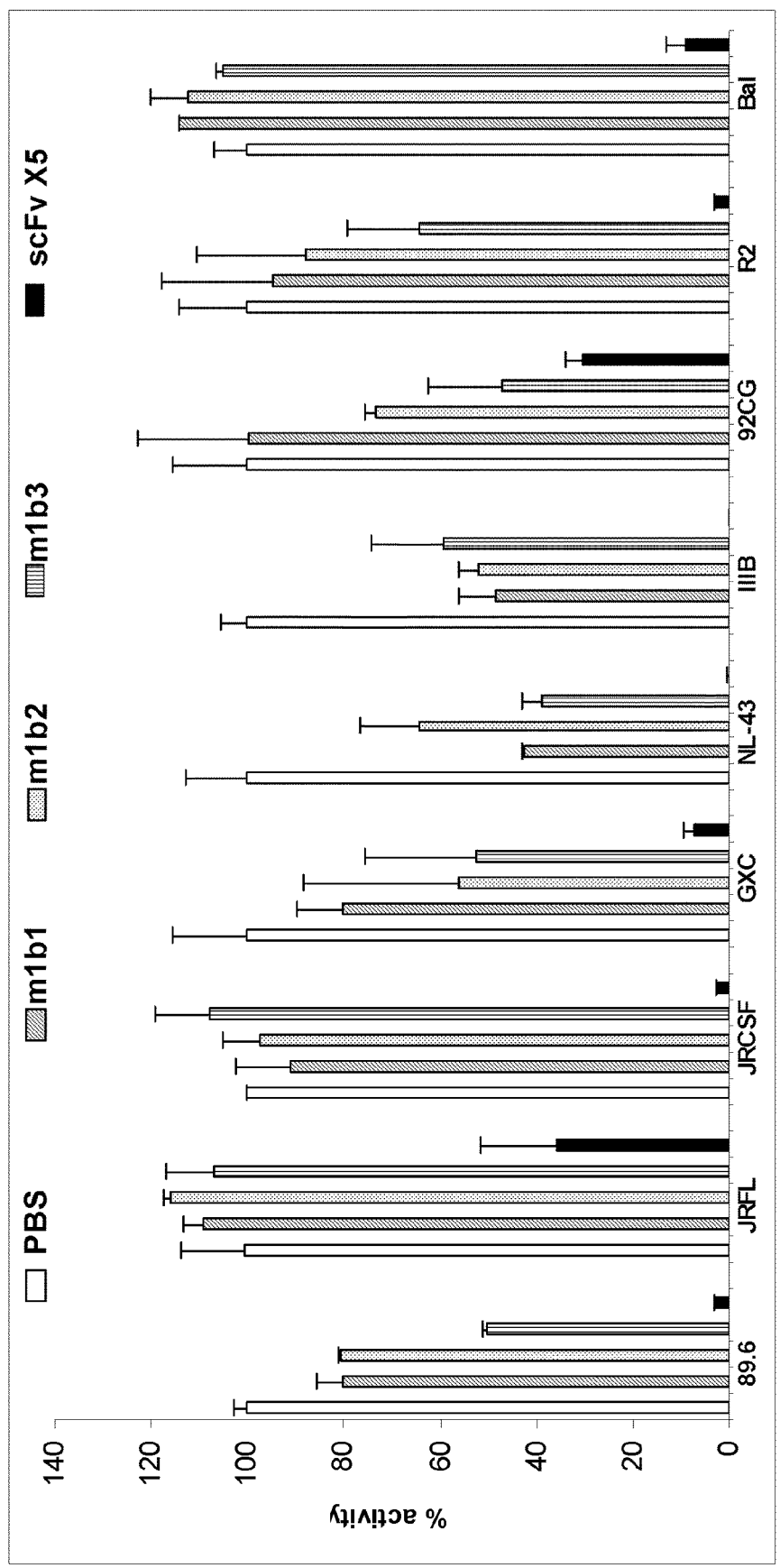

FIG. 17 is a graph showing pseudovirus neutralization by clones from the second CH2 library. Three clones isolated from the second library were analyzed for their neutralizing ability against the same panel of HIV pseudoviruses at a concentration of 100 μg/ml. ScFv X5 purified in parallel was used as a control at a concentration of 20 μg/ml.

Figure 18:
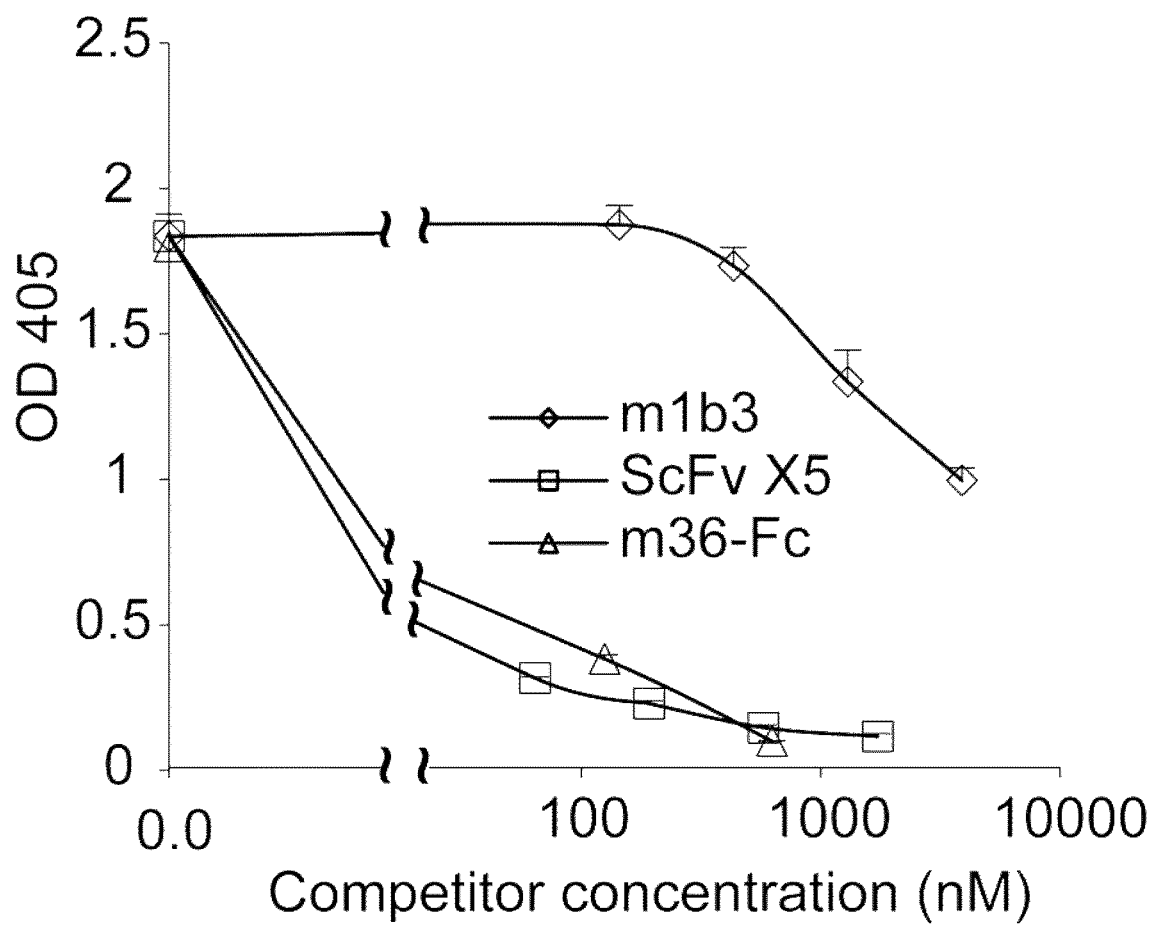

FIG. 18 is a graph showing CH2 binder recognized a conserved epitope. The predominantly monomeric CH2 clone m1b3 was biotin labeled and used in a competition ELISA assay. ELISA antigen Bal gp120-CD4 was coated at the bottom of the ELISA plate. Fixed amount of biotinylated m1b3 at 1.7 μM was mixed with indicated amount of unlabeled m1b3, scFv X5 or m36-Fc and added to each well. The bound m1b3 was detected with streptavidin-HRP.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 11, 2013, 45.1 KB, which is incorporated by reference herein. In the accompanying sequence listing:

SEQ ID NO: 1 is the amino acid sequence of a human $V_H$ domain.

SEQ ID NOs: 2-4 are the amino acid sequences of the $V_H$ domains of three human antibodies.

SEQ ID NO: 5 is the amino acid sequence of the human γ1 CH2 domain

SEQ ID NOs: 6-10 are nucleotide sequences of PCR primers for generation of a library of mutant CH2 domains.

SEQ ID NOs: 11-30 are the amino acid sequences of fragments of mutant CH2 domains with randomized Loop 1.

SEQ ID NOs: 31-50 are the amino acid sequences of fragments of mutant CH2 domains with randomized Loop 3.

SEQ ID NOs: 51-68 are nucleotide sequences of PCR primers for engraftment of CDR3s from human antibodies into the CH2 scaffold.

SEQ ID NOs: 69-87 are amino acid sequences of fragments of engineered CH2 domains with grafted H3s.

SEQ ID NOs: 88 and 89 are amino acid sequences of fragments of the CH2 domain mutant m01.

SEQ ID NOs: 90 and 91 are amino acid sequences of fragments of the CH2 domain mutant m02.

SEQ ID NO: 92 is the amino acid sequence of murine CH2.

SEQ ID NO: 93 is the amino acid sequence of CH2 loop 1.

SEQ ID NO: 94 is the consensus amino acid sequence of mutant CH2 loop 1.

SEQ ID NO: 95 is the amino acid sequence of CH2 loop 3.

SEQ ID NO: 96 is the consensus amino acid sequence of mutant CH2 loop 3.

SEQ ID NO: 97 is the amino acid sequence of CH2 loop 2 from clone m1a1.

SEQ ID NO: 98 is the consensus amino acid sequence of mutant CH2 loop 2 derived from clone m1a1.

SEQ ID NO: 99 is the amino acid sequence of CH2 loop 3 from clone m1a1.

SEQ ID NO: 100 is the consensus amino acid sequence of mutant CH2 loop 3 derived from clone m1a1.

SEQ ID NOs: 101-105 are the nucleotide sequences of PCR primers for amplification of the first CH2 library.

SEQ ID NO: 106 is the amino acid sequence of an m1a1 synthetic peptide.

SEQ ID NO: 107 is the amino acid sequence of m1a1 loop 1.

SEQ ID NO: 108 is the amino acid sequence of m1a2 loop 1.

SEQ ID NO: 109 is the amino acid sequence of m1a3 and m1a3' loop 1.

SEQ ID NO: 110 is the amino acid sequence of m1a1 loop 3.

SEQ ID NO: 111 is the amino acid sequence of m1a2 loop 3.

SEQ ID NO: 112 is the amino acid sequence of m1a3 loop 3.

SEQ ID NO: 113 is the amino acid sequence of m1a3' loop 3.

DETAILED DESCRIPTION

I. Abbreviations

ADCC: Antibody-dependent cell-mediated cytotoxicity
CDC: Complement-dependent cytotoxicity
CDR: Complementarity determining region
DNA: Deoxyribonucleic acid
ELISA: Enzyme-linked immunosorbent assay
HIV: Human immunodeficiency virus
Ig: Immunoglobulin
NK: Natural killer
RNA: Ribonucleic acid
SDR: Specificity determining residue II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Administration: The introduction of a composition into a subject by a chosen route. For example, if the chosen route is intravenous, the composition is administered by introducing the composition into a vein of the subject.

Animal: Living multi-cellular vertebrate organisms, a category that includes, for example, mammals and birds. The term mammal includes both human and non-human mammals. Similarly, the term "subject" includes both human and veterinary subjects.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains. Each light chain contains a single constant domain (CL), while each heavy chain contains three constant domains, CH1, CH2 and CH3 (or four constant domains for IgE and IgM). See FIG. 1A for a schematic drawing of a conventional immunoglobulin molecule.

As used herein, the term "antibodies" includes intact immunoglobulins as well as a number of well-characterized fragments having a molecular weight of about 25 to 100 kD. For instance, Fabs, Fvs, and single-chain Fvs (scFvs) that bind to target protein (or an epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2)

Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) scFv, single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, (*Using Antibodies: A Laboratory Manual*, CSHL, New York, 1999).

Antibodies can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described, for example, by Harlow and Lane (*Using Antibodies: A Laboratory Manual*, CSHL, New York, 1999).

A "humanized" immunoglobulin, such as a humanized antibody, is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. A "humanized antibody" is an antibody, such as a humanized monoclonal antibody, comprising a humanized light chain and a humanized heavy chain immunoglobulin. A humanized antibody binds to the same or similar antigen as the donor antibody that provides the CDRs. The acceptor framework of a humanized immunoglobulin may have a limited number of substitutions by amino acids taken from the donor framework. Humanized molecules can have additional conservative amino acid substitutions which have substantially no effect on antigen binding or other immunoglobulin functions. These molecules can be constructed by means of genetic engineering (for example, see U.S. Pat. No. 5,585,089).

Antigen: A compound, composition, or substance that can stimulate the production of antibodies or a T-cell response in an animal, including compositions that are injected or absorbed into an animal. An antigen reacts with the products of specific humoral or cellular immunity.

Autoimmune disease: A disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the microorganisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

Binding affinity: The strength of binding between a binding site and a ligand (for example, between an antibody, CH2 domain or CH3 domain and an antigen or epitope). The affinity of a binding site X for a ligand Y is represented by the dissociation constant ($K_d$), which is the concentration of Y that is required to occupy half of the binding sites of X present in a solution. A lower ($K_d$) indicates a stronger or higher-affinity interaction between X and Y and a lower concentration of ligand is needed to occupy the sites. In general, binding affinity can be affected by the alteration, modification and/or substitution of one or more amino acids in the epitope recognized by the paratope (portion of the molecule that recognizes the epitope). Binding affinity can be the affinity of antibody binding an antigen.

In one example, binding affinity is measured by end-point titration in an Ag-ELISA assay. Binding affinity is substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

CH2 or CH3 domain molecule: A polypeptide (or nucleic acid encoding a polypeptide) derived from an immunoglobulin CH2 or CH3 domain. The immunoglobulin can be IgG, IgA, IgD, IgE or IgM. In one embodiment described herein, the CH2 or CH3 domain molecule comprises at least one CDR, or functional fragment thereof. The CH2 or CH3 domain molecule can further comprise additional amino acid sequence, such as a complete hypervariable loop. In another embodiment, the CH2 or CH3 domain molecules have at least a portion of one or more loop regions replaced with a CDR, or functional fragment thereof. In some embodiments described herein, the CH2 or CH3 domains comprise one or more mutations in a loop region of the molecule. A "loop region" of a CH2 or CH3 domain refers to the portion of the protein located between regions of O-sheet (for example, each CH2 domain comprises seven β-sheets, A to G, oriented from the N- to C-terminus). As shown in FIGS. 3A-3C, a CH2 domain comprises six loop regions: Loop 1, Loop 2, Loop 3, Loop A-B, Loop C-D and Loop E-F. Loops A-B, C-D and E-F are located between β-sheets A and B, C and D, and E and F, respectively. Loops 1, 2 and 3 are located between β-sheets B and C, D and E, and F and G, respectively. See Table 1 for the amino acid ranges of the loops in a CH2 domain. The CH2 and CH3 domain molecules disclosed herein can also comprise an N-terminal deletion, such as a deletion of about 1 to about 7 amino acids. In particular examples, the N-terminal deletion is 1, 2, 3, 4, 5, 6 or 7 amino acids in length. The CH2 and CH3 domain molecules disclosed herein can also comprise a C-terminal deletion, such as a deletion of about 1 to about 4 amino acids. In particular examples, the C-terminal deletion is 1, 2, 3 or 4 amino acids in length.

CH2 and CH3 domain molecules are small in size, usually less than 15 kD. The CH2 and CH3 domain molecules can vary in size depending on the length of CDR/hypervariable amino acid sequence inserted in the loops regions, how many CDRs are inserted and whether another molecule (such as an effector molecule or label) is conjugated to the CH2 or CH3 domain. In some embodiments, the CH2 or CH3 domain molecules do not comprise additional constant domains (i.e.

CH1 or another CH2 or CH3 domain) or variable domains. In one embodiment, the CH2 domain is from IgG, IgA or IgD. In another embodiment, the constant domain is a CH3 domain from IgE or IgM, which is homologous to the CH2 domains of IgG, IgA or IgD.

The CH2 and CH3 domain molecules provided herein can be glycosylated or unglycosylated. For example, a recombinant CH2 or CH3 domain can be expressed in an appropriate mammalian cell to allow glycosylation of the molecule.

Complementarity determining region (CDR): A short amino acid sequence found in the variable domains of antigen receptor (such as immunoglobulin and T cell receptor) proteins that provides the receptor with contact sites for antigen and its specificity for a particular antigen. Each polypeptide chain of an antigen receptor contains three CDRs (CDR1, CDR2 and CDR3). Antigen receptors are typically composed of two polypeptide chains (a heavy chain and a light chain), therefore there are six CDRs for each antigen receptor that can come into contact with the antigen. Since most sequence variation associated with antigen receptors are found in the CDRs, these regions are sometimes referred to as hypervariable domains.

CDRs are found within loop regions of an antigen receptor (usually between regions of β-sheet structure; see FIGS. 3A-3C). These loop regions are typically referred to as hypervariable loops. Each antigen receptor comprises six hypervariable loops: H1, H2, H3, L1, L2 and L3. For example, the H1 loop comprises CDR1 of the heavy chain and the L3 loop comprises CDR3 of the light chain. The CH2 and CH3 domain molecules described herein comprise engrafted amino acids from a variable domain of an antibody. The engrafted amino acids comprise at least a portion of a CDR. The engrafted amino acids can also include additional amino acid sequence, such as a complete hypervariable loop. As used herein, a "functional fragment" of a CDR is at least a portion of a CDR that retains the capacity to bind a specific antigen.

A numbering convention for the location of CDRs is described by Kabat et al., (1991) *Sequences of Proteins of Immunological Interest*, 5$^{th}$ Edition, U.S. Department of Health and Human Services, Public Health Service, National Institutes of Health, Bethesda, Md. (NIH Publication No. 91-3242).

Contacting: Placement in direct physical association, which includes both in solid and in liquid form.

Degenerate variant: As used herein, a "degenerate variant" of a CH2 or CH3 domain molecule is a polynucleotide encoding a CH2 or CH3 domain molecule that includes a sequence that is degenerate as a result of the genetic code. There are 20 natural amino acids, most of which are specified by more than one codon. Therefore, all degenerate nucleotide sequences are included as long as the amino acid sequence of the CH2 or CH3 domain molecule encoded by the nucleotide sequence is unchanged.

Domain: A protein structure which retains its tertiary structure independently of the remainder of the protein. In some cases, domains have discrete functional properties and can be added, removed or transferred to another protein without a loss of function.

Effector molecule: A molecule, or the portion of a chimeric molecule, that is intended to have a desired effect on a cell to which the molecule or chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as a CH2 or CH3 domain molecule, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341-365, 1985. Diagnostic agents or moieties include radioisotopes and other detectable labels. Detectable labels useful for such purposes are also well known in the art, and include radioactive isotopes such as $^{32}$P, $^{125}$I, and $^{131}$I, fluorophores, chemiluminescent agents, and enzymes.

Epitope: An antigenic determinant These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Expression: The translation of a nucleic acid into a protein. Proteins may be expressed and remain intracellular, become a component of the cell surface membrane, or be secreted into the extracellular matrix or medium Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Framework region: Amino acid sequences interposed between CDRs (or hypervariable regions). Framework regions include variable light and variable heavy framework regions. Each variable domain comprises four framework regions, often referred to as FR1, FR2, FR3 and FR4. The framework regions serve to hold the CDRs in an appropriate orientation for antigen binding. Framework regions typically form β-sheet structures.

Fungal-associated antigen (FAAs): A fungal antigen which can stimulate fungal-specific T-cell-defined immune responses. Exemplary FAAs include, but are not limited to, an antigen from *Candida albicans, Cryptococcus* (such as d25, or the MP98 or MP88 mannoprotein from *C. neoformans*, or an immunological fragment thereof), *Blastomyces* (such as *B. dermatitidis*, for example WI-1 or an immunological fragment thereof), and *Histoplasma* (such as *H. capsulatum*).

Heterologous: A heterologous polypeptide or polynucleotide refers to a polypeptide or polynucleotide derived from a different source or species.

Hypervariable region: Regions of particularly high sequence variability within an antibody variable domain. The hypervariable regions form loop structures between the β-sheets of the framework regions. Thus, hypervariable regions are also referred to as "hypervariable loops." Each variable domain comprises three hypervariable regions, often referred to as H1, H2 and H3 in the heavy chain, and L1, L2 and L3 in the light chain. The loop structures of the hypervariable loops are depicted in FIGS. 3A-5C.

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunoconjugate: A covalent linkage of an effector molecule to an antibody or a CH2 or CH3 domain molecule. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as domain Ia of PE and the B chain of DT) and replacing it with a different targeting moiety, such as a CH2 or CH3 domain molecule. In one embodiment, a CH2 or CH3 domain molecule is joined to an effector molecule (EM). In another embodiment, a CH2 or CH3 domain molecule joined to an effector molecule is further joined to a lipid or other molecule to a protein or peptide to increase its half-life in the body. The linkage can be either by chemical or recombinant means. "Chemical means" refers to a reaction between the CH2 or CH3 domain molecule and the effector molecule such that there is a covalent bond formed between the two molecules to form one molecule. A peptide linker (short peptide sequence) can optionally be included between the CH2 or CH3 domain molecule and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand, antibody or CH2 or CH3 domain molecule, conjugated (coupled) to an effector molecule.

The terms "conjugating," "joining," "bonding" or "linking" refer to making two polypeptides into one contiguous polypeptide molecule, or to covalently attaching a radionucleotide or other molecule to a polypeptide, such as a CH2 or CH3 domain molecule. In the specific context, the terms include reference to joining a ligand, such as an antibody moiety, to an effector molecule ("EM").

Immunogen: A compound, composition, or substance which is capable, under appropriate conditions, of stimulating an immune response, such as the production of antibodies or a T-cell response in an animal, including compositions that are injected or absorbed into an animal.

Isolated: An "isolated" biological component (such as a nucleic acid molecule or protein) has been substantially separated or purified away from other biological components from which the component naturally occurs (for example, other biological components of a cell), such as other chromosomal and extra-chromosomal DNA and RNA and proteins, including other antibodies. Nucleic acids and proteins that have been "isolated" include nucleic acids and proteins purified by standard purification methods. An "isolated antibody" is an antibody that has been substantially separated or purified away from other proteins or biological components such that its antigen specificity is maintained. The term also embraces nucleic acids and proteins (including CH2 and CH3 domain molecules) prepared by recombinant expression in a host cell, as well as chemically synthesized nucleic acids or proteins, or fragments thereof.

Label: A detectable compound or composition that is conjugated directly or indirectly to another molecule, such as an antibody or CH2 or CH3 domain molecule, to facilitate detection of that molecule. Specific, non-limiting examples of labels include fluorescent tags, enzymatic linkages, and radioactive isotopes.

Ligand contact residue or Specificity Determining Residue (SDR): A residue within a CDR that is involved in contact with a ligand or antigen. A ligand contact residue is also known as a specificity determining residue (SDR). A non-ligand contact residue is a residue in a CDR that does not contact a ligand. A non-ligand contact residue can also be a framework residue.

Nanoantibody (nAb): A CH2 or CH3 domain molecule engineered such that the molecule specifically binds antigen. The CH2 and CH3 domain molecules engineered to bind antigen are the smallest known antigen-specific binding antibody domain-based molecules.

Neoplasia and Tumor: The product of neoplasia is a neoplasm (a tumor), which is an abnormal growth of tissue that results from excessive cell division. Neoplasias are also referred to as "cancer." A tumor that does not metastasize is referred to as "benign." A tumor that invades the surrounding tissue and/or can metastasize is referred to as "malignant."

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2'-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pathogen: A biological agent that causes disease or illness to its host. Pathogens include, for example, bacteria, viruses, fungi, protozoa and parasites. Pathogens are also referred to as infectious agents.

Examples of pathogenic viruses include those in the following virus families: *Retroviridae* (for example, human immunodeficiency virus (HIV); human T-cell leukemia viruses (HTLV); *Picornaviridae* (for example, polio virus, hepatitis A virus; hepatitis C virus; enteroviruses, human coxsackie viruses, rhinoviruses, echoviruses; foot-and-mouth disease virus); *Calciviridae* (such as strains that cause gastroenteritis); *Togaviridae* (for example, equine encephalitis viruses, rubella viruses); *Flaviridae* (for example, dengue viruses; yellow fever viruses; West Nile virus; St. Louis encephalitis virus; Japanese encephalitis virus; and other encephalitis viruses); *Coronaviridae* (for example, coronaviruses; severe acute respiratory syndrome (SARS) virus; *Rhabdoviridae* (for example, vesicular stomatitis viruses, rabies viruses); *Filoviridae* (for example, Ebola viruses); *Paramyxoviridae* (for example, parainfluenza viruses, mumps virus, measles virus, respiratory syncytial virus (RSV)); *Orthomyxoviridae* (for example, influenza viruses); *Bunyaviridae* (for example, Hantaan viruses; Sin Nombre virus, Rift Valley fever virus; bunya viruses, phleboviruses and Nairo viruses); *Arena viridae* (hemorrhagic fever viruses; Machupo virus; Junin virus); *Reoviridae* (e.g., reoviruses, orbivurses and rotaviruses); *Birnaviridae; Hepadnaviridae* (Hepatitis B virus); *Parvoviridae* (parvoviruses); *Papovaviridae* (papilloma viruses, polyoma viruses; BK-virus); *Adenoviridae* (most adenoviruses); *Herpesviridae* (herpes simplex virus (HSV)-1 and HSV-2; cytomegalovirus (CMV); Epstein-Barr virus (EBV); varicella zoster virus (VZV); and other herpes viruses, including HSV-6); *Poxyiridae* (variola viruses, vaccinia viruses, pox viruses); and *Iridoviridae* (such as African swine fever virus); *Filoviridae* (for example, Ebola virus; Marburg virus); *Caliciviridae* (for example, Norwalk viruses) and unclassified viruses (for example, the etiological agents of Spongiform encephalopathies, the agent of delta hepatitis (thought to be a defective satellite of hepatitis B virus); and astroviruses).

Examples of fungal pathogens include, but are not limited to: *Cryptococcus neoformans, Histoplasma capsulatum, Coccidioides immitis, Blastomyces dermatitidis, Chlamydia trachomatis, Candida albicans.*

Examples of bacterial pathogens include, but are not limited to: *Helicobacter pyloris, Borelia burgdorferi, Legionella pneumophilia, Mycobacteria sps* (such as *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli.*

Other pathogens (such as protists) include: *Plasmodium falciparum* and *Toxoplasma gondii.*

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more antibodies, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

"Conservative" amino acid substitutions are those substitutions that do not substantially affect or decrease an activity or antigenicity of a polypeptide. For example, a polypeptide can include at most about 1, at most about 2, at most about 5, at most about 10, or at most about 15 conservative substitutions and specifically bind an antibody that binds the original polypeptide. The term conservative variation also includes the use of a substituted amino acid in place of an unsubstituted parent amino acid, provided that antibodies raised antibodies raised to the substituted polypeptide also immunoreact with the unsubstituted polypeptide. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, and/or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Probes and primers: A probe comprises an isolated nucleic acid attached to a detectable label or reporter molecule. Primers are short nucleic acids, and can be DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Purified: The term purified does not require absolute purity; rather, it is intended as a relative term. Thus, for example, a purified CH2 or CH3 domain molecule is one that is isolated in whole or in part from naturally associated proteins and other contaminants in which the molecule is purified to a measurable degree relative to its naturally occurring state, for example, relative to its purity within a cell extract or biological fluid.

The term "purified" includes such desired products as analogs or mimetics or other biologically active compounds wherein additional compounds or moieties are bound to the CH2 or CH3 domain molecule in order to allow for the attachment of other compounds and/or provide for formulations useful in therapeutic treatment or diagnostic procedures.

Generally, substantially purified CH2 or CH3 domain molecules include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the CH2 or CH3 domain molecule is purified to represent greater than 90%, often greater than 95% of all macromolecular species present in a purified preparation prior to admixture with other formulation ingredients. In other cases, the purified preparation may be essentially homogeneous, wherein other macromolecular species are less than 1%.

Recombinant: A recombinant nucleic acid or polypeptide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Sample: A portion, piece, or segment that is representative of a whole. This term encompasses any material, including for instance samples obtained from a subject.

A "biological sample" is a sample obtained from a subject including, but not limited to, cells, tissues and bodily fluids. Bodily fluids include, for example, saliva, sputum, spinal fluid, urine, blood and derivatives and fractions of blood, including serum and lymphocytes (such as B cells, T cells and subfractions thereof). Tissues include those from biopsies, autopsies and pathology specimens, as well as biopsied or surgically removed tissue, including tissues that are, for example, unfixed, frozen, fixed in formalin and/or embedded in paraffin.

In particular embodiments, the biological sample is obtained from a subject, such as blood or serum. A biological sample is typically obtained from a mammal, such as a rat, mouse, cow, dog, guinea pig, rabbit, or primate. In one embodiment, the primate is macaque, chimpanzee, or a human.

Scaffold: As used herein, a CH2 or CH3 domain scaffold is a recombinant CH2 or CH3 domain that can be used as a platform to introduce mutations (such as into the loop regions; see FIG. 2 and FIGS. 3A-3C) in order to confer antigen binding to the CH2 or CH3 domain. In some embodiments, the scaffold is altered to exhibit increased stability compared with the native CH2 or CH3 domain. In particular examples, the scaffold is mutated to introduce pairs of cysteine residues to allow formation of one or more non-native disulfide bonds. In some cases, the scaffold is a CH2 or CH3 domain having an N-terminal deletion, such as a deletion of about 1 to about 7 amino acids.

Sequence identity: The similarity between nucleotide or amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, CABIOS 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990.) is available from several sources, including the National Center for Biotechnology Information (NCBI, Bethesda, Md.) and on the Internet, for use in connection with the sequence analysis programs blastp, blastn, blastx, tblastn and tblastx.

Specific binding agent: An agent that binds substantially only to a defined target. Thus an antigen specific binding agent is an agent that binds substantially to an antigenic polypeptide or antigenic fragment thereof. In one embodiment, the specific binding agent is a monoclonal or polyclonal antibody or a CH2 or CH3 domain molecule that specifically binds the antigenic polypeptide or antigenic fragment thereof.

The term "specifically binds" refers, with respect to an antigen, to the preferential association of an antibody or other ligand, in whole or part, with a cell or tissue bearing that antigen and not to cells or tissues lacking a detectable amount of that antigen. It is, of course, recognized that a certain degree of non-specific interaction may occur between a molecule and a non-target cell or tissue. Nevertheless, specific binding may be distinguished as mediated through specific recognition of the antigen. Specific binding results in a much stronger association between the antibody (or CH2 or CH3 domain molecule) and cells bearing the antigen than between the bound antibody (or CH2 or CH3 domain molecule) and cells lacking the antigen. Specific binding typically results in greater than 2-fold, such as greater than 5-fold, greater than 10-fold, or greater than 100-fold increase in amount of bound antibody or CH2 or CH3 domain molecule (per unit time) to a cell or tissue bearing the antigenic polypeptide as compared to a cell or tissue lacking the antigenic polypeptide respectively. Specific binding to a protein under such conditions requires an antibody or CH2 or CH3 domain molecule that is selected for its specificity for a particular protein. A variety of immunoassay formats are appropriate for selecting antibodies or CH2 or CH3 domain molecules specifically immunoreactive with a particular protein. For example, solid-phase ELISA immunoassays are routinely used.

Subject: Living multi-cellular organisms, including vertebrate organisms, a category that includes both human and non-human mammals.

Therapeutically effective amount: A quantity of a specified agent sufficient to achieve a desired effect in a subject being treated with that agent. Such agents include the CH2 or CH3 domain molecules described herein. For example, this may be the amount of an H1V-specific CH2 domain molecule useful in preventing, treating or ameliorating infection by HIV. Ideally, a therapeutically effective amount of an antibody is an amount sufficient to prevent, treat or ameliorate infection or disease, such as is caused by HIV infection in a subject without causing a substantial cytotoxic effect in the subject. The therapeutically effective amount of an agent useful for preventing, ameliorating, and/or treating a subject will be dependent on the subject being treated, the type and severity of the affliction, and the manner of administration of the therapeutic composition.

Toxin: A molecule that is cytotoxic for a cell. Toxins include, but are not limited to, abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (for example, domain Ia of PE or the B chain of DT) and replacing it with a different targeting moiety, such as a CH2 or CH3 domain molecule.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Tumor-associated antigens (TAAs): A tumor antigen which can stimulate tumor-specific T-cell-defined immune responses. Exemplary TAAs include, but are not limited to, RAGE-1, tyrosinase, MAGE-1, MAGE-2, NY-ESO-1, Melan-A/MART-1, glycoprotein (gp) 75, gp100, beta-catenin, PRAME, MUM-1, WT-1, CEA, and PR-1. Additional TAAs are known in the art (for example see Novellino et al., *Cancer Immunol. Immunother.* 54(3):187-207, 2005) and includes TAAs not yet identified.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Viral-associated antigen (VAAs): A viral antigen which can stimulate viral-specific T-cell-defined immune responses. Exemplary VAAs include, but are not limited to, an antigen from human immunodeficiency virus (HIV), BK virus, JC virus, Epstein-Barr virus (EBV), cytomegalovirus (CMV), adenovirus, respiratory syncytial virus (RSV), herpes simplex virus 6 (HSV-6), parainfluenza 3, or influenza B.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Figure 1A:
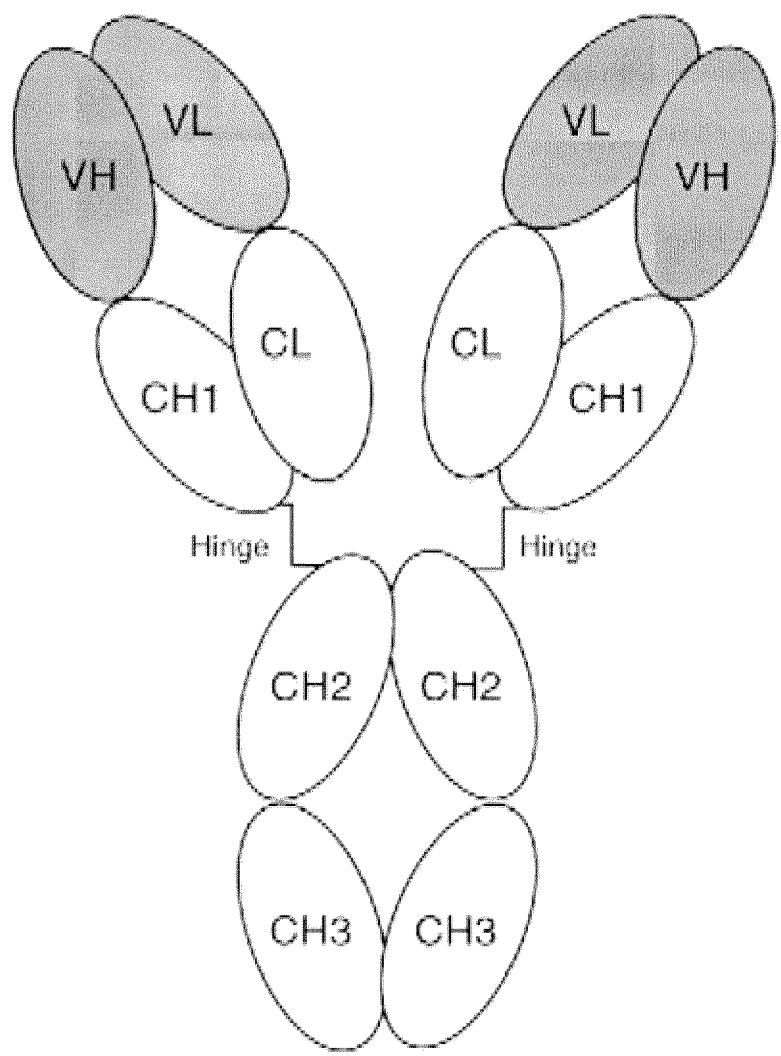

Conventional antibodies are large multi-subunit protein complexes comprising at least four polypeptide chains, including two light chains and two heavy chains (see FIG. 1A for a schematic drawing of a conventional immunoglobulin molecule). The heavy and light chains of antibodies contain variable regions, which bind antigen, and constant regions (such as CH1, CH2 and CH3 domains), which provide structural support and effector functions. The antigen binding region comprises two separate domains, a heavy chain variable domain ($V_H$) and a light chain variable domain ($V_L$). A typical antibody, such as an IgG molecule, has a molecular weight of approximately 150 kD. A number of smaller antigen binding fragments of naturally occurring antibodies have been identified following protease digestion (for example, Fab, Fab', and F(ab')$_2$). These antibody fragments have a molecular weight ranging from approximately 50 to 100 kD. Recombinant methods have been used to generate alternative antigen-binding fragments, termed single chain variable fragments (scFv), which consist of $V_L$ and $V_H$ joined by a synthetic peptide linker. A scFv molecule has a molecular weight of approximately 25-30 kD.

However, in some cases, therapeutic use of antibodies or antibody fragments can be limited due to the size of the antibody. For example, if an antibody or antibody fragment is too large, tissue penetration and epitope access may be restricted. In addition, many therapeutic antibodies are of non-human origin, which can result in toxicity in a human subject. Given these limitations, small, human antibodies that can specifically bind antigen are desirable for diagnostic or therapeutic applications that utilize antibodies or their fragments.

Described herein are engineered antibody constant domain molecules. Disclosed herein are recombinant CH2 and CH3 domain molecules that serve as scaffolds for the introduction of mutations to confer antigen binding to the molecule. Also provided are the modified CH2 and CH3 domain molecules that specifically bind antigen. In some embodiments, the antibody constant domain is a CH2 domain from IgG, IgA or IgD. In other embodiments, the antibody constant domain is a CH3 domain from IgE or IgM. The disclosed CH2 and CH3 domain molecules are small, stable, soluble, have minimal to no toxicity and in some cases, are capable of binding antigen. The CH2 and CH3 domain molecules described herein do not comprise more than one constant domain and do not comprise immunoglobulin variable domains.

Provided herein are polypeptides comprising an immunoglobulin CH2 or CH3 domain, wherein the CH2 or CH3 domain comprises at least one complementarity determining region (CDR), or a functional fragment thereof (such as a SDR), from a heterologous immunoglobulin variable domain. Also provided are CH2 or CH3 domain molecules comprising at least one mutation, such as 1, 2, 3, 4, 5, 6, 7, 8, 9, 10 or more mutations in one or more loops of the CH2 or CH3 domain. The CH2 or CH3 domain molecules described herein have a molecular weight of less than about 15 kD. In some embodiments, the CH2 or CH3 domain molecules have a molecular weight of about 12 to about 14 kD. In some embodiments, the CH2 or CH3 domains comprise an N-terminal truncation of about 1 to about 7 amino acids, such as 1, 2, 3, 4, 5, 6 or 7 amino acids. In some embodiments, the CH2 or CH3 domain molecules comprise a C-terminal truncation of about 1 to about 4 amino acids, such as 1, 2, 3 or 4 amino acids.

Introduction of specific mutations and/or engraftment of the heterologous CDR to the CH2 or CH3 domain enables the polypeptide to bind antigen. In some embodiments, the engrafted portion from the heterologous immunoglobulin comprises only a CDR, or functional fragment thereof. In other embodiments, the engrafted portion comprises additional sequence, such as all or a portion of the hypervariable loop. The length of the engrafted portion can vary, but is typically between 5 and 21 amino acids, including 5, 6, 7, 8, 9, 10, 11, 12, 13, 14, 15, 16, 17, 18, 19, 20 or 21 amino acids. In one embodiment, the engrafted portion is between 8 and 15 amino acids. Although the length of the engrafted portion varies, the resulting CH2 or CH3 domain molecule specifically binds antigen. In some embodiments, the CH2 or CH3 domain molecules specifically binds an antigen with a $K_d$ of about $10^{-6}$, about $10^{-7}$ or about $10^{-8}$ M. In some embodiments, the polypeptide comprises more than one CDR, or functional fragment thereof, such as two or three CDRs.

In some embodiments, at least a portion of a loop region of the CH2 or CH3 domain is replaced by the CDR or functional fragment thereof. The number of amino acids removed from the loop region can vary. In some embodiments, the number of amino acids removed from the loop region is between 1 and 10 amino acids, including 1, 2, 3, 4, 5, 6, 7, 8, 9 or 10 amino acids. In other embodiments, the CDR is engrafted without removing amino acids from the loop region. The number of amino acids removed from the CH2 or CH3 domain loop or loops can vary. One of skill in the art is capable of determining the appropriate sequence to remove empirically, such as by testing the CH2 or CH3 domain molecules for stability, solubility and the capacity to bind an antigen of interest.

The particular CDR engrafted can be any CDR from any immunoglobulin variable domain, such as a $V_H$ domain or a $V_L$ domain. In one embodiment, the CDR is CDR1. In another embodiment, the CDR is CDR2. In another embodiment, the CDR is CDR3. In other embodiments, two or three or more CDRs are engrafted in the loops of the CH2 or CH3 domain molecule.

The CH2 or CH3 domain loop replaced by the CDR (or the CH2 domain into which the CDR is engrafted, without removal of loop sequence) can be any loop of the CH2 or CH3 domain. In one embodiment, the loop region is selected from Loop 1, Loop 2, Loop 3, Loop A-B, Loop C-D or Loop E-F. Any loop of the CH2 or CH3 domain can be replaced by any CDR. In addition, multiple loops can be replaced by CDRS, in any combination. In one embodiment, Loop 1 is replaced by CDR1 or CDR3. In another embodiment, Loop 3 is replaced by CDR1 or CDR3. In another embodiment, Loop 1 and Loop 3 are replaced by CDR1 and CDR3, respectively. In another embodiment, Loop 1 and Loop 3 are replaced by CDR3 and CDR1, respectively. In other embodiments, Loop A-B is replaced by CDR1; Loop C-D is replaced by CDR2; or Loop E-F is replaced by CDR3.

In preferred embodiments, the polypeptides provided herein do not comprise a variable domain, such as a $V_H$ domain or a $V_L$ domain.

The antibody constant domain can be derived from any type of immunoglobulin. In one embodiment, the immunoglobulin is an IgG. In other embodiments, the immunoglobulin is an IgA, IgD, IgM or IgE. In particular examples, the constant domain is a CH2 domain from IgG.

In some embodiments, the CH2 or CH3 domains that bind antigen have additional mutations that increase stability of the molecule. For example, the molecules can comprise mutations that allow for the formation of non-native disulfide bonds, such as by introducing a pair of amino acid substitutions to replace original residues with cysteine residues. In some examples, a first amino acid substitution is introduced in the N-terminal A strand and the second amino acid substitution is introduced in the C-terminal G strand of the constant domain In addition, the antigen binding CH2 and CH3 domain molecules can be either glycosylated or unglycosylated.

Also provided herein are polypeptides comprising an immunoglobulin CH2 domain of IgG, Ig or IgD, or a CH3 domain of IgE and IgM, wherein the CH2 domain or CH3 domain comprises a first amino acid substitution and a second amino acid substitution, wherein the first and second amino acid substitutions each replace the original residue with a cysteine residue, wherein the cysteine residues form a disulfide bond, and wherein the polypeptide has a molecular weight of less than about 15 kD. Such CH2 and CH3 domains exhibit increased stability relative to unmodified CH2 and CH3 domains, and thus are useful as scaffolds for introducing mutations to confer antigen binding to the CH2 or CH3 domain.

In some embodiments, the first amino acid substitution is in the N-terminal A strand and the second amino acid substitution is in the C-terminal G strand, which allows formation of a disulfide bond between the A and G strands (see FIGS. 3A-3C for a schematic of the loop regions). In some examples, the constant domain is a CH2 domain of IgG.

In particular examples described herein, the first amino acid substitution is L12 to C12 and the second amino acid substitution is K104 to C104 (numbered with reference to SEQ ID NO: 5). In other examples, the first amino acid substitution is V10 to C10 and the second amino acid substitution is K104 to C104 (numbered with reference to SEQ ID NO: 5).

The CH2 and CH3 domain scaffold can comprise additional mutations, such as to increase stability or enhance solubility and expression. In some embodiments, the CH2 or CH3 domain comprises an N-terminal truncation of about 1 to about 7 amino acids. In particular examples, the N-terminal truncation is 1, 2, 3, 4, 5, 6 or 7 amino acids in length. In some embodiments, the CH2 or CH3 domain scaffold comprises a C-terminal truncation of about 1 to about 4 amino acids. In particular examples, the C-terminal truncation is 1, 2, 3 or 4 amino acids.

In some embodiments, the CH2 or CH3 domain scaffold is further mutated to confer antigen binding. In particular embodiments, (i) at least one of the loops of the CH2 or CH3 domain is mutated; (ii) at least a portion of a loop region of the CH2 or CH3 domain is replaced by a CDR or fragment thereof from a heterologous immunoglobulin variable domain; or (iii) both.

In addition, the CH2 domain or CH3 domain can either be unglycosylated or glycosylated. For example, a recombinant CH2 or CH3 domain can be expressed in a mammalian cell to allow for post-translational modifications, such as glycosylation.

In some embodiments, the antigen is from a pathogen, such as a virus or bacterium. In one embodiment, the pathogen is HIV. In other embodiments, the antigen is a cancer-specific antigen or a cancer-related protein. In other embodiments, the antigen is related to an autoimmune disease (for example, TNF-α).

In some embodiments, the CH2 or CH3 domain molecule binds a tumor antigen. The tumor antigen can be any tumor-associated antigen, which are well known in the art.

Also provided herein are compositions comprising the CH2 or CH3 domain molecules described herein. In some embodiments, the composition comprises a CH2 domain or CH3 domain and a pharmaceutically acceptable carrier.

Nucleic acid molecules encoding the disclosed CH2 or CH3 domain molecules, vectors comprising the nucleic acid sequences, and cells comprising the vectors are also provided herein.

In some embodiments, engineered CH2 or CH3 domain molecules comprise Fc receptor binding sites and are capable of binding at least one Fc receptor. In particular examples, the Fc receptor is the neonatal Fc receptor. The ability to bind an Fc receptor confers effector functions to the CH2 or CH3 domain molecule, such as, for example, ADCC. In other embodiments, engineered CH2 or CH3 domains bind complement-related molecules, such as C1q, which can activate the compliment system. In yet other embodiments, the CH2 or CH3 domain molecules are conjugated to an effector molecule, which include, but are not limited to, therapeutic, diagnostic, or detection moieties.

Further provided are methods of use of the CH2 or CH3 domain molecules for the preparation of a medicament. In one embodiment, the medicament is for the treatment of HIV infection. In another embodiment, the medicament is for the treatment of cancer. In another embodiment, the medicament is for the treatment of an autoimmune or inflammatory disorder.

The CH2 and CH3 domain molecules described herein can be engineered to specifically bind any desired antigen. Methods of identifying and selecting antigen-specific CH2 or CH3 domain molecules can be achieved using any suitable technique known in the art, such as by using a phage display library.

Provided herein is a method of identifying a recombinant CH2 domain or CH3 domain that specifically binds a target antigen. The method includes (a) providing a library of particles displaying on their surface a recombinant CH2 or CH3 domain, wherein the CH2 or CH3 domain has a molecular weight less than about 15 kD; (b) contacting the library of particles with the target antigen to select particles that specifically bind the target antigen; and (c) cloning the CH2 or CH3 domain nucleic acid molecules from the particles expressing the CH2 or CH3 domains that specifically bind the target antigen, thereby identifying a CH2 or CH3 domain that specifically binds the target antigen. In some embodiments, the library is generated by (i) providing a library of nucleic acid molecules encoding a genetically diverse population of CH2 or CH3 domains, wherein the genetically diverse population is provided by introducing mutations into one or more loop regions of the CH2 or CH3 domain; and (ii) expressing the library of nucleic acid molecules in recombinant host cells, whereby the CH2 domains or CH3 domains are expressed on the surface of the particles and the CH2 or CH3 domain nucleic acid molecules are encoded by the genetic material of the particles. In some embodiments, the CH2 or CH3 domain comprises an N-terminal deletion of about 1 to about 7 amino acids. In some embodiments, the particles are phage particles.

In some embodiments, the phage library expresses recombinant CH2 domains, such as IgG CH2 domains. In some embodiments, the CH2 domain or CH3 domains comprise at least one mutation in Loop 1, or at least one mutation in Loop 2, or at least one mutation in Loop 3, or at least one mutation in Loop A-b, or at least one mutation in Loop C-D, or at least one mutation in Loop E-F, or any combination thereof.

Any suitable recombinant host cell can be used to generate phage particles. Such host cells are well known in the art. In some examples, the recombinant host cells are TG1 cells.

Further provided herein is a method of making a library of recombinant CH2 or CH3 domains, comprising (i) introducing mutations into one or more loop regions of a CH2 domain or CH3 domain scaffold, or (ii) replacing a portion of a loop region of the CH2 domain or CH3 domain scaffold with a CDR or functional fragment thereof from a heterologous immunoglobulin variable domain, or (iii) both, wherein the scaffold comprises an isolated immunoglobulin CH2 domain of IgG, IgA or IgD or CH3 domain of IgE or IgM.

In some embodiments, the CH2 or CH3 domain scaffold further comprises an N-terminal truncation of about 1 to about 7 amino acids, such as about 1, 2, 3, 4, 5, 6 or 7 amino acids. In some embodiments, the CH2 or CH3 domain scaffold further comprises a C-terminal truncation of about 1 to about 4 amino acids, such as about 1, 2, 3 or 4 amino acids.

In some cases, the CH2 or CH3 domain scaffold further comprises additional mutations to stabilize the molecule. In some embodiments of the method, the CH2 or CH3 domain scaffold further comprises a first amino acid substitution and a second amino acid substitution, wherein the first and second amino acid substitutions each replace the original residue with a cysteine residue, wherein the cysteine residues form a disulfide bond.

Further provided is a method of identifying a recombinant CH2 domain or CH3 domain that specifically binds a target antigen, comprising contacting the library produced by the methods disclosed herein with the target antigen to select recombinant CH2 or CH3 domains that specifically bind the target antigen.

Also provided are libraries, such as phage-displayed libraries, of CH2 or CH3 domain molecules. The libraries comprise CH2 or CH3 domain molecules having one or more mutations, engrafted CDRs, hypervariable loops, or functional fragments thereof. The libraries comprising mutated residues can be used to identify CH2 or CH3 domain molecules having a desired antigen binding affinity and/or to identify CH2 or CH3 domain molecules with reduced immunogenicity.

Further provided are kits comprising the CH2 or CH3 domain molecules disclosed herein. In one embodiment, the CH2 or CH3 domain molecule is labeled (such as with a fluorescent, radioactive, or an enzymatic label). In another embodiment, a kit includes instructional materials disclosing means of use of a CH2 or CH3 domain molecule. The instructional materials may be written, in an electronic form (for example computer diskette or compact disk) or may be visual (such as video files). The kits can also include additional components to facilitate the particular application for which the kit is designed. Thus, for example, the kit can additionally contain means of detecting a label (such as enzyme substrates for enzymatic labels, filter sets to detect fluorescent labels, appropriate secondary labels such as a secondary antibody, or the like). The kits can additionally include buffers and other reagents routinely used for the practice of a particular method. Such kits and appropriate contents are well known to those of skill in the art.

IV. Engineered Antibody Constant Domains

The engineered antibody constant domain molecules described herein are small in size (typically less than 15 kD), which offers significant advantages for detection, diagnosis and treatment. For example, the small size of the molecules allows for greater epitope access and better tissue penetration. As shown in FIG. 5C, the CH2 domain antibodies provided herein have a lower molecular weight than other types of antibodies and antibody fragments, such as scFv, Fab and IgG molecules. They are also smaller than $V_H$ domain antibodies.

As described herein, the CH2 or CH3 domain molecules can effectively bind antigen in the absence of other immunoglobulin domains, including variable domains or other constant domains. For example, the CH2 or CH3 domain molecules can specifically bind an antigen with a kD of about $10^{-6}$, about $10^{-7}$, about $10^{-8}$ or about $10^{-9}$ or less.

The CH2 or CH3 domains described herein that specifically bind an antigen comprise at least one heterologous amino acid sequence from an immunoglobulin variable domain, and/or comprise at least one mutation. The heterologous amino acid sequence engrafted in the CH2 or CH3 domain comprises at least one CDR, or functional fragment thereof (such as an SDR from an antibody that specifically binds an antigen of interest). The engrafted amino acid sequence can also contain additional amino acid sequence extending from the CDR toward the N-terminus and/or toward the C-terminus, such as other amino acids comprising the hypervariable loop. Thus, in some embodiments, the engineered CH2 or CH3 domain molecules comprise a complete hypervariable loop from a heterologous immunoglobulin variable domain. The engineered CH2 and CH3 domains can further comprise second or third CDRs or hypervariable loops. The length of the engrafted CDR or hypervariable loop can vary. Appropriate lengths can be determined empirically, such as by expressing the engineered CH2 or CH3 domains and assessing stability and solubility of the protein, as well as by determining binding affinity. Methods of protein expression, determining protein solubility and evaluating antigen binding affinity are well known in the art. As described herein, it has been determined that sequences up to 21 amino acids in length can be successfully engrafted in the CH2 domain.

A human CH2 domain comprises six loop regions: Loop 1, Loop 2, Loop 3, Loop A-B, Loop C-D and Loop E-F. CDRs and/or hypervariable loops from a heterologous immunoglobulin variable domain can be engrafted in one or more of any of these loops, in any combination (see FIGS. 5A-5C for examples).

The amino acid sequence of the human γ1 CH2 domain is set forth as SEQ ID NO: 5. The amino acid residues comprising each of the loop regions is shown below in Table 1. The amino acid positions are numbered starting with number 1 for the first residue of the CH2.

TABLE 1

Amino Acid Positions of CH2 Domain Loops

| Loop | Amino acid positions (SEQ ID NO: 5) |
| --- | --- |
| Loop A-B | 14-27 |
| Loop 1 | 35-43 |
| Loop C-D | 54-62 |
| Loop 2 | 67-69 |
| Loop E-F | 78-88 |
| Loop 3 | 96-100 |

The amino acid sequence of the human $V_H$ domain is shown in FIG. 1B, and set forth as SEQ ID NO: 1. The amino acid residues comprising each CDR and hypervariable loop is shown below in Table 2.

TABLE 2

Amino Acid Positions of Hypervariable Loops

| CDR/Loop | Amino acid positions (SEQ ID NO: 1) |
| --- | --- |
| H1/CDR1 | 27-36 |
| H2/CDR2 | 50-68 |
| H3/CDR3 | 99-109 |

In one exemplary embodiment, nine amino acids from Loop 1 of the CH2 domain are replaced with 10 amino acids from hypervariable loop H1/CDR1 from the $V_H$ domain of a human antibody. In other exemplary embodiments, six amino acids from Loop 3 of the CH2 domain are replaced with twelve or thirteen amino acids from hypervariable loop H3/CDR3 of the $V_H$ domain of a human antibody. In another exemplary embodiment, six amino acids from Loop 3 of the CH2 domain are replaced with 10 amino acids from hypervariable loop H1/CDR1 from the $V_H$ domain of a human antibody. In other exemplary embodiments, nine amino acids from Loop 1 of the CH2 domain are replaced with twelve or thirteen amino acids from hypervariable loop H3/CDR3 of the $V_H$ domain of a human antibody.

In other embodiments, 0, 1, 2, 3, 4, 5, 6, 7, 8, 9 or 10 amino acids of one or more of Loops 1, 2, 3, A-B, C-D or E-F are replaced with 5, 6, 7, 8, 9, 10, 11, 12, 13, 14, 15, 16, 17, 18, 19, 20 or 21 amino acids of one or more CDRs or hypervariable loops from a heterologous antibody, in any combination. The CDR or hypervariable loops can be from a $V_L$ or a $V_H$ domain (see FIGS. 3A-3C).

The engrafted hypervariable loop(s) or CDR(s) can be from any antibody of interest. Such antibodies include, but are not limited to, pathogen-specific antibodies and cancer-specific antibodies. Pathogen-specific antibodies, include for example, antibodies that specifically bind an antigen from a pathogen such as viruses, bacteria or fungi, protozoa or parasites. In one exemplary embodiment, the antibody specifically binds HIV-1. Cancer-specific antibodies include antibodies that specifically recognize antigen expressed (such as on the cell surface) by the cancer cell, but not by other non-cancer cells. Examples of cancer-specific antibodies, include, but are not limited to, antibodies that recognize lung cancer, breast cancer, prostate cancer, liver cancer, bladder cancer, thyroid cancer, kidney cancer, pancreatic cancer, colorectal cancer, skin cancer, melanoma, neuroblastoma, Ewing's sarcoma, leukemia or lymphoma cells or tissue.

In some embodiments, the engineered CH2 or CH3 domain molecules comprise CDR/hypervariable sequence with a known specificity. Alternatively, the engineered CH2 domain molecules can comprise randomized CDR peptide sequence or sequences. Mutational analysis of the CDRs can be performed to identify CH2 domain molecules having increased binding affinity and/or decreased immunogenicity. In addition, libraries of CH2 or CH3 domain molecules comprising randomized or mutated CDR peptide sequences can be generated to identify CH2 or CH3 domain molecules that bind with high affinity to a particular antigen of interest, such as described below.

The CH2 and CH3 domain molecules provided herein can further comprise effector molecules, such as for therapeutic, diagnostic or detection purposes. For example, effector molecules can include toxins and detectable labels, such as radiolabels, enzymes or fluorescent markers. Additional details on the types of effector molecules that can be used with CH2 and CH3 domain molecules is described below (see "Effector Functions of Antibody Constant Domain Molecules").

V. Antibody Constant Domain Molecule Libraries

Further provided herein are libraries of engineered CH2 or CH3 domain molecules comprising randomly inserted or mutated CDR amino acid sequences. The libraries can be used to screen for CH2 or CH3 domain molecules having high affinity for a particular antigen of interest. In one embodiment, the libraries are phage display libraries. Antibody phage display libraries, and methods of generating such libraries, are well known in the art (see, for example, U.S. Pat. Nos. 6,828,422 and 7,195,866, incorporated herein by reference).

The development of libraries of polypeptides, including antibodies, has been described (U.S. Pat. No. 6,828,422). To generate a library of polypeptides (such as a library of CH2 or CH3 domain molecules), nucleic acid sequences suitable for the creation of the libraries must first be generated. To generate such randomized nucleic acid sequences, typically error-prone PCR is used. Mutations are introduced randomly in at least one of the loops. For example, a collection (such as two or three or more) of homologous proteins is identified, a database of the protein sequences is established and the protein sequences are aligned to each other. In the case of CH2 domain molecules, a collection of human CH2 domain sequences are identified and used to create the database. The database is used to define subgroups of protein sequences which demonstrate a high degree of similarity in the sequence and/or structural arrangement. For each of the subgroups, a polypeptide sequence comprising at least one consensus sequence is deduced which represents the members of this subgroup (such as a subgroup of CH2 domains). The complete collection of polypeptide sequences represents the complete structural repertoire of the collection of homologous proteins (the CH2 domains). These artificial polypeptide sequences can be analyzed according to their structural properties to identify unfavorable interactions between amino acids within the polypeptide sequences or between the polypeptide sequences and other polypeptide sequences. Such interactions can be removed by changing the consensus sequence accordingly.

Next, the polypeptide sequences are analyzed to identify sub-elements, including domains, loops, β-sheets, α-helices and/or CDRs. The amino acid sequence is back translated into a corresponding coding nucleic acid sequence which is adapted to the codon usage of the host planned for expressing the described nucleic acid sequences. A set of cleavage sites is set up such that each of the sub-sequences encoding the sub-elements identified as described above, is flanked by two sites which do not occur a second time within the nucleic acid sequence. This can be achieved by either identifying a cleavage site already flanking a sub-sequence or by changing one or more nucleotides to create the cleavage site, and by removing that site from the remaining part of the gene. The cleavage sites should be common to all corresponding sub-elements or sub-sequences, which allows for the creation of a fully modular arrangement of the sub-sequences in the nucleic acid sequence and of the sub-elements in the corresponding polypeptide.

The nucleic acid sequences described above are synthesized using any one of several methods well known in the art, such as, for example, by total gene synthesis or by PCR-based approaches.

In one embodiment, the nucleic acid sequences are cloned into a vector. The vector can be a sequencing vector, an expression vector or a display vector (such as a phage display), which are well known in the art. Vectors can comprise one nucleic acid sequence, or two or more nucleic sequences, either in a different or the same operon. If in the same operon, the nucleic acid sequences can be cloned separately or as contiguous sequences.

In one embodiment, one or more sub-sequences (such as a loop) of the nucleic acid sequences are replaced by different sequences. This can be achieved by excising the sub-sequences using the cleavage sites adjacent to or at the end of the sub-sequence, such as by an appropriate restriction enzyme, and replacing the sub-sequence by a different sequence compatible with the cleaved nucleic acid sequence. In a further embodiment, the different sequences replacing the initial sub-sequence(s) (also referred to as "engrafted sequences") are genomic or rearranged genomic sequences, for example CDRs, SDRs or hypervariable loops from a heterologous antibody. In some embodiments, the heterologous sequences are random sequences. The introduction of random sequences introduces variability into the polypeptides (or CH2 domain molecules) to create a library. The random sequences can be generated using any of a number of methods well known in the art, such as by using a mixture of mono- or tri-nucleotides during automated oligonucleotide synthesis or by error-prone PCR. The random sequences can be completely randomized or biased toward or against certain codons according to the amino acid distribution at certain positions in known protein sequences. Additionally, the collection of random sub-sequences can comprise different numbers of codons, giving rise to a collection of sub-elements having different lengths.

The nucleic acid sequences can be expressed from a suitable vector under appropriate conditions well known in the art. In one embodiment, the polypeptides expressed from the nucleic acid sequences are screened. The polypeptides can further be optimized. Screening can be performed by using any method well known in the art, such as phage-display, selectively infective phage, polysome technology to screen for binding, assay systems for enzymatic activity or protein stability. Polypeptides (such as CH2 domain molecules) having the desired property can be identified by sequencing the nucleic acid sequence or amino acid sequence, or by mass spectrometry. The desired property the polypeptides are screened for can be, for example, optimized affinity or specificity for a target molecule.

In some embodiments, phagemid vectors can be used to simultaneously express a large number of nucleic acid sequences, such as those encoding a library of CH2 or CH3 domain molecules (see, for example, U.S. Patent Application Publication No. 2008/0312101). The libraries of phage particles expressing CH2 and CH3 domains can be screened using any screening assay known to be applicable with phage.

For example, the phage can be exposed to a purified antigen, soluble or immobilized (e.g. on a plate or on beads) or exposed to whole cells, tissues, or animals, in order to identify phage that adhere to targets present in complex structures, and in particular in physiologically or therapeutically relevant locations (e.g. binding to cancer cells or to an antigen on a viral particle).

The selected phagemid vectors in which a heterologous sequence has been cloned, expressed, and specifically isolated on the basis of its binding for a specific ligand, can be extracted from the bacterial cells, and sequenced, PCR-amplified, and/or recloned into another appropriate vector, for example for the large scale recombinant production in bacterial, plant, yeast, or mammalian cells.

The detection of the interaction with the specific target antigen can be performed by applying standard panning methods, or by applying more sophisticated biophysical technologies for assessment of interactions between the displayed CH2 or CH3 binding molecule and its target antigen, such as fluorescence-based spectroscopy or microscopy, phosphatase reaction, or other high-throughput technologies.

Once CH2 or CH3 domain-expressing phage particles that specifically bind a target antigen have been selected, the recombinant phage and the relevant DNA sequence can be isolated and characterized according to the methods known in the art (e.g. separated from the phagemid vector using restriction enzymes, directly sequenced, and/or amplified by PCR). These sequences can be then transferred into more appropriate vectors for further modification and/or expression into prokaryotic or eukaryotic host cells. The DNA sequence coding for the CH2 or CH3 domain, once inserted into a suitable vector, can be introduced into appropriate host cells by any suitable means (transformation, transfection, conjugation, protoplast fusion, electroporation, calcium phosphate precipitation, direct microinjection, etc.) to transform the cells.

This collection of DNA molecules can then be used to create libraries of CH2 or CH3 domain molecules. The affinity of the CH2 or CH3 domain molecules can be optimized using the methods described above. The libraries can be used to identify one or more CH2 or CH3 domain molecules that bind to a target. Identification of the desired CH2 or CH3 domain molecules comprises expressing the CH2 or CH3 domain molecules and then screening them to isolate one or more molecules that bind to a given target molecule with the desired affinity. If necessary, the modular design of the DNA molecules allows for excision of one or more genetic subsequences and replacement with one or more second subsequences encoding structural sub-elements. The expression and screening steps can then be repeated until a CH2 or CH3 domain molecule having the desired affinity is generated.

In one embodiment is a method in which one or more of the genetic subunits (for example, one or more CH2 or CH3 domain loop regions) are replaced by a random collection of sequences (the library) using the cleavage sites. The resulting library is then screened against any chosen antigen. CH2 or CH3 domain molecules with the desired properties (such as having the desired binding affinity) are selected, collected and can be used as starting material for the next library.

In another embodiment, fusion proteins can be generated by providing a DNA sequence which encodes both the polypeptide, as described above, and an additional moiety. Such moieties include immunotoxins, enzymes, effector molecules, therapeutic molecules, labels or tags (such as for detection and/or purification).

Also provided herein are the nucleic acid sequences, vectors containing the nucleic acid sequences, host cells containing the vectors, and polypeptides, generated according to the methods described above.

Further provided are kits comprising one or more of the nucleic acid sequences, recombinant vectors, polypeptides, and/or vectors according to the methods described above, and suitable host cells for producing the polypeptides.

VI. Nucleic Acids encoding Antibody Constant Domain Molecules

Nucleic acid sequences encoding the CH2 or CH3 domain molecules and/or immunotoxins can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20): 1859-1862, 1981, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding a CH2 or CH3 domain molecule, or an immunotoxin including a CH2 or CH3 domain molecule, can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, a CH2 domain molecule of use is prepared by inserting the cDNA which encodes the CH2 domain molecule into a vector which comprises the cDNA encoding an effector molecule (EM). The insertion is made so that the variable region and the EM are read in frame so that one continuous polypeptide is produced. Thus, the encoded polypeptide contains a functional CH2 domain region and a functional EM region. In one embodiment, cDNA encoding an effector molecule, such as, but not limited to a cytotoxin, is ligated to a CH2 domain molecule so that the EM is located at the carboxyl terminus of the CH2 domain molecule. In one example, cDNA encoding a *Pseudomonas* exotoxin ("PE"), mutated to eliminate or to reduce non-specific binding, is ligated to a CH2 domain molecule so that the EM is located at the amino terminus of the CH2 domain molecule Once the nucleic acids encoding the CH2 domain molecule (or immunotoxin) are isolated and cloned, the protein can be expressed in recombinantly engineered cells such as bacteria, plant, yeast, insect or mammalian cells. For example, one or more DNA sequences encoding the CH2 domain molecule can be expressed in vivo by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Alternatively the DNA sequences encoding the immunotoxin, antibody, or fragment thereof can be expressed in vitro.

Polynucleotide sequences encoding the CH2 or CH3 domain molecules can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (such as ATG) in front of a protein-encoding gene, splicing signal for introns, maintenance of the correct reading frame of that gene to permit proper translation of mRNA, and stop codons.

The polynucleotide sequences encoding the CH2 or CH3 domain molecules can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the immunotoxin, antibody, or fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide (such as a CH2 domain molecule) can be carried out by conventional means including preparative chromatography and immunological separations. Once expressed, the recombinantly expressed polypeptide can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of a protein and/or refolding to an appropriate active form, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Renaturation can be accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

In addition to recombinant methods, the CH2 and CH3 domain molecule disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol.* 2: *Special Methods in Peptide Synthesis, Part A*. pp. 3-284; Merrifield et al., *J. Am. Chem. Soc.* 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are well known in the art.

VII. Use of Antibody Constant Domain Molecules for Diagnosis or Treatment

CH2 and CH3 domain molecules have enormous potential for diagnosis and/or treatment of any of a number of diseases or conditions for which an antibody is of use. For example, CH2 or CH3 domain molecules can be used for the treatment of cancer, infectious disease (such as viral, bacterial, fungal or parasitic infections), autoimmune disease, inflammatory disorders, or any other disease or condition for which antibodies or their fragments can be used as therapeutic agents.

In some embodiments, the infectious disease caused by a virus, such as a virus from one of the following families: *Retroviridae* (for example, human immunodeficiency virus (HIV); human T-cell leukemia viruses (HTLV); *Picornaviridae* (for example, polio virus, hepatitis A virus; hepatitis C virus; enteroviruses, human coxsackie viruses, rhinoviruses, echoviruses; foot-and-mouth disease virus); *Calciviridae* (such as strains that cause gastroenteritis); *Togaviridae* (for example, equine encephalitis viruses, rubella viruses); *Flaviridae* (for example, dengue viruses; yellow fever viruses; West Nile virus; St. Louis encephalitis virus; Japanese encephalitis virus; and other encephalitis viruses); *Coronaviridae* (for example, coronaviruses; severe acute respiratory syndrome (SARS) virus; *Rhabdoviridae* (for example, vesicular stomatitis viruses, rabies viruses); *Filoviridae* (for example, Ebola viruses); *Paramyxoviridae* (for example, parainfluenza viruses, mumps virus, measles virus, respiratory syncytial virus (RSV)); *Orthomyxoviridae* (for example, influenza viruses); *Bunyaviridae* (for example, Hantaan viruses; Sin Nombre virus, Rift Valley fever virus; bunya viruses, phleboviruses and Nairo viruses); *Arena viridae* (hemorrhagic fever viruses; Machupo virus; Junin virus); *Reoviridae* (e.g., reoviruses, orbiviurses and rotaviruses); Birnaviridae; *Hepadnaviridae* (Hepatitis B virus); *Parvoviridae* (parvoviruses); *Papovaviridae* (papilloma viruses, polyoma viruses; BK-virus); *Adenoviridae* (most adenoviruses); *Herpesviridae* (herpes simplex virus (HSV)-1 and HSV-2; cytomegalovirus (CMV); Epstein-Barr virus (EBV); varicella zoster virus (VZV); and other herpes viruses, including HSV-6); *Poxyiridae* (variola viruses, vaccinia viruses, pox viruses); and *Iridoviridae* (such as African swine fever virus); *Filoviridae* (for example, Ebola virus; Marburg virus); *Caliciviridae* (for example, Norwalk viruses) and unclassified viruses (for example, the etiological agents of Spongiform encephalopathies, the agent of delta hepatitis (thought to be a defective satellite of hepatitis B virus); and astroviruses).

In other embodiments, the infectious disease is caused by a type of bacteria, such as *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, or *Actinomyces israelli*.

In other embodiments, the infectious disease is caused by a fungus, such as *Cryptococcus neoformans, Histoplasma capsulatum, Coccidioides immitis, Blastomyces dermatitidis, Chlamydia trachomatis*, or *Candida albicans*. In other embodiments, the infectious disease is caused by a parasite, such as *Plasmodium falciparum* or *Toxoplasma gondii*.

In some embodiments, the cancer is a solid tumor or a hematogenous cancer. In particular examples, the solid tumor is a sarcoma or a carcinoma, such as fibrosarcoma, myxosarcoma, liposarcoma, chondrosarcoma, osteogenic sarcoma, or another sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, or a CNS tumor (such as a glioma, astrocytoma, medulloblastoma, craniopharyogioma, ependymoma, pinealoma, hemangioblastoma, acoustic neuroma, oligodendroglioma, menangioma, melanoma, neuroblastoma or retinoblastoma).

In some examples, the hematogenous cancer is a leukemia, such as an acute leukemia (such as acute lymphocytic leukemia, acute myelocytic leukemia, acute myelogenous leukemia and myeloblastic, promyelocytic, myelomonocytic, monocytic and erythroleukemia); a chronic leukemia (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia or myelodysplasia.

In some embodiments, the CH2 or CH3 domain molecule specifically binds a tumor antigen. Tumor antigens are well known in the art and include, for example, carcinoembryonic antigen (CEA), β-human chorionic gonadotropin β-HCG), alpha-fetoprotein (AFP), lectin-reactive AFP, (AFP-L3), thyroglobulin, RAGE-1, MN-CA IX, human telomerase reverse transcriptase (hTERT), RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), melanoma-associated antigen (MAGE), ELF2M, neutrophil elastase, ephrinB2 and CD22. The CH2 or CH3 domain molecules can also bind any cancer-related proteins, such IGF-I, IGF-II, IGR-IR or mesothelin. Additional tumor associated antigens are provided below in Table 3.

TABLE 3

Exemplary tumors and their tumor antigens

| Tumor | Tumor Associated Target Antigens |
|---|---|
| Acute myelogenous leukemia | Wilms tumor 1 (WT1), preferentially expressed antigen of melanoma (PRAME), PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | New York esophageous 1 (NY-Eso1) |
| Malignant melanoma | MAGE, MART, Tyrosinase, PRAME GP100 |
| Breast cancer | WT1, herceptin |
| Lung cancer | WT1 |
| Prostate cancer | Prostate-specific antigen (PSA) |
| Colon cancer | Carcinoembryonic antigen (CEA) |
| Renal cell carcinoma (RCC) | Fibroblast growth factor 5 (FGF-5) |

In some embodiments, the autoimmune disease is rheumatoid arthritis, juvenile oligoarthritis, collagen-induced arthritis, adjuvant-induced arthritis, Sjögren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia or pernicious anemia.

The wide utility of the CH2 and CH3 domain molecules is due at least in part to their small size, which allows for efficient penetration in tissues, including solid tumors and lymphoid tissue where HIV replicates, and also permits efficient neutralization of viruses (for example, HIV) that rapidly evolve to avoid neutralization by immunoglobulins generated by the host immune system. Engineered CH2 or CH3 domain molecules are also useful for treatment due to their amenability for creating high-affinity binding antibodies to any antigen of interest. Furthermore, as described herein, the CH2 or CH3 domain molecules can further comprise an effector molecule with therapeutic properties (such as, for example, a drug, enzyme or toxin).

As described herein, CH2 or CH3 domain molecules can be engineered to comprise one or more CDRs from an antibody specific for a pathogen, such as HIV. X5 is a neutralizing antibody specific for HIV-1 (Moulard et al. *Proc. Natl. Acad. Sci. U.S.A.* 99:6913-6918, 2002). The neutralizing activity of X5 has been shown to significantly increase when converted from a complete immunoglobulin (IgG1) or a Fab to a scFv antibody, which contains only the variable domains of the heavy and light chains (Labrijn et al. *J. Virol.* 77:10557-10565, 2003). It is believed this effect is due to the size-restricted access to the X5 epitope. CH2 and CH3 domain molecules are smaller than scFv antibodies, leading to the hypothesis that an engineered CH2 domain molecule (comprising one or more X5 CDRs) would have enhanced neutralizing activity due to its ability to access the epitope.

CH2 and CH3 domain molecules are usually administered to a subject as compositions comprising one or more pharmaceutically acceptable carriers. Such carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight, general condition of the subject, the particular bleeding disorder or episode being treated, the particular CH2 or CH3 domain molecule being used and its mode of administration. An appropriate dose can be determined by one of ordinary skill in the art using only routine experimentation.

Provided herein are pharmaceutical compositions which include a therapeutically effective amount of an engineered CH2 or CH3 domain molecule alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

VIII. Use of Antibody Constant Domain Molecules for Detection

Methods of determining the presence or absence of a polypeptide are well known in the art. For example, the specific binding agents, such as a CH2 domain molecule can be conjugated to other compounds including, but not limited to, enzymes, magnetic beads, colloidal magnetic beads, haptens, fluorochromes, metal compounds, radioactive compounds or drugs. The CH2 or CH3 domain molecules can also be utilized in immunoassays such as but not limited to radioimmunoassays (RIAs), enzyme linked immunosorbent assays (ELISA), immunohistochemical assays, Western blot or immunoprecipitation assays. These assays are well known in the art (see Harlow & Lane, *Antibodies, A Laboratory Manual*, Cold Spring Harbor Publications, New York (1988), for a description of immunoassay formats).

In one embodiment, a diagnostic kit comprising an immunoassay is provided. Although the details of the immunoassays may vary with the particular format employed, the method for detecting an antigen in a biological sample generally includes the steps of contacting the biological sample with a CH2 or CH3 domain molecule which specifically reacts, under immunologically reactive conditions, to the antigen of interest. The CH2 or CH3 domain molecule is allowed to specifically bind under immunologically reactive conditions to form an immune complex, and the presence of the immune complex (bound antigen) is detected directly or indirectly.

The CH2 or CH3 domain molecules disclosed herein can also be used for fluorescence activated cell sorting (FACS). A FACS assay employs a plurality of color channels, low angle and obtuse light-scattering detection channels, and impedance channels, among other more sophisticated levels of detection, to separate or sort cells (see U.S. Pat. No. 5,061, 620). FACS can be used to sort cells that are antigen positive, by contacting the cells with an appropriately labeled CH2 or CH3 domain molecule. However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Additional separation procedures may include magnetic separation, using CH2 or CH3 domain molecule-coated magnetic beads, affinity chromatography, cytotoxic agents, either joined to a CH2 or CH3 domain molecule or used in conjunction with complement, and "panning," which utilizes an antibody, or CH2 or CH3 domain molecule, attached to a solid matrix, or another convenient technique. The attachment of specific binding agents to magnetic beads and other solid matrices, such as agarose beads, polystyrene beads, hollow fiber membranes and plastic Petri dishes, allow for direct separation. Cells that are bound by the specific binding agent, such as a CH2 or CH3 domain molecule, can be removed from the cell suspension by simply physically separating the solid support from the cell suspension. The exact conditions and duration of incubation of the cells with the solid phase-linked antibodies, or CH2 or CH3 domain molecules, will depend upon several factors specific to the system employed. The selection of appropriate conditions, however, is well known in the art.

Unbound cells then can be eluted or washed away with physiologic buffer after sufficient time has been allowed for the cells expressing an antigen of interest to bind to the solid-phase linked binding agent. The bound cells are then separated from the solid phase by any appropriate method, depending mainly upon the nature of the solid phase and the antibody or CH2 or CH3 domain molecule employed, and quantified using methods well known in the art. In one specific, non-limiting example, bound cells separated from the solid phase are quantified by FACS.

CH2 or CH3 domain molecules may be conjugated to biotin, which then can be removed with avidin or streptavidin bound to a support, or fluorochromes, which can be used with FACS to enable cell separation and quantitation, as known in the art.

CH2 or CH3 domain molecules can be conjugated to other compounds including, but not limited to, enzymes, paramagnetic beads, colloidal paramagnetic beads, haptens, fluorochromes, metal compounds, radioactive compounds or drugs. The enzymes that can be conjugated to the CH2 or CH3 domain molecules include, but are not limited to, alkaline phosphatase, peroxidase, urease and β-galactosidase. The fluorochromes that can be conjugated to the CH2 domain molecules include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals* (1992-1994). The metal compounds that can be conjugated to the CH2 or CH3 domain molecules include, but are not limited to, ferritin, colloidal gold, and particularly, colloidal superparamagnetic beads. The haptens that can be conjugated to the CH2 or CH3 domain molecules include, but are not limited to, biotin, digoxigenin, oxazalone, and nitrophenol. Additional reagents are well known in the art.

IX. Effector Functions of Antibody Constant Domain Molecules

Engineered CH2 or CH3 domains are capable of binding Fc receptors and/or compliment-related molecules such as C1q, which allows for a variety of effector functions, including antibody-dependent cell-mediated cytotoxicity (ADCC), complement dependent cytotoxicity (CDC), phagocytosis, opsonization and opsonophagocytosis. In some embodiments, the CH2 or CH3 domain molecules described herein comprise a binding site for one or more Fc receptors, thus enabling these molecules to mediate various effector functions (see Table 4 below). If effector functions are not desirable, the Fc binding site(s) can be mutated to prevent these functions.

The interaction of antibody-antigen complexes with cells of the immune system results in a wide array of responses, including a variety of effector functions and immunomodulatory signals. These interactions are initiated through the binding of the Fc domain of antibodies or immune complexes to specialized cell surface receptors, Fc receptors. Each member of the Fc receptor family recognizes immunoglobulins of one or more isotypes through a recognition domain on the Fc domain. Fc receptors are defined by their specificity for immunoglobulin subtypes (for example, Fc receptors for IgG are referred to as FcγR) (U.S. Pre-Grant Publication No. 2006-0134709).

Fc receptors are glycoproteins found on the surface of some cells of the immune system, including monocytes, macrophages, neutrophils, eosinophils, mast cells, natural killer cells, B cells and dendritic cells. Fc receptors exhibit a variety of cell expression patterns and effector functions (see Table 4). Fc receptors allow immune cells to bind to antibodies that are attached to the surface of microbes or microbe infected cells, helping these cells to identify and eliminate microbial pathogens. The Fc receptors bind antibodies at their Fc region, an interaction that activates the cell that possesses the Fc receptor.

TABLE 4

Cell Distribution and Effector Functions of Fc Receptors

| Receptor name | Cell distribution | Effector function |
|---|---|---|
| FcγRI (CD64) | Macrophages | Phagocytosis |
| | Neutrophils | Cell activation |
| | Eosinophils | Activation of respiratory burst |
| | Dendritic cells | Induction of microbe killing |

TABLE 4-continued

Cell Distribution and Effector Functions of Fc Receptors

| Receptor name | Cell distribution | Effector function |
| --- | --- | --- |
| FcγRIIA (CD32) | Macrophages<br>Neutrophils<br>Eosinophils<br>Platelets<br>Langerhans cells | Phagocytosis<br>Degranulation (eosinophils) |
| FcγRIIB1 (CD32) | B Cells<br>Mast cells | No phagocytosis<br>Inhibition of cell activity |
| FcγRIIB2 (CD32) | Macrophages<br>Neutrophils<br>Eosinophils | Phagocytosis<br>Inhibition of cell activity |
| FcγRIIIA (CD16a) | NK cells | Induction of ADCC |
| FcγRIIIB (CD16b) | Eosinophils<br>Macrophages<br>Neutrophils<br>Mast cells<br>Follicular dendritic cells | Induction of microbe killing |
| FcεRI | Mast cells<br>Eosinophils<br>Basophils<br>Langerhans cells | Degranulation |
| FcεRII (CD23) | B cells<br>Eosinophils<br>Langerhans cells | Possible adhesion molecule |
| FcαRI (CD89) | Monocytes<br>Macrophages<br>Neutrophils<br>Eosinophils | Phagocytosis<br>Induction of microbe killing |
| Fcα/μR | B cells<br>Mesangial cells<br>Macrophages | Endocytosis<br>Induction of microbe killing |
| FcRn | Monocytes<br>Macrophages<br>Dendritic cells<br>Epithelial cells<br>Endothelial cells<br>Hepatocytes | Transfers IgG from a mother to fetus through the placenta<br>Transfers IgG from a mother to infant in milk<br>Protects IgG from degradation |

Activation of phagocytes is the most common function attributed to Fc receptors. For example, macrophages begin to ingest and kill an IgG coated pathogen by phagocytosis following engagement of their Fcγ receptors. Another process involving Fc receptors is called antibody-dependent cell-mediated cytotoxicity (ADCC). During ADCC, FcγRIII receptors on the surface of natural killer (NK) cells stimulate the NK cells to release cytotoxic molecules from their granules to kill antibody covered target cells. However, FcεRI has a different function. FcεRI is the Fc receptor on granulocytes that is involved in allergic reactions and defense against parasitic infections. When an appropriate allergic antigen or parasite is present, the cross-linking of a least two of IgE molecules and their Fc receptors on the surface of a granulocyte will trigger the cell to rapidly release preformed mediators from its granules.

In addition, the Fc domains of IgG and IgM antibodies are capable of binding C1q, a component of the classical pathway of complement activation. When IgG or IgM antibodies are bound to the surface of a pathogen, C1q is capable of binding their Fc regions, which initiates the complement cascade, ultimately resulting in the recruitment of inflammatory cells and the opsonization and killing of pathogens.

To further provide functionality to the CH2 or CH3 domain molecules, effector molecules (for example, therapeutic, diagnostic, or detection moieties) can be linked to a CH2 or CH3 domain molecule using any number of means known to those of skill in the art. Exemplary effector molecules include, but are not limited to, radiolabels, fluorescent markers, or toxins. Both covalent and noncovalent attachment means can be used. The procedure for attaching an effector molecule to an antibody varies according to the chemical structure of the effector. Polypeptides typically contain a variety of functional groups; for example, carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (for example, enzymes or fluorescent molecules) drugs, toxins, and other agents to antibodies, one skilled in the art will be able to determine a suitable method for attaching a given agent to a CH2 or CH3 domain molecule.

Therapeutic agents include various drugs such as vinblastine, daunomycin and the like, and effector molecules such as cytotoxins such as native or modified *Pseudomonas* exotoxin or Diphtheria toxin, encapsulating agents, (such as, liposomes) which themselves contain pharmacological compositions, target moieties and ligands. The choice of a particular therapeutic agent depends on the particular target molecule or cell and the biological effect desired to be evoked. Thus, for example, the therapeutic agent may be an effector molecule that is cytotoxic which is used to bring about the death of a particular target cell. Conversely, where it is merely desired to invoke a non-lethal biological response, a therapeutic agent can be conjugated to a non-lethal pharmacological agent or a liposome containing a non-lethal pharmacological agent.

Toxins can be employed with a CH2 or CH3 domain molecule which is of use as an immunotoxin. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.).

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, *J. Virol.* 19:220, 1976), and has been used in human clinical trials. See, U.S. Pat. No. 5,792,458 and U.S. Pat. No. 5,208,021. As used herein, the term "diphtheria toxin" refers as appropriate to native diphtheria toxin or to diphtheria toxin that retains enzymatic activity but which has been modified to reduce non-specific toxicity.

Ricin is the lectin RCA60 from *Ricinus communis* (Castor bean). The term "ricin" also references toxic variants thereof. For example, see, U.S. Pat. No. 5,079,163 and U.S. Pat. No. 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Ribonucleases have also been conjugated to targeting molecules for use as immunotoxins (see Suzuki et al., *Nat. Biotech.* 17:265-70, 1999). Exemplary ribotoxins such as α-sarcin and restrictocin are discussed in, for example, Rathore et al., *Gene* 190:31-5, 1997; and Goyal and Batra, Biochem 345 Pt 2:247-54, 2000. Calicheamicins were first isolated from *Micromonospora echinospora* and are members of the enediyne antitumor antibiotic family that cause double strand breaks in DNA that lead to apoptosis (see, e.g., Lee et al., *J. Antibiot* 42:1070-87. 1989). The drug is the toxic moiety of an immunotoxin in clinical trials (see, for example, Gillespie et al., *Ann Oncol* 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., *Agr. Biol. Chem.* 52:1095, 1988; and Olsnes, *Methods Enzymol.* 50:330-335, 1978).

The following examples are provided to illustrate certain particular features and/or embodiments. These examples should not be construed to limit the invention to the particular features or embodiments described.

EXAMPLES

Example 1

Generation of a Library of Antibody CH2 Domains with Loops Containing Amino Acid Residues Randomly Mutated to any of the Four Residues, Y, S, A or D In this example, mutated CH2 domains were constructed in which loop 1 was replaced with 10 randomly arranged Y, S, A or D residues, plus an additional G at the C-terminal end of the loop. Similarly, loop 3 was replaced with 6 randomly arranged Y, S, A or D residues, plus an additional G at the C-terminal end of the loop. The DNA library is generated in three stages.

First, the CH2 DNA is used for generation of two fragments, fragment 1 and fragment 2, containing mutated loop 1 and loop 2, respectively. Fragment 1 is generated by PCR amplification using an N-terminal primer (5' GCA CTG GCT GGT TTC GCT ACC GT GGCC CAGGC GGCC GCA CCT GAA CTC CTG 3'; SEQ ID NO: 6) and a loop 1 reverse primer (5' CAC GTA CCA GTT GAA CTT GCC AKM AKM AKM AKM AKM AKM AKM AKM AKM AKM CAC CAC CAC GCA TGT GAC 3'; SEQ ID NO: 7), where K=G or T, and M=A or C. Fragment 2 is generated by using a loop 1 forward primer (5' AAG TTC AAC TGG TAC GTG 3'; SEQ ID NO: 8) and a loop 3 reverse primer (5' GAT GGT TTT CTC GAT GGG GCC AKM AKM AKM AKM AKM AKM GTT GGA GAC CTT GCA CTT G 3'; SEQ ID NO: 9).

Second, the two fragments are joined by the use of splicing by overlapping extension (SOE) PCR. During the second step of the SOE PCR, a C-terminal primer (5' GGT GCA GAA GAT GGT GGT GGCC GGCCT GGCC TTT GGC TTT GGA GAT GGT TTT CTC GAT G 3'; SEQ ID NO: 10) is used in addition to the N-terminal primer to introduce the restriction site Sfi1 on both ends of the DNA which is needed for the next stage of cloning.

Third, the amplified mutated CH2 fragments are digested with Sfi1 and ligated into a phagemid vector digested with the same enzyme. The product of ligation is desalted by washing three times with double distilled water using Amicon Ultra-4 centricon before transformation of TG1 cells by electroporation.

Sequences of 20 randomly selected clones from transformed TG1 cells are shown below (Table 5), demonstrating successful generation of CH2 mutants with randomized loops 1 and 3 by four residues, Y, S, D and A.

TABLE 5

Fragments of mutant CH2 sequences with randomized loops 1 and 3 (X2-22 denote names of clones)

Loop 1

```
x9  PEVTCVVV YYDSAAAYAY  GKFNWYVDG VEVHNAKTKP REEQYNSTYR  SEQ ID NO: 11)
x14 PEVTCVVV YYSASAAASA  GKFNWYVDG VEVHNAKTKP REEQYNSTYR  (SEQ ID NO: 12)
x13 PEVTCVVV YDSDYASSDD  GKFNWYVDG VEVHNAKTKP RKEQYNSTYR  (SEQ ID NO: 13)
x15 PEVTCVVV AYSDDAAAYD  GKFNWYVDG VEVHNAKTKP REEQYNSTYR  (SEQ ID NO: 14)
x10 PEVTCVVV DADDDYYYYY  GKFNWYVDG VEVHNAKTKP REEQYNSTYR  (SEQ ID NO: 15)
x2  PEVTCVVV DDAYYDADYYY GKFNWYVDG VEVHNAKTKP REEQYNSTYR  (SEQ ID NO: 16)
x11 PEVTCVVV DAAYDYSY    GKFNWYVDG VEVHNAKTKP REEQYNSTYR  (SEQ ID NO: 17)
x19 PEVTCVVV DYDSDDAYAD  GKFNWYVDG VEVHNAKTKP REEQYNSTYR  (SEQ ID NO: 18)
x16 PEVTCVVV SYYDSDSYSA  GKFNWYVDG VEVHNAKTKP REEQYNSTYR  (SEQ ID NO: 19)
x4  PEVTCVVV DDAYADDASA  GKFNWYVDG VEVHNAKTKP REEQYNSTYR  (SEQ ID NO: 20)
x17 PEVTCVVV SYYSDSDYDD  GKFNWYVDG VEVHNAKTKP REEQYNSTYR  (SEQ ID NO: 21)
x12 PEVTCVVV DDDSYYSYDD  GKFNWYVDG VEVHNAKTKP REEQYNSTYR  (SEQ ID NO: 22)
x22 PEVTCVVV YDASDYADAY  GKFNWYVDG VEVHNAKTKP REEQYNSTYR  (SEQ ID NO: 23)
x8  PEVTCVVV ADAAAYAYAD  GKFNWYVDG VEVHNAKTKP REEQYNSTYR  (SEQ ID NO: 24)
x7  PEVTCVVV ASDSSDDYD   GKFNWYVDG VEVHNAKTKP REEQYNSTYR  (SEQ ID NO: 25)
x5  PEVTCVVV AAAADADYY   SKFNWYVDG VEVHNAKTKP REEQYNSTYR  (SEQ ID NO: 26)
x20 PEVTCVVV YDDAAYADDY  GKFNWYVDG VEVHNAKTKP REEQYNSTYR  (SEQ ID NO: 27)
```

TABLE 5-continued

Fragments of mutant CH2 sequences with randomized loops 1 and 3
(X2-22 denote names of clones)

```
x21 PEVTCVVV SADASDYD   GKFNWYVDG VEVHNADTKP REEQYNSTYR   (SEQ ID NO: 28)
x23 PEVTCVVV DDDAADAYYY GKFNWYVDG VEVHNAKTKP REEQYNSTYR   (SEQ ID NO: 29)
x3  PEVTCVVV YDSDDDYDYA GKFCWYVDG VEVHNAKTKP REEHYNSTYR   (SEQ ID NO: 30)
```

Loop 3

```
x9  VVSVLTVLHQ DWLNGKEYKCKVSN AASAYS GPIEKTISKA K   (SEQ ID NO: 31)
x14 VVSVLTVLHQ DWLNGKEYKCKVSN ADDADA GPIEKTISKA K   (SEQ ID NO: 32)
x13 VVSVLTVLHQ DWLNGKEYKCKVSN AADAYA GPIEKTISKA K   (SEQ ID NO: 33)
x15 VVSVLTVLHQ DWLNGKEYKCKVSN AADYSD GPIEKTISKA K   (SEQ ID NO: 34)
x10 VVSVLTVLHQ DWLNGKEYKCKVSN AADAAD GPIEKTISKA K   (SEQ ID NO: 35)
x2  VVSVLTVLHQ DWLNGKEYKCKVSN DASASS GPIEKTISKA K   (SEQ ID NO: 36)
x11 VVSVLTVLHQ DWLNGKEYKCKVSN DDYAAS GPIEKTISKA K   (SEQ ID NO: 37)
x19 VVSVLTVLHQ DWLNGKEYKCKVSN DAYASD GPIEKTISKA K   (SEQ ID NO: 38)
x16 VVSVLTVLHQ DWLNGKEYKCKVSN DADDAS GPIEKTISKA K   (SEQ ID NO: 39)
x4  VVSVLTVLHQ DWLNGKEYKCKVSN AADDDS GPIEKTISKA K   (SEQ ID NO: 40)
x17 VVSVLTVLHQ DWLNGKEYKCKVSN ADAYAY GPIEKTISKA K   (SEQ ID NO: 41)
x12 VVSVLTVLHQ DWLNGKEYKCKVSN ADDYDY GPIEKTISKA K   (SEQ ID NO: 42)
x22 VVSVLTVLHQ DWLNGKEYKCKVSN YSDSAA GPIEKTISKA K   (SEQ ID NO: 43)
x8  VVSVLTVLHQ DWLNGKEYKCKVSN YAASAY GPIEKTISKA K   (SEQ ID NO: 44)
x7  VVSVLTVLHQ DWLNGKEYKCKVSN YDDDAD GPIEKTISKA K   (SEQ ID NO: 45)
x5  VVSVLTVLHQ DWLNGKEYKCKVSN YYDYDY GPIEKTISKA K   (SEQ ID NO: 46)
x20 VVSVLTVLHH DWMNGKEYKCEVSN DADSAD GPIKKTISKA K   (SEQ ID NO: 47)
x21 VVSVLTVLHH DWLNGEEYKCKVSN DASDDA GPIEKTIS.A K   (SEQ ID NO: 48)
x23 VVSVLTVLHQ DWLNGKEYKCKVSN ADDAYA GPIEKTISKA K   (SEQ ID NO: 49)
x3  VVSVLTVLHH YWMNGEDYKCEVSN DSYSDD GPIKKTISKA K   (SEQ ID NO: 50)
```

Example 2

Engraftment of CDR3s from Human Antibodies into CH2 Scaffold

In this example human VH CDR3s (H3s) from an antibody library are engrafted into CH2 by replacing loops A-B and E-F. First, the loop A-B is replaced by H3s using five PCRs. The first two PCRs generate two CH2 fragments without the loop A-B by using the following primers: for fragment 1—forward 1 primer (5' TAG CGA TTC GCT ACC GTG GCC CAG GCG GCC CCT GAA CTC CTG GGG GGA CC 3'; SEQ ID NO; 51) and reverse 1 primer (5' TCC CCC CAG GAG TTC AGG TGC 3'; SEQ ID NO; 52), for fragment 2—forward 2 primer (5' TGC GTG GTG GTG GAC GTG AGC 3'; SEQ ID NO: 53) and reverse 2 primer (5' TAG GCA TGC ATC TGC ATG GTG GCC GGC CTG GCC TTT GGC TTT GGA GAT GGT TTT CTC GAT GG 3'; SEQ ID NO: 54). The forward 1 and the reverse 2 primers contain the restriction site for SfiI which is required at the N- and C-termini in the final product. The reverse 1 and forward 2 primers contain end sequences needed for a subsequent SOE PCR. The third PCR uses as a template an antibody VH library and two mixtures of three primers each, designed to amplify diverse H3s. The mixture of forward primers contains H3 forward primer 1: 5' GAA CTC CTG GGG GGA CCG GCY AYR TAT TAC TGT GYG 3' (SEQ ID NO: 55), H3 forward primer 2: 5' GAA CTC CTG GGG GGA CCG GCY TTR TAT TAC TGT GYG 3' (SEQ ID NO: 56), and H3 forward primer 3: 5' GAA CTC CTG GGG GGA CCG GCY GTR TAT TAC TGT GYG 3' (SEQ ID NO: 57). The mixture of reverse primers contains H3 reverse primer 1: 5' GCT CAC GTC CAC CAC CAC GCA GGT GCC CTG GCC CCA 3' (SEQ ID NO: 58), H3 reverse primer 2: 5' GCT CAC GTC CAC CAC CAC GCA GGT GCC ACG GCC CCA 3' (SEQ ID NO: 59), and H3 reverse primer 3: 5' GCT CAC GTC CAC CAC CAC GCA GGT GCC AYG GCC CCA 3' (SEQ ID NO: 60). It generates a mixture of fragments containing H3s with end sequences designed to overlap with the respective end sequences of the reverse 1 and forward 2 primers. The two CH2 fragments and the H3 containing fragments are used as primers and templates in a SOE PCR to generate a fragment where loop AB is replaced by H3s. This mixture of fragments is amplified by using the forward 1 primer and the reverse 2 primers. The amplified fragments are digested with Sfi1 and ligated into a phagemid vector (pComb3X or pZUD) digested with the same enzyme. The product of ligation is desalted by washing three times with double distilled water using Amicon Ultra-4 centricon before transformation of TG1 cells by electroporation.

A similar procedure can be used for replacement of loop E-F, except that for amplification of fragment 1, instead of reverse primer 1 another primer—reverse primer 12 (5' GTA CGT GCT GTT GTA CTG CTC 3'; SEQ ID NO: 61) is used; for amplification of fragment 2—instead of forward primer 2 another primer—forward primer 22 (5' AAG GTC TCC AAC AAA GCC CTC 3'; SEQ ID NO: 62) is used; and for amplification of the H3s, the H3 primers are different. In this case, the mixture of forward primers contains H3 forward primer 12: 5' GAG CAG TAC AAC AGC ACG TAC GCA GCY AYR TAT TAC TGT GYG 3' (SEQ ID NO: 63), H3 forward primer 22: 5' GAG CAG TAC AAC AGC ACG TAC GCA GCY TTR TAT TAC TGT GYG 3' (SEQ ID NO: 64), and H3 forward primer 32: 5' GAG CAG TAC AAC AGC ACG TAC GCA GCY GTR TAT TAC TGT GYG 3' (SEQ ID NO: 65). The mixture of reverse primers in this case contains H3 reverse primer 12: 5' GAG GGC TTT GTT GGA GAC CTT GGT TCC CTG GCC CCA 3' (SEQ ID NO: 66), H3 reverse primer 22: GAG GGC TTT GTT GGA GAC CTT GGT GCC ACG GCC CCA 3' (SEQ ID NO: 67), and H3 reverse primer 32: 5' GAG GGC TTT GTT GGA GAC CTT GGT GCC AYG GCC CCA 3' (SEQ ID NO: 68). Finally, both loops, A-B and E-F, can be replaced with VH H3s. In this case. following replacement of loop A-B by H3s, loop E-F is replaced in the resulting fragments by H3s which are randomly recombined.

Figure 4:
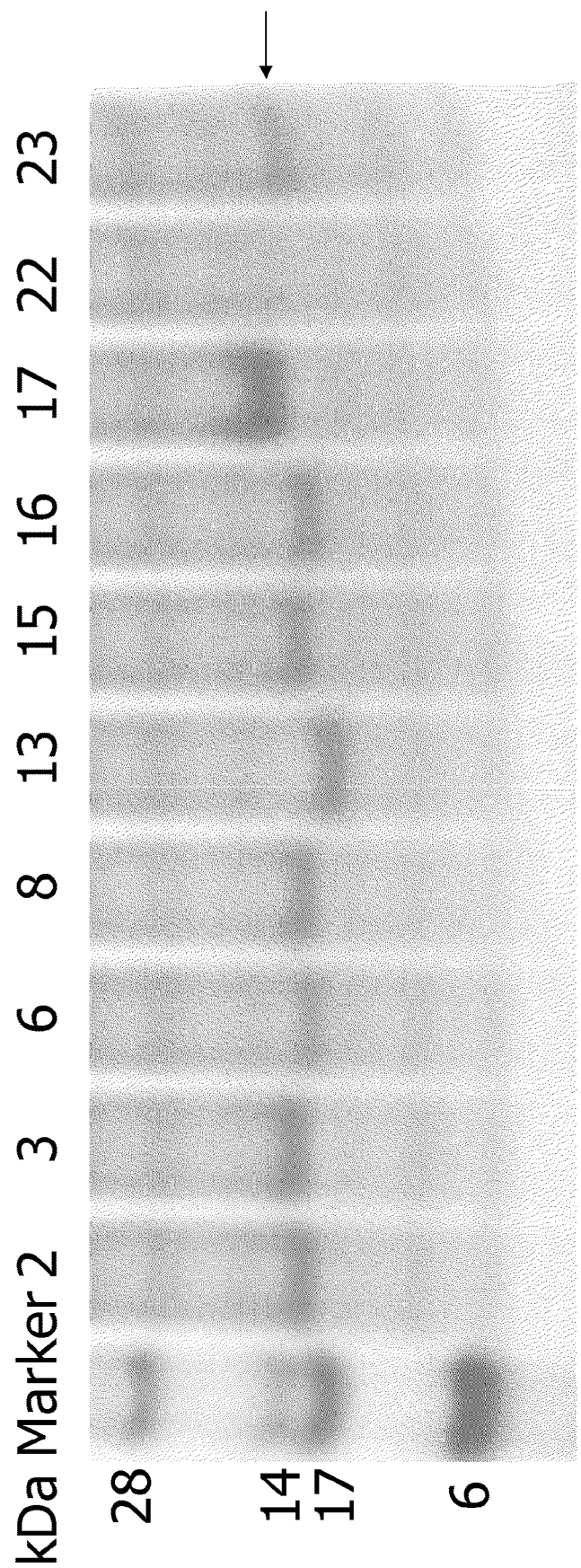
FIG. 4 shows an image of a gel demonstrating protein expression of engineered CH2 domains, which is indicated by the arrow.

Sequences of 19 randomly selected clones from transformed TG1 cells with both loops replaced by H3s are shown below (Table 6) suggesting successful grafting of H3s. FIG. 4 shows protein expression for several of these clones. The positions of the bands of the mutant molecules are indicated with an arrow.

TABLE 6

Fragments with grafted H3s
02-38 (SEQ ID NOs: 69-87, respectively) denote names of clones

| | H3 | | H3 |
|---|---|---|---|
| #2: | AVYYCV.KVPVGY............WGRGT & | AVYYCA.DVEASSPADFGY....WGRGT |
| #3: | AMYYCA.RDHGVDTAMAGPWFDY..WGRGT & | AVYYCV.RGTGWELLVIDC....WGRGT |
| #6: | AVYYCA.RGSSGWGWFDP.......WGQGT & | ATYYCA.RDRGY...........WGRGT |
| #8: | AVYYCA.RRMPEGDSSGTSYYFDY.WGQGT & | ALYYCA.REEKGDYDY.......WGQGT |
| #13: | AMYYCA.IHSFDY............WGQGT & | AVYYCA.KVLSGWFDHYFDS...WGQGT |
| #15: | AVYYCA.RDRVPDGVWSADS.....WGQGT & | AVYYCA.SKPPVSNWFDP.....WGQGT |
| #16: | AIYYCV.KAGYNFDAFDH.......WGRGT & | AMYYCA.GDTAMVIFDY......WGQGT |
| #17: | ATYYCA.SGSSGCSDY.........WGQGT & | ATYYCA.RGGYSSGWYHWYFDL.WGRGT |
| #22: | AVYYCA.ASVGAPSDFDY.......WGQGT & | ATYYCA.TTPDSNYGY.......WGQGT |
| #23: | ALYYCA.KGQYGDHDY.........WGQGT & | AVYYCA.KEEEGAVLG.......WGRGT |
| #25: | ATYYCA.REGTVVTPYFVY......WGQGT & | AVYYCA.MGGHGSGSYLSGY...WGQGT |
| #26: | AVYYCA.RERYGALDY.........WGRGT & | AVYYCA.GGLLHEGSGY......WGQGT |
| #28: | AIYYCA.ARGQGNSWWFDP......WGQGT & | AIYYCA.TQVGHGD.........WGQGT |
| #30: | ALYYCA.RAYSAYQYSFDS......WGRGT & | AVYYCA.RREYNWNHNWFDP...WGQGT |
| #31: | ATYYCA.RRGDDYGDYFFDY.....WGQGT & | AIYYCA.RSRGSSFDY.......WGQGT |
| #33: | AMYYCA.RDLYSNYVDY........WGQGT & | AVYYCA.RGPWQQLVNWFDP...WGQGT |
| #34: | ATYYCA.SLTGTTSY..........WGQGT & | ALYYCA.RATWGYQFDC......WGQGT |
| #36: | AIYYCA.RESSSSFDY.........WGQGT & | AVYYCA.RMSGGRWIFDH.....WGQGT |
| #38: | AVYYCA.RGWELDY...........WGQGT & | AVYYCA.KTGQFDY.........WGQGT |

Example 3

Engineering and Characterization of Stabilized CH2 Mutants

In this example, two mutants of CH2 are identified that exhibit an increased stability compared to the parental wild type CH2. Because the CH2 framework is already stabilized by internal disulfide bond between strands B and F, it was hypothesized that an additional disulfide bond between other strands could provide an overall increase in the CH2 stability. Several positions in strand A and G were mutated, of which one resulted in a very stable mutant CH2, designated as m01, where L (in the sequence GPSVFLFPPKPKDTL (SEQ ID NO: 88)) and the first K (in the sequence EKTISKAK (SEQ ID NO: 89)) were mutated to C. Another mutant, designated m02, where V (in GPSVFLFPPKPKDTL (SEQ ID NO; 90)) and the first K in EKTISKAK (SEQ ID NO: 91) were mutated to C, exhibited an increase in stability compared to the parental CH2, but lower than that of m01.

Materials and Methods

Cloning, expression and purification of CH2 domains. Human γ1 CH2 was cloned in bacterial expression vectors and used for transformation of *Escherichia coli* strain HB2151 cells which were grown at 37° C. in SB medium to an optical density of $OD_{600}$~0.6-0.8. Expression was induced with 1 mM IPTG at 37° C. for 12-16 hrs. Bacterial cells were harvested and re-suspended in Buffer A (50 mM Tris.Cl, 450 mM NaCl, pH 8.0) at 1:10 (volume of Buffer A: culture volume). Polymyxin B sulfate (Sigma-Aldrich, MO) (0.5 mu/ml) was added to the suspension (1:1000 volume of polymyxin B sulfate: culture volume). The cell lysate was subsequently clarified by centrifugation at 15,000 rpm for 45 min at 4° C. and tested for expression by SDS-PAGE and Western. The clarified supernatant was purified by using 1 ml HiTrap Chelating HP Ni-NTA column (GE Healthcare, NJ). After elution with Buffer B (50 mM Tris.Cl, 450 mM NaCl, 200 mM Imidazole, pH 8.0), the Imidazole was removed by Amicon Ultra—15 Centrifugal Filter Devices (MILLIPORE, MA) and the purified proteins were kept in Buffer A or PBS (9.0 g/L NaCl, 144 mg/L $KH_2PO_4$, 795 mg/L $Na_2HPO_4$, pH 7.4). The proteins were checked for purity by SDS-PAGE and their concentrations were determined by measuring the UV absorbance.

CH2 Mutant Design and Plasmid Construction.

To design the CH2 mutants the Fc crystal structure was used. Five mutants, V10/E103 to C10/C103, F11/K104 to C11/C104, L12/T105 to C11/C105, L12/K104 to C12/C104, and V10/K104 to C10/C104, were selected for characterization by analyzing the structure with the computer program VMD 18.6 (Humphrey et al., *J. Mol. Graph.* 14:33-38, 1996). They were made by PCR-based site-directed mutagenesis and cloned into bacterial expression vectors. The clones were verified by direct sequencing and used for transformation of the *Escherichia coli* strain HB2151. The mutants were expressed and purified similarly to the wild type CH2.

Size Exclusion Chromatography.

Purified CH2, CH2 m01 and CH2 m02 were loaded into the Hiload 26/60 Superdex 75 HR 10/30 column (GE Healthcare, NJ) running on ÄKTA BASIC pH/C chromatography system (GE Healthcare, NJ) to assess oligomer formation. Buffer A was selected as mobile phase. A gel-filtration standard consisting of aldolase (158 kD), bovine serum albumin (67 kDa), ovalbumin (44 kDa), chymotrypsinogen A (25 kD) and ribonuclease A (17 kDa) was used to define the molecular weight of CH2, CH2 m01 and CH2 m02.

Determination of Disulfide Bonds by Mass Spectrometry.

The total number of disulfide bonds in purified CH2, CH2 m01 and CH2 m02 was determined through Voyager 4700 MALDI-TOF/TOF mass spectrometry) (Applied Biosystems, CA) by comparing the molecular masses after (A) reduction and alkylation of all SH groups and (B) alkylation of the original free SH groups without reduction of disulfide bonds. Reduction was carried out with TCEP, and alkylation was performed with iodoacetamide.

Circular Dichroism (CD).

The secondary structure of CH2, CH2 m01 and CH2 m02 were determined by circular dichroism (CD) spectroscopy. The purified proteins were dissolved in PBS at the final concentration of 0.49 mg/ml, and the CD spectra were recorded on AVIV Model 202 CD Spectrometer (Aviv Biomedical, NJ). Wavelength spectra were recorded at 25° C. using a 0.1 cm path-length cuvette for native structure measurements. Thermodynamic stability was measured at 216 nm by recording the CD signal in the temperature range of 25-90° C. with heating rate 1° C./min. After heating, wavelength spectra were recorded at 90° C. For evaluation of the refolding, all the samples were kept at 4° C. overnight and measured again at 25° C. The temperature was recorded with an external probe sensor and the temperature inside the microcuvette was calculated by calibration—was about 2-3° C. (range from 1.9° C. to 3.8° C. for temperatures from 20° C. to 80° C.) lower that the one measured by the external sensor.

Differential Scanning Calorimetry (DSC).

The thermal stabilities of CH2, CH2 m01 and CH2 m02 were further monitored with a VP-DSC MicroCalorimeter (MicroCal, Northampton, Mass.). The concentrations of three proteins were 1.5 mg/ml in PBS (pH 7.4). The heating rate employed was 1° C./min and the scanning was performed from 25 to 100° C.

Spectrofluorometry.

The intrinsic fluorescence of CH2, m01 and m02 were recorded on a Fluorometer Fluoromax-3 (HORIBA Jobin Yvon, NJ). Intrinsic fluorescence measurements were performed using a protein concentration of 10 µg/ml with excitation wavelength at 280 nm, and emission spectra recorded from 320 to 370 nm at 25° C. Buffer A in the presence of urea from 0 to 8 mM was used. With all samples, fluorescence spectra were corrected for the background fluorescence of the solution (buffer+denaturant). Fluorescence intensity at 340 nm was used for unfolding evaluation.

Nuclear Magnetic Resonance (NMR).

For the NMR experiments *E. coli* was first grown in 2×YT. Single colony was inoculated in 3 mL 2×YT for about 3 hrs, then turbidity was checked and bacteria transferred to 1 liter 2×YT medium for further growth at 37° C. until $OD_{600}$~0.8-0.9 was reached. The cell culture was then centrifuged to remove the 2×YT medium and replaced it with a M9 minimum medium with $^{15}N$ $NH_4Cl$ and $^{13}C$ glucose as sole $^{15}N$ and $^{13}C$ sources, respectively (17). The cells were incubated at 30° C. over night, and induced with 1 mM IPTG. Harvested cells were suspended in TES buffer (10 mL buffer for 1 L of culture) for 1 h on ice. Osmotic shock to release periplasmic proteins was induced by adding 1.5 volume TES/5 on ice for 4 hrs. The supernatant was then dialyzed in a dialysis buffer (50 mM Tris.Cl, 0.5 M NaCl) over night at 4° C. The protein was purified by the method described above for an initial purification. Fractions containing a significant amount of the protein were then loaded on Sephacryl S-200 column (GE Healthcare, NJ) for further purification. The separated fractions samples were collected in Buffer A.

NMR experiments were performed in 40 mM Tris.Cl buffer at pH 7.8 containing 64 mM NaCl in 95% $H_2O$/5% $D_2O$ and a sample volume of approximately 300 µl in a 5-mm Shigemi tube (Shigemi Inc, PA) with a protein concentration of 0.5-0.8 mM at 25° C. NMR experiments were conducted using a Bruker Avance 600 MHz instrument which is equipped with a cryogenic probe (Bruker Instruments, MA). Water-flip back sequences were used for $^1H$—$^{15}N$ HSQC and $\{^1H\}$—$^{15}N$ NOE experiments to minimize exchange between amide protons and water protons (Grzesiek and Bax, *J. Am. Chem. Soc.* 115:12593, 1994). $^1H$—$^{15}N$ HSQC spectra were recorded with 1024 complex points for an acquisition dimension with a spectral width of 8012 Hz, and 256 complex points for an indirect ($t_1$) dimension. $\{^1H\}$—$^{15}N$ NOE experiments were conducted with the similar number of points by recording two sets of spectra, with and without proton saturation at 3 and 4 second repetition delays, respectively (Gong and Ishima, *J. Biomol. NMR* 37:147-157, 2007). Uncertainties of the NOE values were estimated from r.m.s.d. noise of the two spectra and peak heights.

Signal assignments were performed based on HNCA, CBCACONH, CCONH experiments for CH2 domain, and HNCACB and CBCACONH and $^{13}C$, $^{15}N$ simultaneous evolution NOESY for CH2 m01 domain (Kay et al., *J. Magn. Reson.* 89:496-514, 1990; Muhandiram and Kay, *J. Magn. Res. Series B.* 103:203-216, 1994). NMR data were processed and analyzed using the nmrPipe (Delaglio et al., *J. Biomol. NMR* 6:277-293, 1995; Masse and Keller, *J. Magn. Reson.* 174:133-151, 2005). To color significance of chemical shift changes on CH2 backbone structure, a normalized chemical shift changes, $\delta_{norm}=\sqrt{(\delta_{C\alpha})^2+(\gamma_{C\alpha}/\gamma_N)^2(\delta_N)^2}$, its average, and standard deviation (s.d.) were calculated, and are grouped to four classes: $\delta_{norm}>3.0$ (red), $3.0>\delta_{norm}>2.0$ (orange), $2.0>\delta_{norm}>1.0$ (yellow), and (4) $\delta<1$ (blue).

Results

Isolated, Unglycosylated Human γ1 CH2 Domain is Relatively Stable.

Human γ1 heavy chain CH2 (FIG. 5A) was cloned in a bacterial expression vector, expressed and purified as described in above. Human γ1 CH2 expresses at high levels as soluble protein (more than 10 mg per liter of bacterial culture) and is highly soluble (more than 10 mg/ml). It is monomeric in PBS at pH 7.4 as determined by size exclusion chromatography (FIG. 5B) (Prabakaran et al., *Acta Crystallogr. B.* 64:1062-1067, 2008). SDS-PAGE of human γ1 CH2 revealed an apparent molecular weight (MW) of about 14-15 kDa, which is close to the calculated MW (14.7 kDa, including the His and FLAG tags). As expected, it is much smaller than the MWs of scFv, Fab and IgG1 (FIG. 5C).

Previously, it has been found that an isolated unglycosylated murine CH2 domain is relatively unstable at physiologically relevant temperatures ($T_m$=41° C. as measured by circular dichroism (CD) (Feige et al., *J. Mol. Biol.* 344:107-118, 2004). The sequence of human CH2 differs from that of the murine one which could lead to different stabilities (FIG. 5A).

To test the thermodynamic stability of human γ1 CH2, both CD and differential scanning calorimetry (DSC) were used. As measured by CD, the secondary structure of CH2 consisted of beta strands at 25° C. The CH2 unfolding started at about 42° C. and was completed at about 62° C. (FIG. 6A) with a calculated Tm of 54.1±1.2° C. (FIG. 6A), The unfolding was reversible (FIG. 6A). Similar results were obtained by DSC (Tm=55.4° C., FIG. 6B). Thus the human γ1 CH2 is significantly more stable than its murine counterpart.

Design and Generation of Engineered Human γ1 CH2 Domains with an Additional Disulfide Bond.

To further improve the stability of human CH2, an additional disulfide bond was engineered between the N-terminal strand A and the C-terminal strand G. It was reasoned that constraining the degrees of freedom of these two strands could lead to a decrease in the extent of unfolding. The mutants were initially designed based on the crystal structure of CH2 in an intact Fc which is very similar to the crystal structure of isolated CH2 which was recently reported although there are certain differences in some loops and at the termini (Prabakaran et al., *Acta Crystallogr. B.* 64:1062-1067, 2008). Based on the distance between two C α-carbons in proteins with known structure (Dani et al., *Protein Eng.* 16:187-193, 2003; Pellequer and Chen, *Proteins* 65:192-202, 2006) and the orientation of the bonds, five amino acid pairs were selected: V10/E103, F11/K104, L12/T105, L12/K104 and V10/K104 (the numbering starts with 1:Ala, corresponding to number 231 in the γ1 heavy chain) (FIG. 5A; SEQ ID NO: 5), which were substituted by Cys. Two mutants (L12/K104 to C12/C104, distance between the $C^\alpha$s in L12 and K104=6.53 Å, and V10/K104 to C10/C104, distance between the $C^\alpha$s in V10 and K104=7.25 Å) (FIG. 7), designated m01 and m02, respectively, were highly soluble and expressed at levels comparable or higher than CH2 (FIG. 8).

The existence of an additional disulfide bond was confirmed by mass spectrometry. The number of disulfide bonds in CH2 was one, and in mutants m01 and m02 it was two, as expected (Table 7). These mutants were selected for further characterization.

M01 and m02 are Significantly More Stable than CH2.

Figure 9A:
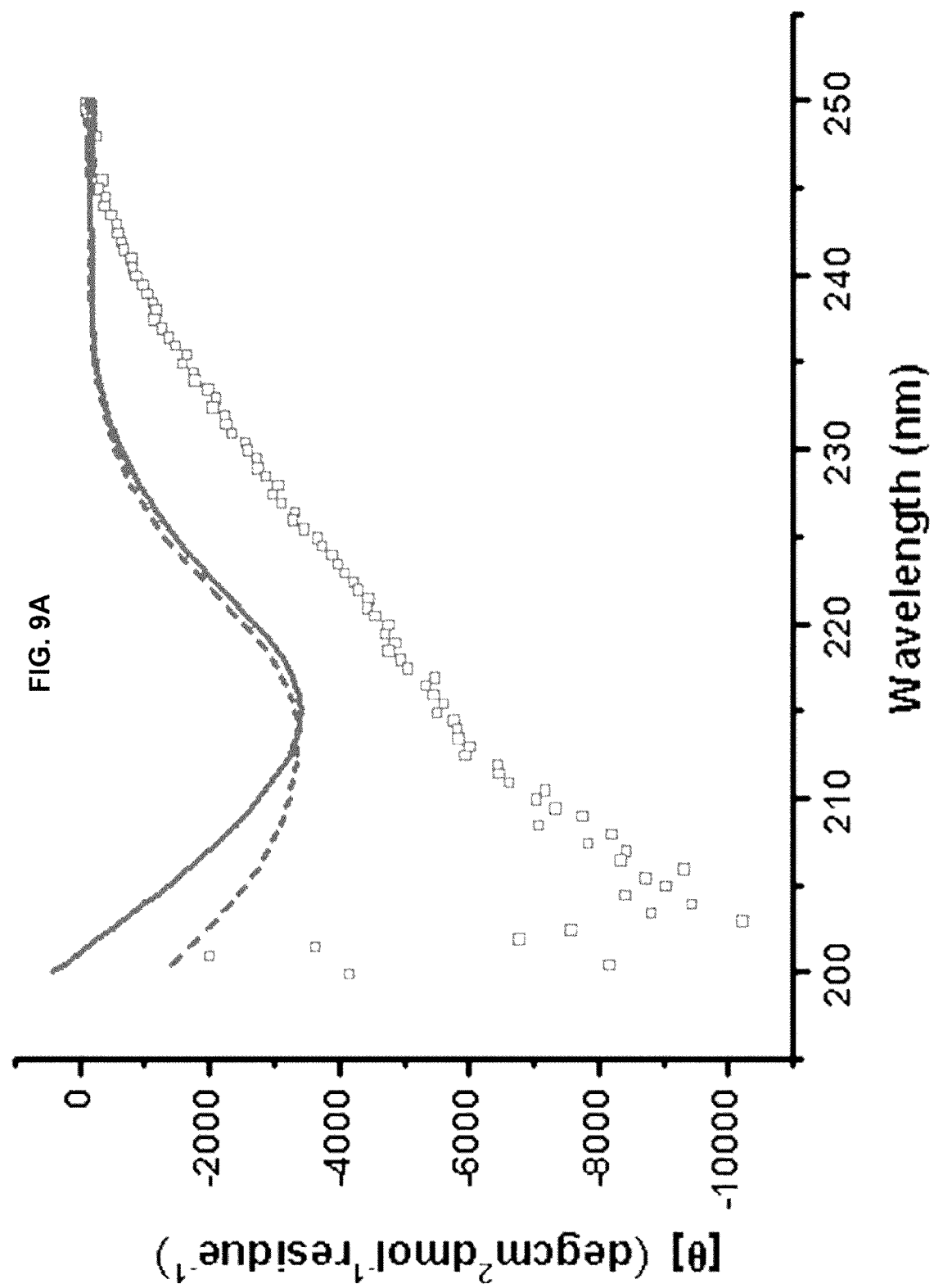
Figure 9B:
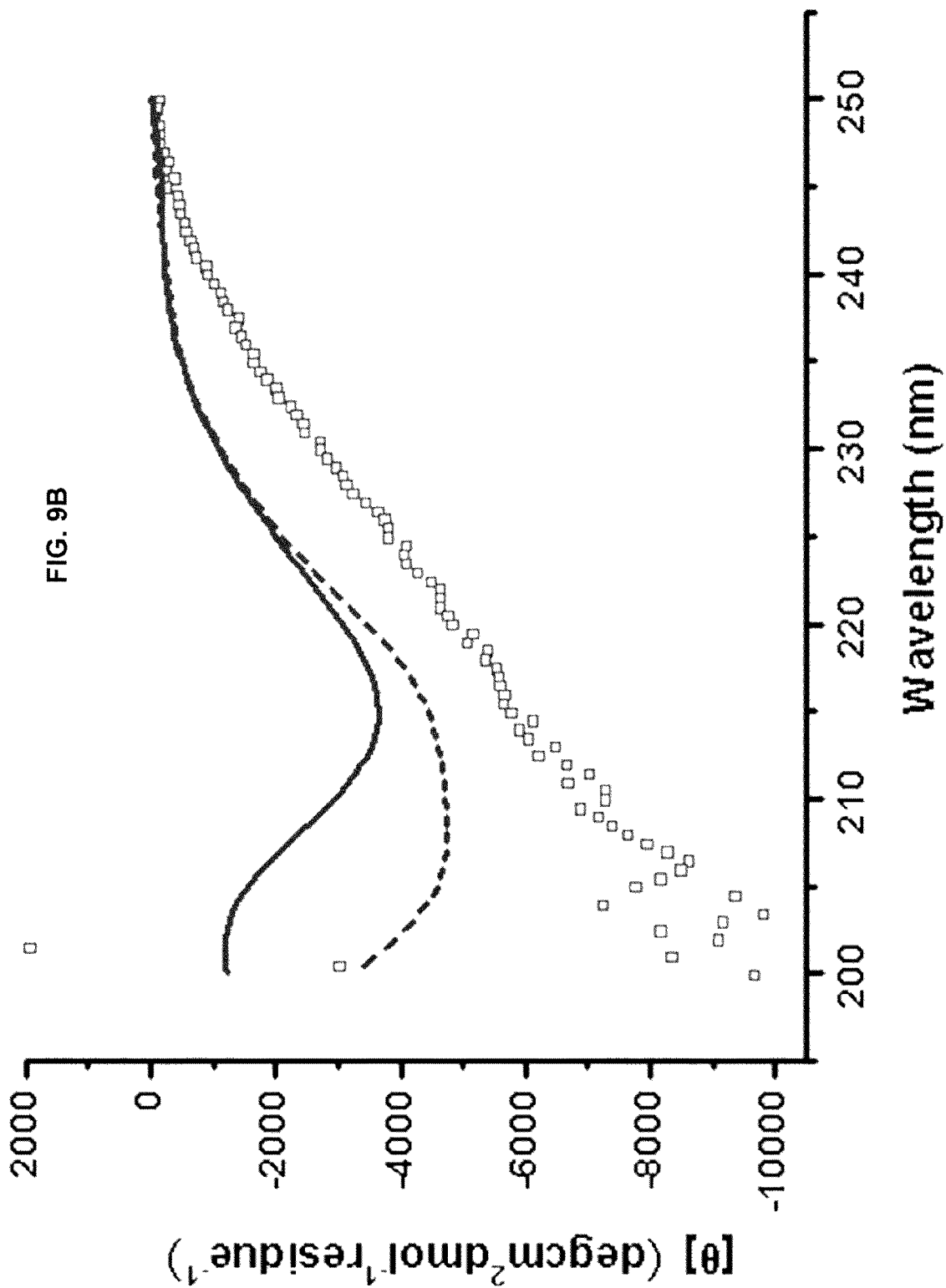
Figure 9C:
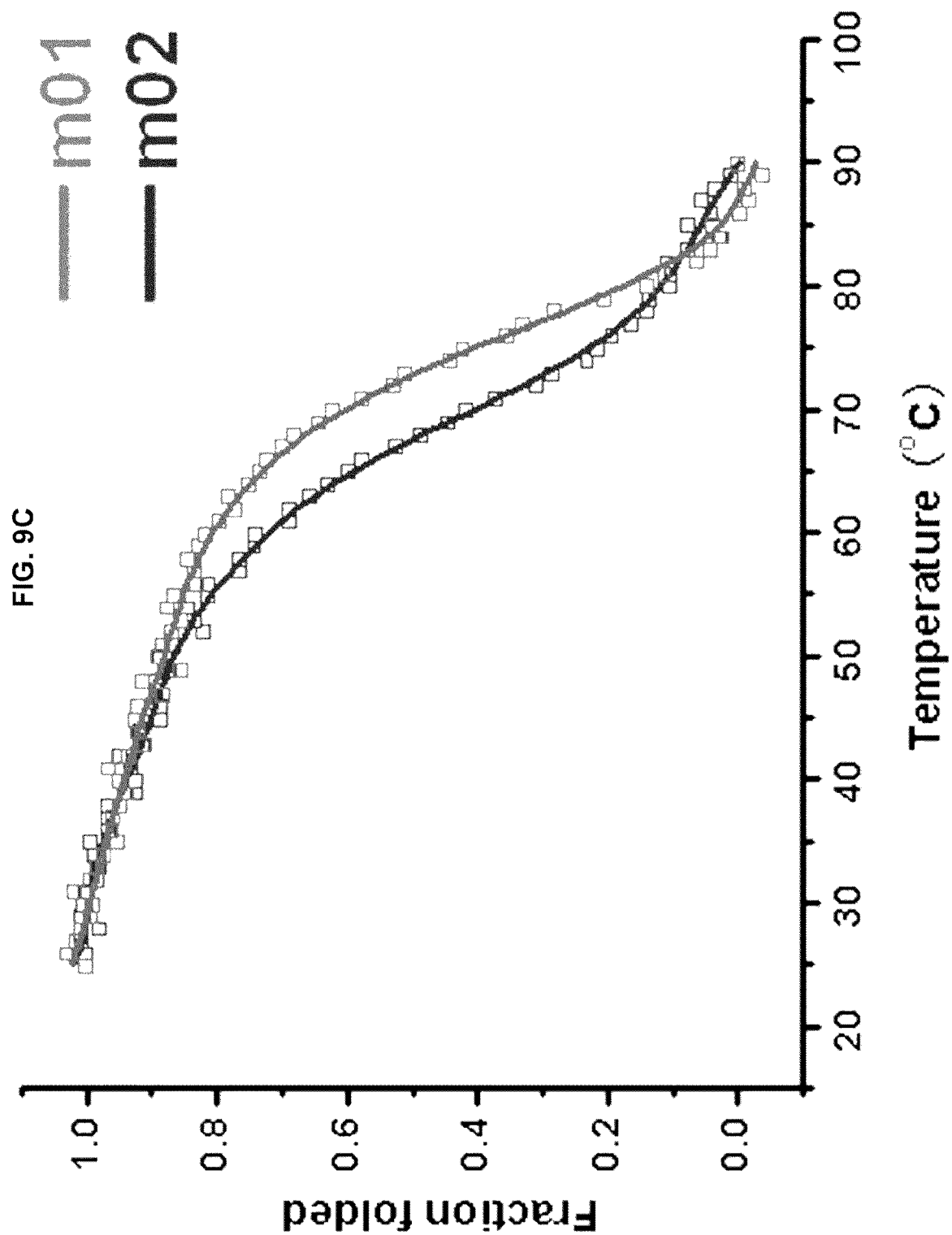

The thermodynamic stability of m01, m02 and CH2 was measured by CD and DSC, and their stability against chemical agents was determined by using urea and spectrofluorimetry. In all cases, the two mutants were much more stable than CH2 (FIG. 9). The CD spectra of CH2, m01 and m02 showed that they had high β-sheet content at 25° C. (FIGS. 9A and 9B). The β-sheet structure was gradually disrupted as the temperature increased (FIG. 9C). At 90° C., the structure was in an unfolded state (FIGS. 9A and 9B). The sigmoidal curve was fitted by a two-state model as also previously reported (Feige et al., *J. Mol. Biol.* 344:107-118, 2004). Notably, 50% unfolding of m01 and m02 occurred at temperatures (Tm=73.8±1.7° C. and 65.3±0.6° C., respectively) that were significantly higher than that of native CH2 (54.1±1.2° C.) (FIG. 9C). CH2 and m01 refolded reversibly; however, m02 only partially re-folded (FIG. 9A and FIG. 6A versus FIG. 9B).

Figure 9D:
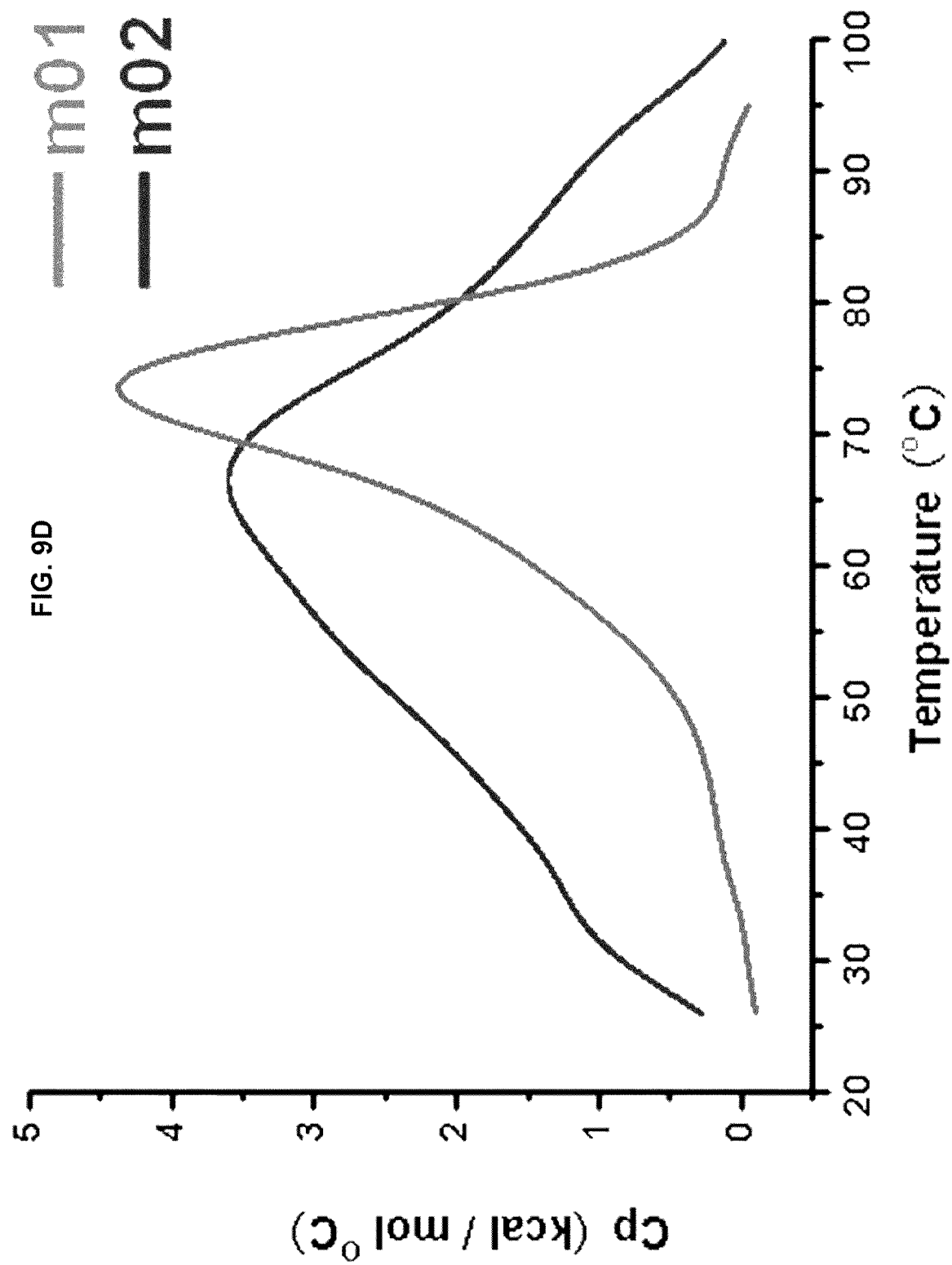

Similar results were obtained by DSC. The melting temperatures of m01 and m02 were much higher than that of native CH2, which also increased about 20° C. and 10° C., respectively (FIG. 9D). Interestingly, the unfolding of m02 was broader and with lower peak than those of CH2 and m01. This phenomenon could be caused by the presence of dimers in m02.

Figure 9E:
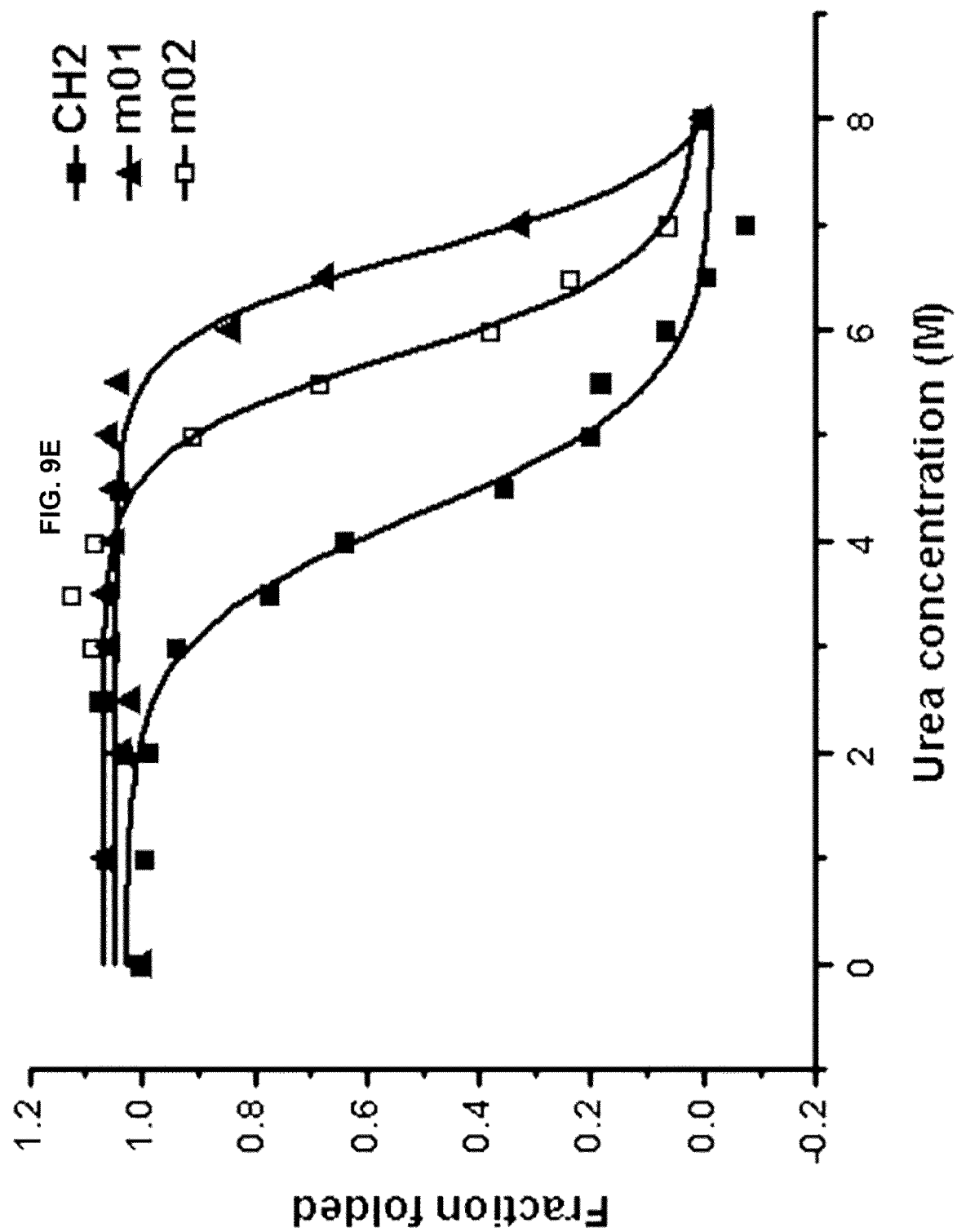

The stability against chemically induced unfolding of m01 and m02 was also higher than that of CH2 (FIG. 9E). Urea was used as a chemical agent to measure the intrinsic fluorescence spectra. The unfolding dependences on the urea concentration can be also fitted by a two-state model. The 50% unfolding of m01 and m02 occurred at higher urea concentrations (6.8 and 5.8 M, respectively) than that of CH2 (4.2 M).

Only monomer fraction was observed for m01 while m02 contained small amounts of higher molecular species, mostly dimers as determined by SEC (FIG. 10). Because of its superior properties, m01 was selected for further characterization. The stability of a truncated CH2 (CH2s) and a truncated m01 (m01s) where the first seven N-terminal residues were deleted (residues 1-7 of SEQ ID NO: 5) were also tested. These truncated proteins exhibited high stability. The 50% unfolding temperatures (Tms) measured by CD (62° C. and 79° C., respectively) are significantly higher (8° C. and 5° C., respectively) than those of the corresponding CH2 and m01 (54° C. and 74° C., respectively) (FIG. 10B).

Structural Conservation of m01.

To examine structural perturbation caused by the cysteine mutations, solution NMR experiments were performed for the CH2 domain and the m01 mutant. $^1$H—$^{15}$N HSQC spectrum generally shows a correlation of nitrogen atoms and their directly bounded protons, and provides a "fingerprint" of the protein backbone. Each of the $^1$H—$^{15}$N HSQC spectra of CH2 and the m01 (recorded in identical experimental conditions) exhibited only one set of peaks, indicating that the protein was well-folded in solution. Of the structure region of the proteins, the chemical shifts of backbone $^{15}$N, C', and $C_\alpha$ were ca. 75% assigned in both proteins. In m01, the measured chemical shifts for $C_\alpha$ and $C_\beta$ of residue Cys 12 were 57.6 ppm and 37.7 ppm, respectively, whereas the $C_\alpha$ and $C_\beta$ chemical shifts of Cys 104 were 34.2 ppm and 54.5 ppm, respectively. These values fall within the expected range for oxidized cysteine residues (Sharma and Rajarathnam, *J. Biomol. NMR* 18:165-171, 2000), demonstrating that the additional disulfide bridge is formed in the m01 mutant.

TABLE 7

Number of disulfide bonds determined by mass spectrometry

| Protein | Intact (Da) | Denatured (D) (Da) | Reduced (R) (Da) | Reduced/Alkylate (R/A) (Da) | Alkylated (A) (Da) | $N_{cys}$ | $N_{SH}$ | Number of -s-s- |
|---|---|---|---|---|---|---|---|---|
| CH2 | 14707.3607 | 14714.5977 | 14710.9160 | 14822.6719 | 14708.5791 | 2 | 0 | 1 |
| CH2 m01 | 14674.3447 | 14677.7539 | 14676.3398 | 14899.9238 | 14669.0400 | 4 | 0 | 2 |
| CH2 m02 | 14688.9561 | 14686.2461 | 14695.6543 | 14901.8076 | 14686.1230 | 4 | 0 | 2 |

$N_{cys} = (M_{R/A})/57$
$N_{SH} = (M_A - M_D)/57$
Number of disulfide bond (-s-s-) = $(N_{cys} - N_{SH})/2$ Comparison of the overall backbone chemical shits of N and $C_\alpha$ also showed the overall similarity of the protein structures between CH2 and the m01. However, changes in chemical shifts were observed around residues Cys31 and Cys91 as well as around the newly introduced Cys residues 12 and 104. This is not unexpected because the newly introduced disulfide bridge is proximal to the native Cys31-Cys91 by linking the adjacent β-strands in the same β-sheet with the Cys31-Cys91 bridge. The newly introduced disulfide bond in CH2 m01 most likely affected microscopic environments of the native disulfide bond between Cys31 and Cys91.

Relatively High Loop Flexibilities and Rigid Framework of CH2 and m01.

To determine whether the loops are flexible in both CH2 and m01, $^{15}N$—{$^{1}H$} NOE was recorded. It was determined that the framework is rigid as indicated by the high NOE values (above 0.7); in contrast the loops were on average more flexible. The local dynamics of CH2 and m01 were comparable, demonstrating that the conformational entropy of m01 at the native states is very similar to that of CH2. It is most likely that the essential structure and dynamics of the CH2 domain is maintained while thermal stability is increased upon introduction of the cysteine mutation. The increase in the flexibility of the loops also indicates that both CH2 and m01 could be used as scaffolds for grafting to or mutating residues in the loops.

Example 4

CH2 Domain Molecules Specific for HIV

This example describes the construction of a synthetic phage library, based on the loops of the CH2 domain of human IgG1, to identify CH2 molecules that specifically bind HIV envelope.

Materials and Methods

Primers, Peptide and Proteins.

All the primers used in this study were purchased from Invitrogen (Carlsbad, Calif.). The biotin labeled peptide was from Sigma (St. Louis, Mo.). Bal gp120-CD4 was kindly provided by Tim Fouts (University of Maryland, Baltimore, Md.) and other gp120/140 were provided by Christopher Broder (USUHS, Bethesda, Md.). SCD4 was obtained through AIDS research and reagent program.

Library Construction.

Overlapping PCR was used to introduce mutations to loops 1 and 3 to generate the first CH2 based library. N terminus primer ACGT GGCCCAGGCGGCC GCA CCT GAA CTC CTG (SEQ ID NO: 101) and loop 1 primer CAC GTA CCA GTT GAA CTT GCC AKM AKM AKM AKM AKM AKM AKM AKM AKM AKM CAC CAC CAC GCA TGT GAC (SEQ ID NO: 7) were used to generate the N terminal half of the CH2 containing mutations in loop 1. Loop 1 linkage primer AAG TTC AAC TGG TAC GTG (SEQ ID NO: 8) and loop 3 primer GAT GGT TTT CTC GAT GGG GCC AKM AKM AKM AKM AKM AKM GTT GGA GAC CTT GCA CTT G (SEQ ID NO: 9) were used to generate the rest of CH2 with mutations in loop 3. The two fragments were then combined by a overlapping PCR step and amplified with the N terminus primer and C terminus primer ACGT GGCCGGCCTGGCC TTT GGC TTT GGA GAT GGT TTT CTC GAT G (SEQ ID NO: 102) with a SfiI site (underlined) being introduced into both ends of the CH2 fragment. To generate the secondary library based on the binders isolated from the first library, loop 2 primer GCT GAC CAC ACG GTA ADH ADH ADH GTA CTG CTC CTC CCG (SEQ ID NO: 103) and above described N terminus primer were used to introduce mutations to loop 2 to the primary binder. Loop 2 linkage primer TAC CGT GTG GTC AGC (SEQ ID NO: 104) and loop 3 primer (2) GGA GAT GGT TTT CTC GAT GGG ADH TGG ADH ADH ADH GTT GGA GAC CTT GCA (SEQ ID NO: 105) were used to introduce mutations to the primary binder. The two fragments were joined by an overlapping PCR step and amplified using the same pair of N and C terminus primers described above for amplification. PCR fragments were subject to SfiI digestion and ligated to the vector. The ligated product was desalted and transformed to the electro-competent TG1 cells suing an electroporator (Bio-Rad, Hercules, Calif.). A phage library was prepared from the resulted transformants.

Panning.

Bal gp120-CD4, Bal gp120 as well as BSA were coated directly to Maxisorp plates (Nunc, Denmark) in PBS buffer at 4° C., overnight for a plate format panning Approximately $10^{13}$ phage particles of the respective CH2 libraries were suspended in PBS with 2% dry milk and applied to wells coated with the proteins. After 2 hours at room temperature, each well was washed 5 times for the first round and 10 times for the subsequent rounds before the phages were rescued with TG1 cells at the exponential growth phase. A total of five rounds of panning were performed for each antigen for the first library. For the second library based on the primary binder, three rounds of panning were performed. Monoclonal ELISA was then used to select for positive clones. Two hundred clones were screened for each antigen. Only clones displaying an OD 405>2.0 in the monoclonal ELISA were selected for plasmid preparation and sequencing.

CH2 Expression and Refolding.

Clones selected as described above were transformed into *E. coli* strain HB2151 for expression. Briefly, a single clone was inoculated into 2×YT supplemented with 100 units of amp and incubated at 37° C. with shaking. When the $OD_{600}$ reached 0.5, IPTG was added to achieve a final concentration of 1 mM and the culture was continued with shaking for another 3-5 hours. Cells were then collected, lysed with polymyxin B (Sigma, St Louis) in PBS, and the supernatant was subjected to Ni-NTA agarose bead (Qiagen, Hilden, Germany) purification for the soluble portion of the CH2 clones. The pellet was then re-suspended in buffer containing 25 mM Tris.HCl, pH 8.0, 6 M Urea, 0.5 M NaCl, and subjected to brief sonication. The supernatant was collected by centrifugation and subjected to Ni-NTA agarose bead (Qiagen) purification. CH2 obtained through the pellet was subjected to overnight dialysis against two changes of PBS and then filtered through a 0.2 μm low protein binding filter (Pal, Ann Arbor, Mich.).

ELISA.

Different protein antigens were diluted in the PBS buffer in concentrations ranging from 1-4 μg/ml and coated to the 96 well plate at 4° C. overnight. The plate was then blocked with PBS+5% dry milk buffer. CH2 clones in different concentrations were diluted in the same blocking buffer and applied to the ELISA plate. Mouse-anti-His-HRP was used to detect the His tag at the C terminal end of each of the CH2 clones in most of the ELISA unless indicated otherwise. ABTS was then added to each well and $OD_{405}$ was taken 5-10 minutes afterward.

Gel Filtration Analysis.

Samples of purified and filtered CH2 proteins were analyzed on a Superdex75 10/300GL column (GE Healthcare, Piscataway, N.J.) pre-equilibrated with PBS. The column was calibrated with molecular weight standards. CH2 samples were eluted from the column at a flow rate of 0.5 ml/min.

Pseudovirus Neutralization Assay.

HIV Env pseudotyped virus preparation and neutralization was performed essentially as previously described (Choudhry et al., *Virology* 363:79-90, 2007).

Results

Design and Construction of a Human CH2-Based Library.

It was hypothesized that limited mutagenesis of the CH2 loops may not significantly affect the folding and stability of many mutants and could be used for the generation of large libraries of potential binders. First, mutagenesis of loop 1 (L1) and loop 3 (L3) was undertaken because they are the longest (9 and 5 residues, respectively) two loops on the same side of the molecule (loops BC, DE and FG are herein referred to as L1, L2 and L3, respectively; the two helices AB and EF are referred to as H1 and H2, respectively; and the loop CD is referred to as L0) (FIG. 11) (Radaev et al., *J. Biol. Chem.* 276:16469-16477, 2001). Four frequently occurring residues in CDRs (A, Y, D, and S) were selected to randomly replace all L1 and L3 residues and to add one additional residue. An additional residue (G) was also added to the C-terminal end of each loop to increase flexibility (FIG. 11). It has been previously observed that these four residues (sometimes only two) are sufficient to build a specific binding surface within different frameworks (Fellouse et al., *Proc. Natl. Acad. Sci. USA* 101:12467-12472, 2004; Koide et al., *Proc. Natl. Acad. Sci. USA* 104:6632-6637, 2007). The calculated theoretical diversity of this library is $4^{16}=4.3\times10^9$. However, due to potential mutations generated by PCR (see below) the diversity is likely to be significantly higher up to the size of the library ($5\times10^{10}$). Most mutants (probably greater than 80%) have correct reading frames as indicated by an analysis of 100 randomly selected clones.

Identification and Sequence Analysis of Binders.

To test the library and select potentially useful binders, an HIV-1 envelope glycoprotein, gp120, from the Bal isolate, fused with a two-domain CD4 (denoted as gp120$_{Bal}$-CD4) was used as an antigen. After five rounds of panning, 200 clones were screened by phage ELISA and 15 clones with the highest signal were isolated for further characterization. Three clones, m1a1, m1a2 and m1a3, dominated represented by 7, 5 and 2 (out of 15) sequences, respectively, suggesting a specific enrichment. They have similar L1 sequences, composed mostly of D and Y but their L3s are very different. The most abundant clones, m1a1 and m1a2, have several changes in L1 (two Fs in L1, and deletion before G, respectively) apparently due to PCR errors. The loop 1 and loop 3 sequences of the clones selected against Bal gp120-CD4 are shown below in Table 8. These results suggest that CH2-based scaffolds can support phage-displayed binders with varying L1 and L3; the newly identified HIV-1-specific binders were further characterized as described below.

TABLE 8

| CH2 Loop 1 and Loop 3 Sequences | | | | |
|---|---|---|---|---|
| Clone | Loop 1 sequence | SEQ ID NO: | Loop 3 sequence | SEQ ID NO: |
| m1a1 | DYDYDSYFDFG | 107 | SDSAASG | 110 |
| m1a2 | DYDYDSYYD..G | 108 | DDYAADG | 111 |
| m1a3 | DYDYDSYYDYG | 109 | YDYADDG | 112 |
| m1a3'* | DYDYDSYYDYG | 109 | SDYDSSG | 113 |

TABLE 8-continued

| CH2 Loop 1 and Loop 3 Sequences | | | | |
|---|---|---|---|---|
| Clone | Loop 1 sequence | SEQ ID NO: | Loop 3 sequence | SEQ ID NO: |
| wt CH2 | DVSHEDPEV | 93 | KALPA | 95 |
| | (aa 4-12) | | (aa 4-8) | |

*The m1a3' clone has the same loop 1 sequence as m1a3 but has a different loop 3 sequence Expression of Soluble nAbs and Characterization of their Binding.

Most of the expressed CH2 domain molecules (referred to as "nAbs") were found in inclusion bodies (FIG. 12A) and were refolded as described above, yielding on average 10-30 mg per L of bacterial culture. The purified nAbs bound to the panning antigen (gp120-CD4) specifically as measured by ELISA with EC50s ranging from 500 nM (m1a1 and m1a2) to low μM (m1a3) (FIG. 12B). Similar results were obtained for nAbs purified from the supernatant. These results suggest that m1a1, m1a2 and m1a3 retain their binding activity in soluble (not phage-displayed) form and that refolding from inclusion bodies does not affect these molecules. The two clones with highest affinity, m1a1 and m1a2, were selected for further characterization.

To test their cross-reactivity, four (Bal, JRFL, R2 and 89.6) recombinant HIV-1 envelope glycoproteins were used alone and in complex with soluble CD4. As shown in FIG. 14, m1a1 binds to various degrees to all proteins. While m1a1 binds to Bal gp120 in complex with CD4, but very weakly to gp120 alone as expected for a CD4 induced (CD4i) antibody, its binding to the other proteins was not affected significantly by the presence of CD4. The decrease in signal for the Env alone is not significant and could be due to the slightly reduced coating by gp120 when mixed with sCD4. Similar results were obtained for m1a2. These data suggest that the epitope recognized by these antibodies is CD4i for one isolate (Bal) but not for the others.

To further characterize their epitope, m1a1 competition with already known CD4i antibodies (scFv X5 and the domain antibody m36) was tested. Both CD4i antibodies competed significantly with m1a1. Therefore, m1a1 recognizes a novel conserved epitope that is shared by other highly potent cross-reactive CD4i antibodies, but in contrast to those antibodies its exposure by the gp120 interaction with CD4 is significantly dependent on the isolate.

Loop 1 Determines the Binding Specificity.

To determine the different contributions of the loops from the CH2 clones to the specific binding, two hybrid clones were generated: m1a1CH2 and m1a2CH2. L1s from m1a1 and m1a2 were grafted onto CH2 replacing the original L1. These hybrid antibodies bound to gp120-CD4 with about the same although slightly lower affinity compared to m1a1 as measured by ELISA (FIG. 13A), indicating that L3s are not essential for binding. To find out whether the scaffold as a whole is required for binding, m1a1 L1 was tested in isolation as a synthetic peptide (DYDYDSYFDFG; SEQ ID NO: 109). The biotin labeled peptide did not bind. The effect of relatively minor conformational changes in the scaffold on binding was also tested by creating an additional disulfide bond between strands A and G. As described in Example 3, such S—S bond increases significantly the CH2 stability and does not affect significantly the mobility and the microenvironment of any CH2 residue as measured by NMR. The resulting antibody m1a1ss did not bind either (FIG. 13B). These data suggest that the scaffold is required for the binding activity of m1a1, and that while changes in L3 may not affect its activity, relatively small changes in the scaffold conformation could abolish it.

Neutralization of HIV-1 Pseudovirus by m1a1 and m1a2.

To assess the neutralizing activity of m1a1 and m1a2, a cell line/pseudovirus assay and a panel of nine HIV-1 isolates was used. Seven of these isolates were inhibited to a certain degree by one or both antibodies (FIG. 14A). The two antibodies differentially inhibited two isolates (89.6 and IIIB) and to about the same degree five other isolates (FIG. 14A). As expected from their relatively modest binding affinity, their potency was relatively modest compared to the highly potent inhibitor C34 used here as positive control. These results provide proof of concept that functional binders can be selected from libraries based on the CH2 scaffold.

The antibodies were further improved by mutagenesis of the second and third loop (FIG. 15). They ran mostly monomeric on SDS gels (FIG. 16A). One of the mutants, m1b3, was mostly monomeric in gel filtration (FIG. 16B). They bound specifically (FIG. 16C) and neutralize to various extent HIV-1 (FIG. 17). They also competed with scFv X5 and m36 suggesting that they target a highly conserved region on the HIV-1 gp120 (FIG. 18).

This disclosure provides antibody constant domain molecules comprising at least one mutation, or at least one CDR, or functional fragment thereof. The disclosure further provides compositions comprising the antibody constant domain molecules and their use. It will be apparent that the precise details of the methods described may be varied or modified without departing from the spirit of the described invention. We claim all such modifications and variations that fall within the scope and spirit of the claims below.

The invention claimed is:

1. A polypeptide comprising a human immunoglobulin CH2 domain of IgG, IgA or IgD, or a human immunoglobulin CH3 domain of IgE or IgM, wherein the CH2 domain or CH3 domain comprises an N-terminal truncation of 7 amino acids, and wherein Loop 1 of the CH2 or CH3 domain is mutated, wherein the polypeptide has a molecular weight of less than about 15 kD, and wherein the polypeptide specifically binds an antigen.

2. The polypeptide of claim 1, wherein the polypeptide comprises a CH2 domain from IgG.

3. The polypeptide of claim 1, wherein the CH2 domain or CH3 domain further comprises a mutated Loop2, a mutated Loop3, a mutated Loop A-B, a mutated Loop C-D, a mutated Loop E-F, or any combination thereof.

4. The polypeptide of claim 1 having a molecular weight of about 12 kD to about 14 kD.

5. The polypeptide of claim 1, wherein the CH2 domain or CH3 domain further comprises a C-terminal truncation of about 1 to about 4 amino acids.

6. The polypeptide of claim 1, wherein the CH2 domain or CH3 domain is capable of binding an Fc receptor, a complement protein, or both.

7. The polypeptide of claim 1, wherein the antigen is from a pathogen.

8. The polypeptide of claim 7, wherein the pathogen is a virus or bacterium.

9. The polypeptide of claim 8, wherein the virus is human immunodeficiency virus (HIV).

10. The polypeptide of claim 1, wherein the antigen is a cancer-specific antigen or a tumor-associated antigen.

11. The polypeptide of claim 10, wherein the cancer is leukemia, lymphoma, multiple myeloma, malignant melanoma, breast cancer, lung cancer, prostate cancer, colon cancer or renal cell carcinoma.

12. The polypeptide of claim 1, wherein the antigen is TNF-α.

13. A composition comprising the polypeptide of claim 1 and a pharmaceutically acceptable carrier.

14. A composition comprising the polypeptide of claim 1 conjugated to an effector molecule or a detectable label.

15. The polypeptide of claim 1, further comprising a first amino acid substitution and a second amino acid substitution, wherein the first and second amino acid substitutions each replace the original residue with a cysteine residue, wherein the cysteine residues form a disulfide bond.

16. The polypeptide of claim 15, wherein the first amino acid substitution is in the N-terminal A strand and the second amino acid substitution is in the C-terminal G strand.

17. The polypeptide of claim 15 comprising a CH2 domain of IgG.

18. The polypeptide of claim 17, wherein the first amino acid substitution is L12 to C12 and the second amino acid substitution is K104 to C104 (numbered with reference to SEQ ID NO: 5).

19. The polypeptide of claim 17, wherein the first amino acid substitution is V10 to C10 and the second amino acid substitution is K104 to C104 (numbered with reference to SEQ ID NO: 5).

20. The polypeptide of claim 1, wherein the mutated Loop 1 comprises random substitutions of any combination of alanine, tyrosine, aspartic acid or serine residues.

21. The polypeptide of claim 20, wherein all Loop 1 residues are replaced by alanine, tyrosine, aspartic acid or serine residues.

22. The polypeptide of claim 20, wherein the mutated Loop 1 further comprises an extra glycine residue on the C-terminus of Loop 1.

23. The polypeptide of claim 1, wherein the CH2 domain or CH3 domain further comprises a mutated Loop 3, and wherein the mutated Loop 3 comprises random substitutions of any combination of alanine, tyrosine, aspartic acid or serine residues.

24. The polypeptide of claim 23, wherein all Loop 3 residues are replaced by alanine, tyrosine, aspartic acid or serine residues.

25. The polypeptide of claim 23, wherein the mutated Loop 3 of the CH2 domain or CH3 domain further comprises an extra glycine residue on the C-terminus of Loop 3.

* * * * *